(12) United States Patent
Che et al.

(10) Patent No.: US 10,378,046 B2
(45) Date of Patent: Aug. 13, 2019

(54) METHOD OF TARGETING MISMATCHED DNA USING D8 SQUARE PLANAR METAL COMPLEXES

(71) Applicant: The University of Hong Kong, Hong Kong (CN)

(72) Inventors: Chi Ming Che, Hong Kong (CN); Sin Ki Fung, Hong Kong (CN); Taotao Zou, Hong Kong (CN)

(73) Assignee: The University of Hong Kong, Hong Kong (CN)

( * ) Notice: Subject to any disclaimer, the term of this patent is extended or adjusted under 35 U.S.C. 154(b) by 285 days.

(21) Appl. No.: 15/167,151

(22) Filed: May 27, 2016

(65) Prior Publication Data

US 2016/0369354 A1 Dec. 22, 2016

Related U.S. Application Data

(60) Provisional application No. 62/182,864, filed on Jun. 22, 2015.

(51) Int. Cl.
*C12Q 1/68* (2018.01)
*C12Q 1/6827* (2018.01)
*C12Q 1/6886* (2018.01)

(52) U.S. Cl.
CPC ......... *C12Q 1/6827* (2013.01); *C12Q 1/6886* (2013.01); *C12Q 2600/156* (2013.01)

(58) Field of Classification Search
CPC .................................................. C12Q 1/6827
USPC ......................................................... 435/6.1
See application file for complete search history.

(56) References Cited

FOREIGN PATENT DOCUMENTS

WO WO-2007/084380 A2 7/2007

OTHER PUBLICATIONS

Zou, T. et al., "Luminescent Cyclometalated Platinum(II) Complex Forms Emissive Intercalating Adducts with Double-Stranded DNA and RNA: Differential Emissions and Anticancer Activities", *Angewandte Chemie*, 2014, 126:10283-10287, Wiley-VCH Verlag GmbH & Co. KGaA, Weinheim.

Loeb, L.A. "A Mutator Phenotype in Cancer", *Cancer Research*, Apr. 15, 2001, 61:3230-3239, American Association for Cancer Research.
Glaab, W.E. et al., "Mutation rate at the hprt locus in human cancer cell lines with specific mismatch repair-gene defects", *Carcinogenesis*, 1997, 18(1):1-8, Oxford University Press.
Eryazici, I. et al., "Square-Planar Pd(II), Pt(II), and Au(III) Terpyridine Complexes: Their Syntheses, Physical Properties, Supramolecular Constructs, and Biomedical Activities", *Chem. Rev.*, 2008, 108:1834-1895, American Chemical Society.
Bruijnincx, P.C.A. et al., "New trends for metal complexes with anticancer activity", *Current Opinion in Chemical Biology*, 2008, 12:197-206, 2007 Elsevier Ltd.
Zhou, W. "Mapping genetic alterations in tumors with single nucleotide polymorphisms", *Curr Opin Oncol*, 2003, 15:50-54, Lippincott Williams & Wilkins, Inc.
McConnell, A.J. et al., "Luminescent Properties of Ruthenium(II) Complexes with Sterically Expansive Ligands Bound to DNA Defects", *Inorganic Chemistry*, Oct. 31, 2012, 51:12511-12520, American Chemical Society.
Jackson, B.A. et al., "Recognition of DNA Base Mismatches by a Rhodium Intercalator", *J. Am. Chem. Soc.*, 1997, 119(52):12986-12987, American Chemical Society.
Ma, D. et al., "Platinum(II) Complexes with Dipyridophenazine Ligands as Human Telomerase Inhibitors and Luminescent Probes for G-Quadruplex DNA", *J. Am. Chem. Soc.*, 2009, 131(5):1835-1846, American Chemical Society.
Che, C. et al., "Platinum(II) Complexes of Dipyridophenazine as Metallointercalators for DNA and Potent Cytotoxic Agents against Carcinoma Cell Lines," *Chem. Eur. J.*, 1999, 5(11):3350-3356, WILEY-VCH Verlag GmbH, D-69451 Weinheim.
Fung, S.K. et al., "Luminescent platinum(II) complexes with functionalized N-heterocyclic carbene or diphosphine selectively probe mismatched and abasic DNA," *Nature Communications*, Feb. 17, 2016, 7(10655):1-9.
Lim, M.H. et al., "Sensitivity of Ru(bpy)$_2$dppz$^{2+}$ Luminescence to DNA Defects," Inorganic Chemistry, 2009, 48:5392-5397, American Chemical Society.

*Primary Examiner* — Jezia Riley
(74) *Attorney, Agent, or Firm* — Saliwanchik, Lloyd & Eisenschenk

(57) ABSTRACT

Disclosed are methods of using d$^8$ square planar metal complexes containing tridentate π-conjugated ligands and ancillary ligand of N-heterocyclic carbene or di-phosphine ligand to target mismatched DNA. Targeting of mismatched DNA can be revealed by monitoring the differences in emission enhancement of metal complexes toward mismatched DNA and matched DNA; or the gradually heat release from isothermal titration calorimetry (ITC) when complexes bind toward mismatch DNA; or the significant increase in melting temperature of the mismatched DNA after adding complexes.

20 Claims, 16 Drawing Sheets

METHOD OF TARGETING MISMATCHED DNA USING D8 SQUARE PLANAR METAL COMPLEXES

FIELD OF THE INVENTION

Generally disclosed herein are methods of targeting mismatched DNA. More particularly, disclosed herein are methods of targeting mismatched DNA by using $d^8$ square planar metal complexes.

BACKGROUND OF THE INVENTION

Due to the clinical success of cis-diamminedichloroplatinum(II) (cisplatin) for cancer treatment, there has been many research efforts on investigating metal-based anti-cancer drugs, including the cisplatin analogues and ruthenium (II)-arene complexes which target DNA [Sadler, P. J. et al. *Curr. Opin. Chem. Biol.* 2008, 12, 197]. However, these drugs often showed low selectivity between normal cells and cancer cells, resulting in severe side effects accompanied with the treatment. Recently, the deficiencies in DNA mismatch repair (MMR) have been shown to be correlated with cancerous transformations with cancer cells generally showing a high frequency of mismatched sites due to their deficiencies in MMR [Loeb, L. A. A. et al. *Cancer Res.* 2001, 61, 3230]. As a result, DNA mismatched sites have become novel diagnostics and therapeutics targets for cancer treatment because of their high occurring rates in cancer cells.

Re-sequencing is a universal method for the detection of DNA mismatched site [Zhou, W. et al. *Curr. Opin. Oncol.* 2003, 15, 50]. It is an expensive method because of complicated data processing and material consumption. Development of simple and efficient detection methods, such as designing luminescent probes toward mismatched DNA is needed. Recently, Barton and coworkers discovered that the $d^6$ octahedral metal complex, $Rh(bpy)_2chrysi^{3+}$(chrysi=5,6-chrysenequinone diimine, bpy=2,2'-bipyridine), can preferentially bind to thermodynamically destabilized mismatched site through bulky chrysi ligand [Barton, J. K. et al. *J. Am. Chem. Soc.* 1997, 119, 12986]. The sterically bulky ligand are thought to hinder the insertion of Rh complex toward well-matched DNA, leading to good selectivity. However, due to the non-emissive d-d ligand field (LF) state, which is at a comparable energy level to those of the luminescence excited states of rhodium(III) complexes, no significant luminescence signals can be observed at room temperature, thus limiting the use of rhodium(III) complexes as luminescent probes. The same author reported another $d^6$ octahedral ruthenium(II) comple also containing sterically bulky ligands for targeting mismatched DNA. It was found that Δ-$[Ru(bpy)_2dppz]^{2+}$ showed more significant emission enhancement toward defective DNA than matched DNA [Barton, J. K. et al. *Inorg. Chem.* 2012, 51, 12511].

Metal complexes having $d^8$ electron configuration and thus square planar geometry are also known to bind to DNA through intercalation [Newkome, G R, et al *Chem. Rev.*, 2008, 108, 1834-1895]. The binding with secondary DNA can be rendered specific providing appropriate ligand design, examples of which are luminescent platinum(II) complexes selectively targeting G-quadraplex DNA and differentiating between dsRNA and dsDNA [Che, C.-M. et al. *J. Am. Chem. Soc.* 2009, 131, 1835, Che, C.-M. et al. *Angew. Chem.* 2014, 126, 10283]. However, the field of using $d^8$ square planar metal complexes to target matched DNA still in its infancy.

There is a need, therefore, for new methods of targeting matched DNA using $d^8$ square planar metal complexes.

SUMMARY OF THE INVENTION

The following presents a simplified summary of the invention in order to provide a basic understanding of some aspects of the invention. This summary is not an extensive overview of the invention. It is intended to neither identify key or critical elements of the invention nor delineate the scope of the invention. Rather, the sole purpose of this summary is to present some concepts of the invention in a simplified form as a prelude to the more detailed description that is presented hereinafter.

Disclosed are methods of targeting mismatched DNA by using $d^8$ square planar metal complexes. The synthesis, structure, and reactivity of the $d^8$ square planar metal complexes are also described herein. By targeting, it is meant the binding and interacting of the $d^8$ square planar metal complexes with mismatched DNA, and detecting the mismatched DNA by using the $d^8$ square planar metal complexes. The amount of the $d^8$ square planar metal complexes used for targeting mismatched DNA is an effective amount of the $d^8$ square planar metal complexes for binding with mismatched DNA. The effective amount of the $d^8$ square planar metal complexes is dependent on the type mismatched DNA.

In some embodiments, the method involves bringing into contact a DNA sample and a $d^8$ square planar metal complex, and detecting the emission of the complex intercalated into DNA in the sample. Emission above a threshold level indicates the presence of mismatched DNA in the sample. Generally, the complex can be said to target mismatched DNA, where "targeting" means binding or interacting. Generally, the $d^8$ square planar metal complexes are used in the methods in an effective amount. As used herein, an "effective amount," in the context of the disclosed complexes, is an amount sufficient to detect an increase in emission of the complex when intercalated in mismatched DNA in a DNA sample as compared to the same complex when brought into contact with unmismatched DNA in a DNA sample. The effective amount of the complex generally depends on the type mismatched DNA.

As used herein, "mismatched DNA" refers to DNA containing one or more non-pairing nucleobases. As used herein, "non-pairing nucleobases" refers to a pair of nucleobases that do not form a canonical Watson-Crick based pair when across from each other in otherwise basepaired DNA strands. For example, the non-pairing nucleobases can be selected from the group consisting of adenine/adenine (A/A), adenine/guanine (A/G), adenine/cytosine (A/C), guanine/guanine (G/G), guanine/thymine (G/T), thymine/cytosine (T/C), thymine/thymine (T/T), and cytosine/cytosine (C/C) nucleobases.

The emission of the complex intercalated into DNA can be detected using any suitable technique. For example, the emission of the complex intercalated into DNA can be detected by emission spectroscopy, UV-Vis absorption spectroscopy, isothermal titration calorimetry (ITC), or nuclear magnetic resonance (NMR) spectroscopy.

In some embodiments, the DNA sample can include one or more cells or tissue of a subject. Because cancer cells often include much more mismatched DNA than normal cell, detection of emission of the complex intercalated into DNA above a threshold level can indicate that the cell is a cancer cell. In some embodiments, the method can further include treating the subject with an anti-cancer therapy. The subject can include, but is not limited to, a human.

Also disclosed are $d^8$ square planar metal complexes where the complex has a structure according to Formula I or Formula II, or a pharmaceutically acceptable salt thereof:

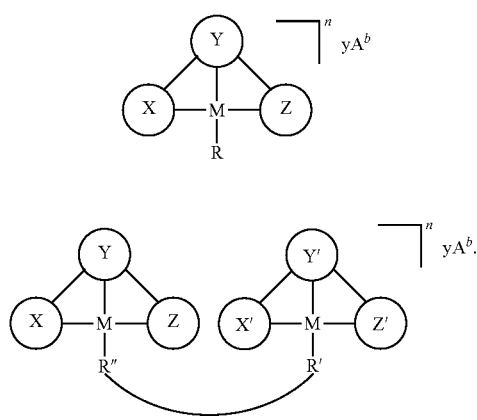

In some embodiments of Formula I and Formula II:

X^Y^Z and X'^Y'^Z' are each, independently, a tridentate π-conjugated ligand;

X, Y, Z, X', Y', and Z' are each, independently, carbon or nitrogen;

R, R', and R" are each, independently, a N-heterocyclic carbene ligand or a phosphine ligand;

each M is a $d^8$ metal atom;

n is the charge of the complex;

A is the counter-ion for the complex;

b is the charge of the counter-ion; and y is the absolute value of n/b.

In some embodiments, the $d^8$ metal atom can be platinum (II) (Pt(II) or $Pt^{2+}$), palladium(II) (Pd(II) or $Pd^{2+}$), gold(III) (Au(III) or $Au^{3+}$), silver (III) (Ag(III) of $Ag^{3+}$), copper(III) (Cu(III) or $Cu^{3+}$), nickel(II) (Ni(II) or $Ni^{2+}$), cobalt(I) (Co(I) or $Co^+$), rhodium(I) (Rh(I) or $Rh^+$), or iridium(I) (Ir(I) or $Ir^+$). In some embodiments of complexes of Formula II, R'^R" is a bis-N-heterocyclic carbene or diphosphine ligand.

In some embodiments, the complex can have a structure according to Formula I-A, or a pharmaceutically acceptable salt thereof:

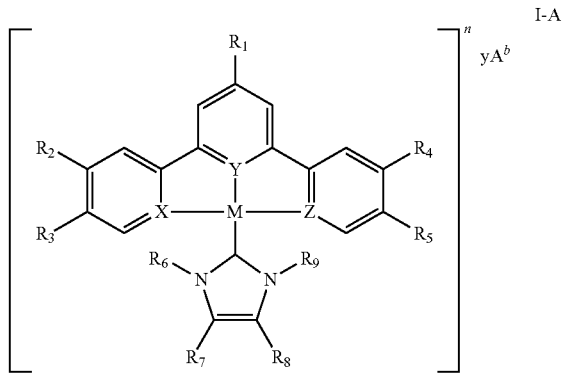

where $R_1$, $R_2$, $R_3$, $R_4$, $R_5$, $R_6$, $R_7$, $R_8$, and $R_9$ are each independently hydrogen, substituted or unsubstituted $C_1$-$C_6$ alkyl, substituted or unsubstituted $C_1$-$C_6$ alkenyl, substituted or unsubstituted $C_1$-$C_6$ alkynyl, substituted or unsubstituted phenyl, substituted or unsubstituted aryl, substituted or unsubstituted heteroaryl, substituted or unsubstituted $C_1$-$C_6$ alkoxy, substituted or unsubstituted phenoxy, substituted or unsubstituted aroxy, substituted or unsubstituted $C_1$-$C_6$ alkylthio, substituted or unsubstituted phenylthio, substituted or unsubstituted arylthio, substituted or unsubstituted $C_1$-$C_6$ carbonyl, substituted or unsubstituted $C_1$-$C_6$ carboxyl, substituted or unsubstituted $C_1$-$C_6$ amino, substituted or unsubstituted $C_1$-$C_6$ amido, substituted or unsubstituted $C_1$-$C_6$ sulfonyl, $C_1$-$C_6$ sulfonic acid, substituted or unsubstituted $C_1$-$C_6$ phosphoryl, substituted or unsubstituted $C_1$-$C_6$ phosphonyl, substituted or unsubstituted diaryl, substituted or unsubstituted $C_3$-$C_6$ cyclic, or substituted or unsubstituted heterocyclic; and where optionally and independently the pairs $R_2$ and $R_3$, $R_4$ and $R_5$, $R_6$ and $R_7$, $R_7$ and $R_8$, and $R_8$ and $R_9$ together are —$(CH_2)_{3-5}$—.

Preferably, $R_1$, $R_2$, $R_3$, $R_4$, $R_5$, $R_6$, $R_7$, $R_8$, and $R_9$ are each independently hydrogen, substituted or unsubstituted $C_1$-$C_6$ alkyl, substituted or unsubstituted $C_1$-$C_6$ alkenyl, substituted or unsubstituted $C_1$-$C_6$ alkynyl, substituted or unsubstituted phenyl, substituted or unsubstituted aryl, substituted or unsubstituted heteroaryl, substituted or unsubstituted $C_1$-$C_6$ alkoxy, substituted or unsubstituted phenoxy, substituted or unsubstituted aroxy, substituted or unsubstituted diaryl, substituted or unsubstituted $C_3$-$C_6$ cyclic, or substituted or unsubstituted heterocyclic. More preferably, $R_1$, $R_2$, $R_3$, $R_4$, $R_5$, $R_6$, $R_7$, $R_8$, and $R_9$ are each independently hydrogen, unsubstituted $C_1$-$C_6$ alkyl, unsubstituted $C_1$-$C_6$ alkenyl, unsubstituted $C_1$-$C_6$ alkynyl, unsubstituted phenyl, unsubstituted aryl, unsubstituted heteroaryl, unsubstituted $C_1$-$C_6$ alkoxy, unsubstituted phenoxy, unsubstituted aroxy, unsubstituted diaryl, unsubstituted $C_3$-$C_6$ cyclic, or unsubstituted heterocyclic. Still more preferably, $R_1$, $R_2$, $R_3$, $R_4$, $R_5$, $R_6$, $R_7$, $R_8$, and $R_9$ are each independently hydrogen, unsubstituted $C_1$-$C_6$ alkyl, unsubstituted $C_1$-$C_6$ alkenyl, unsubstituted $C_1$-$C_6$ alkynyl, unsubstituted phenyl, unsubstituted aryl, unsubstituted heteroaryl, unsubstituted $C_1$-$C_6$ alkoxy, unsubstituted phenoxy, unsubstituted aroxy, unsubstituted $C_3$-$C_6$ cyclic, or unsubstituted heterocyclic. Even more preferably, $R_1$ is hydrogen and $R_2$, $R_3$, $R_4$, $R_5$, $R_6$, $R_7$, $R_8$, and $R_9$ are each independently hydrogen, unsubstituted $C_1$-$C_6$ alkyl, unsubstituted $C_1$-$C_6$ alkenyl, unsubstituted $C_1$-$C_6$ alkynyl, unsubstituted phenyl, unsubstituted aryl, unsubstituted heteroaryl, unsubstituted $C_1$-$C_6$ alkoxy, unsubstituted phenoxy, unsubstituted aroxy, unsubstituted $C_3$-$C_6$ cyclic, or unsubstituted heterocyclic.

In some embodiments of complexes of Formula I-A: M is Au, Pt, or Pd; $R_1$ is hydrogen or phenyl; $R_2$ and $R_3$ are each hydrogen or together are —CH—CH—CH—CH—; $R_4$, $R_5$, $R_7$, and $R_8$ are each hydrogen; $R_6$ and $R_9$ are each independently selected from —$CH_3$, —$C_2H_5$, —$C_3H_7$, —$C_4H_9$, —$C_5H_{11}$, $C_6H_{13}$, benzyl, (2-hydroxy) ethyl, phenyl, naphthalen-2-ylmethyl, or (2-phenyl) ethyl; n is +1 or +2; and X, Y, Z are each independently carbon or nitrogen.

In some embodiments of complexes of Formula I-A: M is Platinum; $R_1$, $R_2$, $R_3$, $R_4$, $R_5$, $R_7$, and $R_8$ are each hydrogen; $R_6$ is benzyl; $R_9$ is —$C_4H_9$; n is +1; $yA^b$ is $CF_3SO_4^-$; X is carbon; and Y and Z are each nitrogen.

In some embodiments of complexes of Formula I-A, M is Platinum. In some embodiments of complexes of Formula I-A, $R_1$, $R_2$, $R_3$, $R_4$, $R_5$, $R_7$, and $R_8$ are each hydrogen. In some embodiments of complexes of Formula I-A n is +1. In some embodiments of complexes of Formula I-A, $yA^b$ is $CF_3SO_4^-$. In some embodiments of complexes of Formula I-A, X is carbon. In some embodiments of Formula I-A, Y and Z are each nitrogen. In some embodiments of complexes of Formula I-A, $R_6$ is benzyl. In some embodiments of complexes of Formula I-A, $R_9$ is —$C_4H_9$.

In some embodiments, the complex can have a structure according to Formula II-A, or a pharmaceutically acceptable salt thereof:

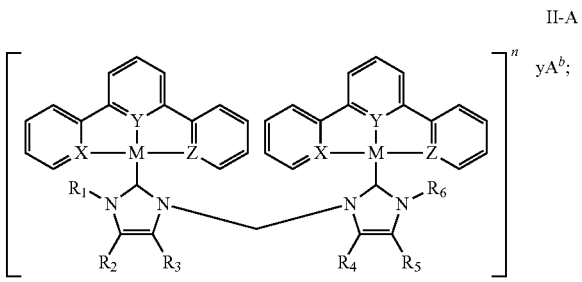

II-A where $R_1$, $R_2$, $R_3$, $R_4$, $R_5$, and $R_6$ are each independently hydrogen, substituted or unsubstituted $C_1$-$C_6$ alkyl, substituted or unsubstituted $C_1$-$C_6$ alkenyl, substituted or unsubstituted $C_1$-$C_6$ alkynyl, substituted or unsubstituted phenyl, substituted or unsubstituted aryl, substituted or unsubstituted heteroaryl, substituted or unsubstituted $C_1$-$C_6$ alkoxy, substituted or unsubstituted phenoxy, substituted or unsubstituted aroxy, substituted or unsubstituted $C_1$-$C_6$ alkylthio, substituted or unsubstituted phenylthio, substituted or unsubstituted arylthio, substituted or unsubstituted $C_1$-$C_6$ carbonyl, substituted or unsubstituted $C_1$-$C_6$ carboxyl, substituted or unsubstituted $C_1$-$C_6$ amino, substituted or unsubstituted $C_1$-$C_6$ amido, substituted or unsubstituted $C_1$-$C_6$ sulfonyl, $C_1$-$C_6$ sulfonic acid, substituted or unsubstituted $C_1$-$C_6$ phosphoryl, substituted or unsubstituted $C_1$-$C_6$ phosphonyl, substituted or unsubstituted diyaryl, substituted or unsubstituted $C_3$-$C_6$ cyclic, or substituted or unsubstituted heterocyclic; and where optionally and independently the pairs $R_1$ and $R_2$, $R_2$ and $R_3$, $R_4$ and $R_5$, and $R_5$ and $R_6$ together are $^-(CH_2)_{3-5}$.

Preferably, $R_1$, $R_2$, $R_3$, $R_4$, $R_5$, and $R_6$ are each independently hydrogen, substituted or unsubstituted $C_1$-$C_6$ alkyl, substituted or unsubstituted $C_1$-$C_6$ alkenyl, substituted or unsubstituted $C_1$-$C_6$ alkynyl, substituted or unsubstituted phenyl, substituted or unsubstituted aryl, substituted or unsubstituted heteroaryl, substituted or unsubstituted $C_1$-$C_6$ alkoxy, substituted or unsubstituted phenoxy, substituted or unsubstituted aroxy, substituted or unsubstituted diyaryl, substituted or unsubstituted $C_3$-$C_6$ cyclic, or substituted or unsubstituted heterocyclic. More preferably, $R_1$, $R_2$, $R_3$, $R_4$, $R_5$, and $R_6$ are each independently hydrogen, unsubstituted $C_1$-$C_6$ alkyl, unsubstituted $C_1$-$C_6$ alkenyl, unsubstituted $C_1$-$C_6$ alkynyl, unsubstituted phenyl, unsubstituted aryl, unsubstituted heteroaryl, unsubstituted $C_1$-$C_6$ alkoxy, unsubstituted phenoxy, unsubstituted aroxy, unsubstituted diyaryl, unsubstituted $C_3$-$C_6$ cyclic, or unsubstituted heterocyclic. Still more preferably, $R_1$, $R_2$, $R_3$, $R_4$, $R_5$, and $R_6$ are each independently hydrogen, unsubstituted $C_1$-$C_6$ alkyl, unsubstituted $C_1$-$C_6$ alkenyl, unsubstituted $C_1$-$C_6$ alkynyl, unsubstituted phenyl, unsubstituted aryl, unsubstituted heteroaryl, unsubstituted $C_1$-$C_6$ alkoxy, unsubstituted phenoxy, unsubstituted aroxy, unsubstituted $C_3$-$C_6$ cyclic, or unsubstituted heterocyclic. Even more preferably, $R_1$, $R_2$, $R_3$, $R_4$, $R_5$, and $R_6$ are each independently hydrogen, unsubstituted phenyl, unsubstituted aryl, unsubstituted heteroaryl, unsubstituted phenoxy, unsubstituted aroxy, unsubstituted $C_3$-$C_6$ cyclic, or unsubstituted heterocyclic.

In some embodiments of complexes of Formula II-A: each M is independently selected from Au, Pt, or Pd; $R_2$, $R_3$, $R_4$, and $R_5$ are each hydrogen; $R_1$ and $R_6$ are each independently selected from —$CH_3$, benzyl, or naphthalen-2-ylmethyl; n is +1 or +2; y is equal to the absolute value of n/b; and each X, Y, and Z are independently carbon or nitrogen.

In some embodiments of complexes of Formula II-A: each M is Platinum; $R_2$, $R_3$, $R_4$, and $R_5$ are each hydrogen; $R_1$ and $R_6$ are each benzyl; n is +2; yAb is 2 $CF_3SO_3^-$; each X is carbon, and each Y and Z is nitrogen.

In some embodiments of complexes of Formula II-A, each M is Platinum. In some embodiments of complexes of Formula II-A, $R_2$, $R_3$, $R_4$, and $R_5$ are each hydrogen. In some embodiments of complexes of Formula II-A, n is +2. In some embodiments of complexes of Formula II-A, $yA^b$ is 2 $CF_3SO_3^-$. In some embodiments of complexes of Formula II-A, each X is carbon. In some embodiments of complexes of Formula II-A, each Y and Z is nitrogen. In some embodiments of complexes of Formula II-A, $R_1$ and $R_6$ are each benzyl.

In some embodiments, the complex can have a structure according to Formula II-B, or a pharmaceutically acceptable salt thereof:

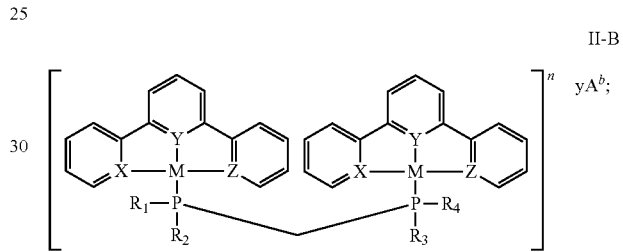

II-B where $R_1$, $R_2$, $R_3$, and $R_4$ are each independently hydrogen, substituted or unsubstituted $C_1$-$C_6$ alkyl, substituted or unsubstituted $C_1$-$C_6$ alkenyl, substituted or unsubstituted $C_1$-$C_6$ alkynyl, substituted or unsubstituted phenyl, substituted or unsubstituted aryl, substituted or unsubstituted heteroaryl, substituted or unsubstituted $C_1$-$C_6$ alkoxy, substituted or unsubstituted phenoxy, substituted or unsubstituted aroxy, substituted or unsubstituted $C_1$-$C_6$ alkylthio, substituted or unsubstituted phenylthio, substituted or unsubstituted arylthio, substituted or unsubstituted $C_1$-$C_6$ carbonyl, substituted or unsubstituted $C_1$-$C_6$ carboxyl, substituted or unsubstituted $C_1$-$C_6$ amino, substituted or unsubstituted $C_1$-$C_6$ amido, substituted or unsubstituted $C_1$-$C_6$ sulfonyl, $C_1$-$C_6$ sulfonic acid, substituted or unsubstituted $C_1$-$C_6$ phosphoryl, substituted or unsubstituted $C_1$-$C_6$ phosphonyl, substituted or unsubstituted diyaryl, substituted or unsubstituted $C_3$-$C_6$ cyclic, or substituted or unsubstituted heterocyclic.

Preferably, $R_1$, $R_2$, $R_3$, and $R_4$ are each independently hydrogen, substituted or unsubstituted $C_1$-$C_6$ alkyl, substituted or unsubstituted $C_1$-$C_6$ alkenyl, substituted or unsubstituted $C_1$-$C_6$ alkynyl, substituted or unsubstituted phenyl, substituted or unsubstituted aryl, substituted or unsubstituted heteroaryl, substituted or unsubstituted $C_1$-$C_6$ alkoxy, substituted or unsubstituted phenoxy, substituted or unsubstituted aroxy, substituted or unsubstituted diyaryl, substituted or unsubstituted $C_3$-$C_6$ cyclic, or substituted or unsubstituted heterocyclic. More preferably, $R_1$, $R_2$, $R_3$, and $R_4$ are each independently hydrogen, unsubstituted $C_1$-$C_6$ alkyl, unsubstituted $C_1$-$C_6$ alkenyl, unsubstituted $C_1$-$C_6$ alkynyl, unsubstituted phenyl, unsubstituted aryl, unsubstituted heteroaryl, unsubstituted $C_1$-$C_6$ alkoxy, unsubstituted phenoxy, unsubstituted aroxy, unsubstituted diyaryl, unsubstituted $C_3$-$C_6$ cyclic, or unsubstituted heterocyclic. Still more preferably, $R_1$, $R_2$, $R_3$, and $R_4$ are each independently unsubstituted $C_1$-$C_6$ alkyl, unsubstituted $C_1$-$C_6$ alkenyl, unsubstituted $C_1$-$C_6$ alkynyl, unsubstituted phenyl, unsubstituted aryl, unsubstituted heteroaryl, unsubstituted $C_1$-$C_6$ alkoxy, unsubstituted phenoxy, unsubstituted aroxy, unsubstituted $C_3$-$C_6$ cyclic, or unsubstituted heterocyclic. Even more preferably, $R_1$, $R_2$, $R_3$, and $R_4$ are each independently unsubstituted phenyl, unsubstituted aryl, unsubstituted heteroaryl, unsubstituted phenoxy, unsubstituted aroxy, unsubstituted $C_3$-$C_6$ cyclic, or unsubstituted heterocyclic.

In some embodiments of complexes of Formula II-B: each M is independently selected from Au, Pt or Pd; $R_1$, $R_2$, $R_3$, and $R_4$ are each independently selected from phenyl or $C_6H_6$; n is +1 or +2; y is equal to the absolute value of n/b; and each X, Y, and Z are independently carbon or nitrogen.

In some embodiments of complexes of Formula II-B: each M is Platinum; $R_1$, $R_2$, $R_3$, and $R_4$ are each phenyl; n is +2; yAb is 2 $CF_3SO_3^-$; each X is carbon, and each Y and Z is nitrogen.

In some embodiments of complexes of Formula II-B, each M is Platinum. In some embodiments of complexes of Formula II-B, $R_1$, $R_2$, $R_3$, and $R_4$ are each phenyl. In some embodiments of complexes of Formula II-B, n is +2. In some embodiments of complexes of Formula II-B, $yA^b$ is 2 $CF_3SO_3^-$. In some embodiments of complexes of Formula II-B, each X is carbon. In some embodiments of complexes of Formula II-B, each Y and Z is nitrogen.

In some embodiments of the complexes, each M is, independently, platinum(II) (Pt(II) or $Pt^{2+}$), palladium(II) (Pd(II) or $Pd^{2+}$), or gold(III) (Au(III) or $Au^{3+}$).

In some embodiments of complexes of Formula I, M is coordinated to an anionic or di-anionic 1,3-di(pyridin-2-yl)benzene (NACAN) ligand, 2,6-diphenylpyridine (CANAC) ligand, 6-phenyl-2,2'-bipyridine (C^N^N) ligand, 6-(naphthalen-2-yl)-2,2'-bipyridine ligand, 4,6-diphenyl-2,2'-bipyridine ligand, or a N-heterocyclic carbene ligand.

In some embodiments of complexes of Formula II, the two M are each coordinated to an anionic 6-phenyl-2,2'-bipyridine (C^N^N) ligand and are connected with bis-N-heterocyclic carbene or diphosphine ligand.

It has been found that square-planar metal complexes with different N-heterocyclic carbene (NHC) or di-phosphine ligand have a good selectivity toward mismatched DNA sites. The specificity of the complexes were attributed to the suitable size and functionality of the ligand. The significant differences in emission enhancement of complexes toward matched and mismatched DNA make the complexes useful as probes in targeting mismatched sites in DMA.

Additional advantages of the disclosed method and complexes will be set forth in part in the description which follows, and in part will be understood from the description, or may be learned by practice of the disclosed method and complexes. The advantages of the disclosed method and complexes will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and complexes and together with the description, serve to explain the principles of the disclosed method and complexes.

The patent or application file contains at least one drawing executed in color. Copies of this patent or patent application publication, with color drawing(s), will be provided by the Office upon request and payment of the necessary fee.

FIG. 20 (b) is a plot of the fold of increased emission vs. 1 g (mutation rate); a linear fit is shown.

DETAILED DESCRIPTION OF THE INVENTION

Figure 1A:
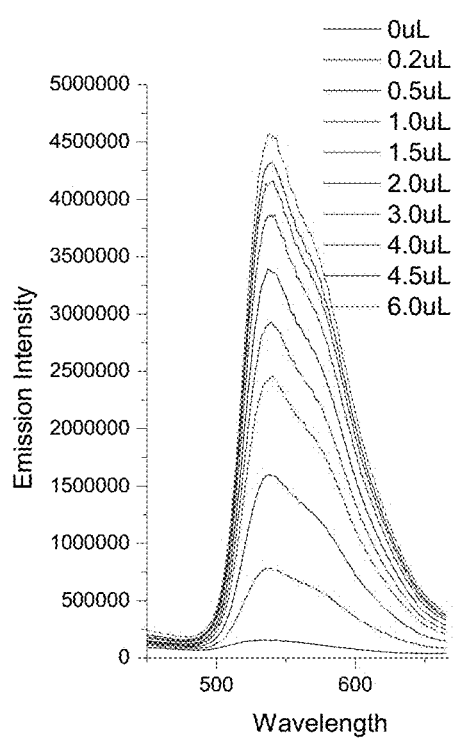
FIGS. 1A and 1B are graphs showing the emission spectra of complex 5 (5 μM) in an aqueous buffer solution (50 mM NaCl, 2 mM Tris, pH 7.5) after binding to different concentrations of CC mismatched DNA (left) and well-matched DNA (right).

The disclosed method and complexes may be understood more readily by reference to the following detailed description of particular embodiments and the examples included therein and to the figures and their previous and following description. Disclosed are methods of using $d^8$ square planar metal complexes containing tridentate π-conjugated ligands and ancillary ligand of N-heterocyclic carbene or di-phosphine ligand to target mismatched DNA. Targeting of mismatched DNA is revealed by monitoring the differences in emission enhancement of metal complexes toward mismatched DNA and matched DNA; or the gradually heat release from isothermal titration calorimetry (ITC) when complexes bind toward mismatch DNA; or the significant increase in melting temperature of the mismatched DNA after adding complexes.

In order to target DNA and/or single nucleotide polymorphism (SNP) with superior high selectivity, it is anticipated that the metal complexes should be of the right geometry as well as size to fit into the mismatched sites but not into the well-matched DNA.

In view of the high binding affinity of $d^8$ square planar complexes with DNA, it is conceive that the binding affinity of the complexes with matched DNA will decrease if bulky ligand out of the plane are incorporated; instead, the binding with mismatched DNA will remain unchanged/become stronger owing to the larger space at the mismatched site and possible groove binding by the introduced ligand. In this regard, a series of mononuclear and dinuclear $d^8$ square-planar metal complexes containing π-conjugated ligands including C-deprotonated C^N^N (HC^N^N=6-phenyl-2,2'-bipyridineand) and bulky ancillary ligands such as N-heterocyclic carbene (NHC) and phosphine have been developed. Their spectroscopic properties in the absence or presence of different types of DNA have been studied thoroughly. Excellent selectivity toward mismatched DNA sites has been demonstrated, which is attributed to the judicious choice of the structural and chemical properties of the metal complexes. These $d^8$ metal complexes are also potential anti-cancer agents due to the binding with mismatched DNA.

Definitions

As used herein, the term "tridentate ligand," in the context of the disclosed complexes, refers to an anionic or di-anionic ligand. Examples include anionic or di-anionic 1,3-di(pyridin-2-yl)benzene (N^CH^N), 2,6-diphenylpyridine (HC^N^CH), 6-phenyl-2,2'-bipyridine (HC^N^N) and its analogue 6-(naphthalen-2-yl)-2,2'-bipyridine, 4,6-diphenyl-2,2'-bipyridine ligand.

As used herein, the term "N-heterocyclic carbene," in the context of the disclosed complexes, refers to a ligand having the structure:

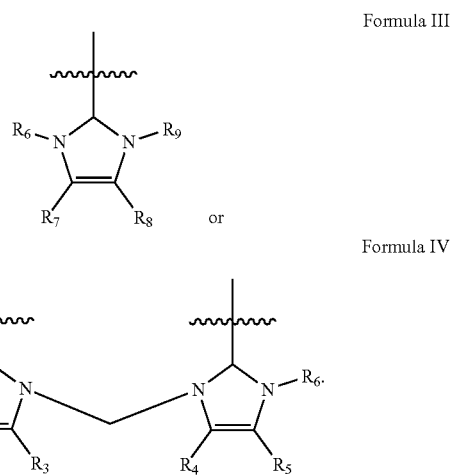

Formula III

Formula IV

In Formula III, $R_6$, $R_7$, $R_8$, and $R_9$ are each independently hydrogen, substituted or unsubstituted $C_1$-$C_6$ alkyl, substituted or unsubstituted $C_1$-$C_6$ alkenyl, substituted or unsubstituted $C_1$-$C_6$ alkynyl, substituted or unsubstituted phenyl, substituted or unsubstituted aryl, substituted or unsubstituted heteroaryl, substituted or unsubstituted $C_1$-$C_6$ alkoxy, substituted or unsubstituted phenoxy, substituted or unsubstituted aroxy, substituted or unsubstituted $C_1$-$C_6$ alkylthio, substituted or unsubstituted phenylthio, substituted or unsubstituted arylthio, substituted or unsubstituted $C_1$-$C_6$ carbonyl, substituted or unsubstituted $C_1$-$C_6$ carboxyl, substituted or unsubstituted $C_1$-$C_6$ amino, substituted or unsubstituted $C_1$-$C_6$ amido, substituted or unsubstituted $C_1$-$C_6$ sulfonyl, $C_1$-$C_6$ sulfonic acid, substituted or unsubstituted $C_1$-$C_6$ phosphoryl, substituted or unsubstituted $C_1$-$C_6$ phosphonyl, substituted or unsubstituted diyaryl, substituted or unsubstituted $C_3$-$C_6$ cyclic, or substituted or unsubstituted heterocyclic; and where optionally and independently the pairs $R_2$ and $R_3$, $R_4$ and $R_5$, $R_6$ and $R_7$, $R_7$ and $R_8$, and $R_8$ and $R_9$ together are —$(CH_2)_{3-5}$—.

In Formula IV, $R_1$, $R_2$, $R_3$, $R_4$, $R_5$, and $R_6$ are each independently hydrogen, substituted or unsubstituted $C_1$-$C_6$ alkyl, substituted or unsubstituted $C_1$-$C_6$ alkenyl, substituted or unsubstituted $C_1$-$C_6$ alkynyl, substituted or unsubstituted phenyl, substituted or unsubstituted aryl, substituted or unsubstituted heteroaryl, substituted or unsubstituted $C_1$-$C_6$ alkoxy, substituted or unsubstituted phenoxy, substituted or unsubstituted aroxy, substituted or unsubstituted $C_1$-$C_6$ alkylthio, substituted or unsubstituted phenylthio, substituted or unsubstituted arylthio, substituted or unsubstituted $C_1$-$C_6$ carbonyl, substituted or unsubstituted $C_1$-$C_6$ carboxyl, substituted or unsubstituted $C_1$-$C_6$ amino, substituted or unsubstituted $C_1$-$C_6$ amido, substituted or unsubstituted $C_1$-$C_6$ sulfonyl, $C_1$-$C_6$ sulfonic acid, substituted or unsubstituted $C_1$-$C_6$ phosphoryl, substituted or unsubstituted $C_1$-$C_6$ phosphonyl, substituted or unsubstituted diyaryl, substituted or unsubstituted $C_3$-$C_6$ cyclic, or substituted or unsubstituted heterocyclic; and where optionally and independently the pairs $R_1$ and $R_2$, $R_2$ and $R_3$, $R_4$ and $R_5$, and $R_5$ and $R_6$ together are —$(CH_2)_{3-5}$—.

In some embodiments of Formula III, $R_6$ and $R_9$ are each independently selected from a —$CH_3$, —$C_2H_5$, —$C_3H_7$, —$C_4H_9$, —$C_5H_{11}$, —$C_6H_{13}$, benzyl, (1-hydroxy) ethyl, phenyl, naphthalen-2-ylmethyl, (phenyl) ethyl; and $R_7$ and $R_8$, are each hydrogen.

In some embodiments of Formula IV, $R_2$, $R_3$, $R_4$, $R_5$ are each independently selected from —H; and $R_1$, $R_6$ are each independently selected from —CH3, benzyl, naphthalen-2-ylmethyl.

As used herein, the term "phosphine," in the context of the disclosed complexes, refers to a ligand having the structure:

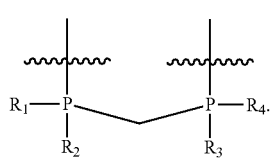

Formula V

In Formula V, $R_1$, $R_2$, $R_3$, and $R_4$ are each independently hydrogen, substituted or unsubstituted $C_1$-$C_6$ alkyl, substituted or unsubstituted $C_1$-$C_6$ alkenyl, substituted or unsubstituted $C_1$-$C_6$ alkynyl, substituted or unsubstituted phenyl, substituted or unsubstituted aryl, substituted or unsubstituted heteroaryl, substituted or unsubstituted $C_1$-$C_6$ alkoxy, substituted or unsubstituted phenoxy, substituted or unsubstituted aroxy, substituted or unsubstituted $C_1$-$C_6$ alkylthio, substituted or unsubstituted phenylthio, substituted or unsubstituted arylthio, substituted or unsubstituted $C_1$-$C_6$ carbonyl, substituted or unsubstituted $C_1$-$C_6$ carboxyl, substituted or unsubstituted $C_1$-$C_6$ amino, substituted or unsubstituted $C_1$-$C_6$ amido, substituted or unsubstituted $C_1$-$C_6$ sulfonyl, $C_1$-$C_6$ sulfonic acid, substituted or unsubstituted $C_1$-$C_6$ phosphoryl, substituted or unsubstituted $C_1$-$C_6$ phosphonyl, substituted or unsubstituted diyaryl, substituted or unsubstituted $C_3$-$C_6$ cyclic, or substituted or unsubstituted heterocyclic.

In some forms of Formula V, $R_1$,$R_2$,$R_3$,$R_4$ are each independently selected from phenyl or $C_6H_6$.

As used herein, the term "acceptable salt," in the context of the disclosed complexes, includes salts formed from the charged Pt(II)-NHC , Pd (II)-NHC and Au(III)-NHC complexes and their counter-anion(s).

As used herein, the term "counter-anion," in the context of the disclosed complexes, refers to an ion associated with a positively charged Pt(II)-NHC, Pd (II)-NHC and Au(III)-NHC complexes.

As used herein, the term "di-nuclear M(II/III) complexes with —NHC ligand," in the context of the disclosed complexes, refers to a molecule with two metal (II/III) ions connected by a N-heterocyclic carbene ligand.

As used herein, the term "di-nuclear M(II/III) complexes with phosphine ligand," in the context of the disclosed complexes, refers to a molecule with two metal (II/III) ions connected by di-phosphine ligand. In addition, each M (II) ion also connected to a tridentate ligand.

The term "alkyl group" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is an alkyl group containing from one to six carbon atoms.

The term "alkoxy" as used herein is an alkyl group bound through a single, terminal ether linkage; that is, an "alkoxy" group may be defined as -OR where R is alkyl as defined above. A "lower alkoxy" group is an alkoxy group containing from one to six carbon atoms.

The term "alkenyl group" as used herein is a hydrocarbon group of from 2 to 24 carbon atoms and structural formula containing at least one carbon-carbon double bond. Asymmetric structures such as (AB)C=C(CD) are intended to include both the E and Z isomers. This may be presumed in structural formulae herein wherein an asymmetric alkene is present, or it may be explicitly indicated by the bond symbol C.

The term "alkynyl group" as used herein is a hydrocarbon group of 2 to 24 carbon atoms and a structural formula containing at least one carbon-carbon triple bond.

The term "aryl group" as used herein is any carbon-based aromatic group including, but not limited to, benzene, naphthalene, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorus. The aryl group can be substituted or unsubstituted. The aryl group can be substituted with one or more groups including, but not limited to, alkyl, alkynyl, alkenyl, aryl, halide, nitro, amino, ester, ketone, aldehyde, hydroxy, carboxylic acid, or alkoxy.

The term "cycloalkyl group" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl group" is a cycloalkyl group as defined above where at least one of the carbon atoms of the ring is substituted with a heteroatom such as, but not limited to, nitrogen, oxygen, sulphur, or phosphorus.

The term "aralkyl" as used herein is an aryl group having an alkyl, alkynyl, or alkenyl group as defined above attached to the aromatic group. An example of an aralkyl group is a benzyl group.

The term "hydroxyalkyl group" as used herein is an alkyl, alkenyl, alkynyl, aryl, aralkyl, cycloalkyl, halogenated alkyl, or heterocycloalkyl group described above that has at least one hydrogen atom substituted with a hydroxyl group.

The term "alkoxyalkyl group" is defined as an alkyl, alkenyl, alkynyl, aryl, aralkyl, cycloalkyl, halogenated alkyl, or heterocycloalkyl group described above that has at least one hydrogen atom substituted with an alkoxy group described above.

The term "ester" as used herein is represented by the formula —C(O)OA, where A can be an alkyl, halogenated alkyl, alkenyl, alkynyl, aryl, heteroaryl, cycloalkyl, cycloalkenyl, heterocycloalkyl, or heterocycloalkenyl group described above.

The term "carbonate group" as used herein is represented by the formula —OC(O)OR, where R can be hydrogen, an alkyl, alkenyl, alkynyl, aryl, aralkyl, cycloalkyl, halogenated alkyl, or heterocycloalkyl group described elsewhere herein.

The term "carboxylic acid" as used herein is represented by the formula —C(O)OH.

The term "aldehyde" as used herein is represented by the formula —C(O)H.

The term "keto group" as used herein is represented by the formula —C(O)R, where R is an alkyl, alkenyl, alkynyl, aryl, aralkyl, cycloalkyl, halogenated alkyl, or heterocycloalkyl group described above.

The term "carbonyl group" as used herein is represented by the formula C=O.

The term "ether" as used herein is represented by the formula $AOA^1$, where A and $A^1$ can be, independently, an alkyl, halogenated alkyl, alkenyl, alkynyl, aryl, heteroaryl, cycloalkyl, cycloalkenyl, heterocycloalkyl, or heterocycloalkenyl group described above.

References herein to parts by weight, of a particular element or component in a composition, complex, or article, denotes the weight relationship between the element or component and any other elements or components in the composition, complex, or article for which a part by weight is expressed. Thus, in a complex containing 2 parts by weight of component X and 5 parts by weight component Y, X and Y are present at a weight ratio of 2:5, and are present in such ratio regardless of whether additional components are contained in the complex.

A weight percent of a component, unless specifically stated to the contrary, is based on the total weight of the formulation, complex, or composition in which the component is included.

A residue of a chemical species, as used herein, refers to the moiety that is the resulting product of the chemical species in a particular reaction scheme or subsequent formulation or chemical product, regardless of whether the moiety is actually obtained from the chemical species. Thus, an phenyl residue in a polyaryl compound refers to one or more $C_6H_6$ units in the polyaryl, regardless of whether phenyl was used to prepare the polyaryl.

Variables such as $R_1$, $R_2$, $R_3$, $R_4$, $R_5$, $R_6$, $R_7$, $R_8$, $R_9$, M, X, Y, Z, y, A, b, and n used throughout the application are the same variables as previously defined unless stated to the contrary. Some variables, such as $R_1$, $R_2$, $R_3$, $R_4$, $R_5$, and $R_6$ can vary depending on which of the disclosed Formulas is involved.

The term "hit" refers to a test complex that shows desired properties in an assay. The term "test complex" refers to a complex to be tested by one or more screening method(s) as putatively targeting mismatched DNA. A test complex can be any $d^8$ square planar metal complex as disclosed herein. Usually, various predetermined concentrations of test complexes are used for screening, such as 0.01 micromolar, 1 micromolar and 10 micromolar. Test complex controls can include the measurement of a signal in the absence of the test complex or comparison to a complex known to selectively target mismatched DNA.

The terms "high," "higher," "increases," "elevates," or "elevation" refer to increases above basal levels, e.g., as compared to a control. The terms "low," "lower," "reduces," or "reduction" refer to decreases below basal levels, e.g., as compared to a control.

The term "monitoring" as used herein refers to any method in the art by which an activity can be measured.

The term "providing" as used herein refers to any means of adding a complex or molecule to something known in the art. Examples of providing can include the use of pipettes, pipettemen, syringes, needles, tubing, guns, etc. This can be manual or automated. It can include transfection by any mean or any other means of providing nucleic acids to dishes, cells, tissue, cell-free systems and can be in vitro or in vivo.

The term "in need of treatment" as used herein refers to a judgment made by a caregiver (e.g. physician, nurse, nurse practitioner, or individual in the case of humans; veterinarian in the case of animals, including non-human mammals) that a subject requires or will benefit from treatment. This judgment is made based on a variety of factors that are in the realm of a care giver's expertise, but that include the knowledge that the subject is ill, or will be ill, as the result of a condition that is detectable by the complexes of the invention.

As used herein, "subject" includes, but is not limited to, animals, plants, bacteria, viruses, parasites and any other organism or entity. The subject can be a vertebrate, more specifically a mammal (e.g., a human, horse, pig, rabbit, dog, sheep, goat, non-human primate, cow, cat, guinea pig or rodent), a fish, a bird or a reptile or an amphibian. The subject can be an invertebrate, more specifically an arthropod (e.g., insects and crustaceans). The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

By "treatment" and "treating" is meant the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. It is understood that treatment, while intended to cure, ameliorate, stabilize, or prevent a disease, pathological condition, or disorder, need not actually result in the cure, ameliorization, stabilization or prevention. The effects of treatment can be measured or assessed as described herein and as known in the art as is suitable for the disease, pathological condition, or disorder involved. Such measurements and assessments can be made in qualitative and/or quantitiative terms. Thus, for example, characteristics or features of a disease, pathological condition, or disorder and/or symptoms of a disease, pathological condition, or disorder can be reduced to any effect or to any amount.

A cell can be in vitro. Alternatively, a cell can be in vivo and can be found in a subject. A "cell" can be a cell from any organism including, but not limited to, a bacterium.

It must be noted that as used herein and in the appended claims, the singular forms "a," "an," and "the" include plural reference unless the context clearly dictates otherwise. Thus, for example, reference to "a complex" includes a plurality of such complexes, reference to "the complex" is a reference to one or more complexes.

Throughout the description and claims of this specification, the word "comprise" and variations of the word, such as "comprising" and "comprises," means "including but not limited to," and is not intended to exclude, for example, other additives, components, integers or steps. "Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value.

When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and complexes belong. Although any methods and materials similar or equivalent to those described herein can be used in the practice or testing of the present method and complexes, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Although the description of materials, compositions, complexes, components, steps, techniques, etc. may include numerous options and alternatives, this should not be construed as, and is not an admission that, such options and alternatives are equivalent to each other or, in particular, are obvious alternatives. Thus, for example, a list of different complexes does not indicate that the listed complexes are obvious one to the other, nor is it an admission of equivalence or obviousness.

Disclosed are materials, compositions, complexes, and components that can be used for, can be used in conjunction with, can be used in preparation for, or are products of the disclosed method and complexes. These and other materials are disclosed herein, and it is understood that when combinations, subsets, interactions, groups, etc. of these materials are disclosed that while specific reference of each various individual and collective combinations and permutation of these complexes may not be explicitly disclosed, each is specifically contemplated and described herein. For example, if a complex is disclosed and discussed and a number of modifications that can be made to a number of molecules including the complex are discussed, each and every combination and permutation of complex and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. Further, each of the materials, compositions, complexes, components, etc. contemplated and disclosed as above can also be specifically and independently included or excluded from any group, subgroup, list, set, etc. of such materials. These concepts apply to all aspects of this application including, but not limited to, steps in methods of making and using the disclosed complexes. Thus, if there are a variety of additional steps that can be performed it is understood that each of these additional steps can be performed with any specific embodiment or combination of embodiments of the disclosed methods, and that each such combination is specifically contemplated and should be considered disclosed.

Every complex disclosed herein is intended to be and should be considered to be specifically disclosed herein. Further, every *subgroup* that can be identified within this disclosure is intended to be and should be considered to be specifically disclosed herein. As a result, it is specifically contemplated that any complex, or subgroup of complexes can be either specifically included for or excluded from use or included in or excluded from a list of complexes.

It is to be understood that the disclosed method and complexes are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

Materials

A. Complexes

In one aspect described herein are complexes having the structure of Formula I, or the pharmaceutically acceptable salt or ester thereof:

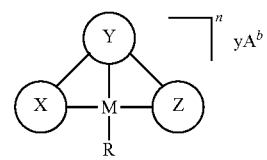

I where X^Y^Z is a tridentate π-conjugated ligand; X, Y, and Z are each, independently, carbon or nitrogen; R is a N-heterocyclic carbene ligand or a phosphine ligand; M is a $d^8$ metal atom; n is the charge of the complex; A is the counter-ion for the complex; b is the charge of the counter-ion; and y is the absolute value of n/b.

In some embodiments of complexes of Formula I, M is coordinated to an anionic or di-anionic 1,3-di(pyridin-2-yl) benzene (NACAN) ligand, 2,6-diphenylpyridine (CANAC) ligand, 6-phenyl-2,2'-bipyridine (C^N^N) ligand, 6-(naphthalen-2-yl)-2,2'-bipyridine ligand, 4,6-diphenyl-2,2'-bipyridine ligand, or a N-heterocyclic carbene ligand.

In some embodiments of complexes of Formula I, the $d^8$ metal atom can be platinum(II) (Pt(II) or $Pt^{2+}$), palladium(II) (Pd(II) or $Pd^{2+}$), gold(III) (Au(III) or $Au^{3+}$), silver (III) (Ag(III) of $Ag^{3+}$), copper(III) (Cu(III) or $Cu^{3+}$), nickel(II) (Ni(II) or $Ni^{2+}$), cobalt(I) (Co(I) or $Co^+$), rhodium(I) (Rh(I) or $Rh^+$), or iridium(I) (Ir(I) or $Ir^+$).

In one aspect described herein are complexes having the Formula I-A, or the pharmaceutically acceptable salt or ester thereof:

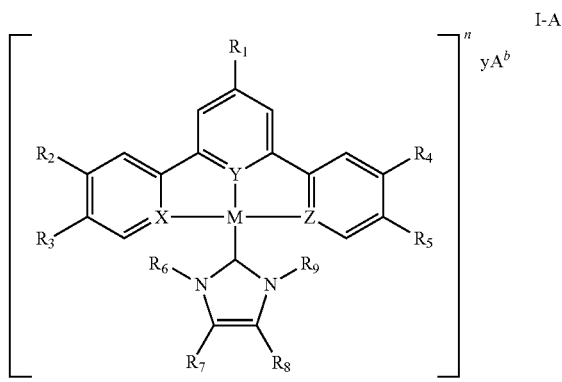

where $R_1$, $R_2$, $R_3$, $R_4$, $R_5$, $R_6$, $R_7$, $R_8$, and $R_9$ are each independently hydrogen, substituted or unsubstituted $C_1$-$C_6$ alkyl, substituted or unsubstituted $C_1$-$C_6$ alkenyl, substituted or unsubstituted $C_1$-$C_6$ alkynyl, substituted or unsubstituted phenyl, substituted or unsubstituted aryl, substituted or unsubstituted heteroaryl, substituted or unsubstituted $C_1$-$C_6$ alkoxy, substituted or unsubstituted phenoxy, substituted or unsubstituted aroxy, substituted or unsubstituted $C_1$-$C_6$ alkylthio, substituted or unsubstituted phenylthio, substituted or unsubstituted arylthio, substituted or unsubstituted $C_1$-$C_6$ carbonyl, substituted or unsubstituted $C_1$-$C_6$ carboxyl, substituted or unsubstituted $C_1$-$C_6$ amino, substituted or unsubstituted $C_1$-$C_6$ amido, substituted or unsubstituted $C_1$-$C_6$ sulfonyl, $C_1$-$C_6$ sulfonic acid, substituted or unsubstituted $C_1$-$C_6$ phosphoryl, substituted or unsubstituted $C_1$-$C_6$ phosphonyl, substituted or unsubstituted diyaryl, substituted or unsubstituted $C_3$-$C_6$ cyclic, or substituted or unsubstituted heterocyclic; and where optionally and independently the pairs $R_2$ and $R_3$, $R_4$ and $R_5$, $R_6$ and $R_7$, $R_7$ and $R_8$, and $R_8$ and $R_9$ together are —(CH$_2$)$_{3-5}$—.

Preferably, $R_1$, $R_2$, $R_3$, $R_4$, $R_5$, $R_6$, $R_7$, $R_8$, and $R_9$ are each independently hydrogen, substituted or unsubstituted $C_1$-$C_6$ alkyl, substituted or unsubstituted $C_1$-$C_6$ alkenyl, substituted or unsubstituted $C_1$-$C_6$ alkynyl, substituted or unsubstituted phenyl, substituted or unsubstituted aryl, substituted or unsubstituted heteroaryl, substituted or unsubstituted $C_1$-$C_6$ alkoxy, substituted or unsubstituted phenoxy, substituted or unsubstituted aroxy, substituted or unsubstituted diyaryl, substituted or unsubstituted $C_3$-$C_6$ cyclic, or substituted or unsubstituted heterocyclic. More preferably, $R_1$, $R_2$, $R_3$, $R_4$, $R_5$, $R_6$, $R_7$, $R_8$, and $R_9$ are each independently hydrogen, unsubstituted $C_1$-$C_6$ alkyl, unsubstituted $C_1$-$C_6$ alkenyl, unsubstituted $C_1$-$C_6$ alkynyl, unsubstituted phenyl, unsubstituted aryl, unsubstituted heteroaryl, unsubstituted $C_1$-$C_6$ alkoxy, unsubstituted phenoxy, unsubstituted aroxy, unsubstituted diyaryl, unsubstituted $C_3$-$C_6$ cyclic, or unsubstituted heterocyclic. Still more preferably, $R_1$, $R_2$, $R_3$, $R_4$, $R_5$, $R_6$, $R_7$, $R_8$, and $R_9$ are each independently hydrogen, unsubstituted $C_1$-$C_6$ alkyl, unsubstituted $C_1$-$C_6$ alkenyl, unsubstituted $C_1$-$C_6$ alkynyl, unsubstituted phenyl, unsubstituted aryl, unsubstituted heteroaryl, unsubstituted $C_1$-$C_6$ alkoxy, unsubstituted phenoxy, unsubstituted aroxy, unsubstituted $C_3$-$C_6$ cyclic, or unsubstituted heterocyclic. Even more preferably, $R_1$ is hydrogen and $R_2$, $R_3$, $R_4$, $R_5$, $R_6$, $R_7$, $R_8$, and $R_9$ are each independently hydrogen, unsubstituted $C_1$-$C_6$ alkyl, unsubstituted $C_1$-$C_6$ alkenyl, unsubstituted $C_1$-$C_6$ alkynyl, unsubstituted phenyl, unsubstituted aryl, unsubstituted heteroaryl, unsubstituted $C_1$-$C_6$ alkoxy, unsubstituted phenoxy, unsubstituted aroxy, unsubstituted $C_3$-$C_6$ cyclic, or unsubstituted heterocyclic.

In some embodiments of complexes of Formula I-A: M is Au, Pt, or Pd; $R_1$ is hydrogen or phenyl; $R_2$ and $R_3$ are each hydrogen or together are —CH—CH—CH—CH—; $R_4$, $R_5$, $R_7$, and $R_8$ are each hydrogen; $R_6$ and $R_9$ are each independently selected from —CH$_3$, —C$_2$H$_5$, —C$_3$H$_7$, —C$_4$H$_9$, —C$_5$H$_{11}$, C$_6$H$_{13}$, benzyl, (2-hydroxy) ethyl, phenyl, naphthalen-2-ylmethyl, or (2-phenyl) ethyl; n is +1 or +2; and X, Y, Z are each independently carbon or nitrogen.

In some embodiments of complexes of Formula I-A: M is Platinum; $R_1$, $R_2$, $R_3$, $R_4$, $R_5$, $R_7$, and $R_8$ are each hydrogen; $R_6$ is benzyl; $R_9$ is —C$_4$H$_9$; n is +1; $yA^b$ is $CF_3SO_4^-$; X is carbon; and Y and Z are each nitrogen.

In some embodiments of complexes of Formula I-A, M is Platinum. In some embodiments of complexes of Formula I-A, $R_1$, $R_2$, $R_3$, $R_4$, $R_5$, $R_7$, and $R_8$ are each hydrogen. In some embodiments of complexes of Formula I-A n is +1. In some embodiments of complexes of Formula I-A, $yA^b$ is $CF_3SO_4^-$. In some embodiments of complexes of Formula I-A, X is carbon. In some embodiments of complexes of Formula I-A, Y and Z are each nitrogen. In some embodiments of complexes of Formula I-A, $R_6$ is benzyl. In some embodiments of complexes of Formula I-A, $R_9$ is —C$_4$H$_9$.

In one aspect described herein are complexes having the structure of Formula II, or the pharmaceutically acceptable salt or ester thereof:

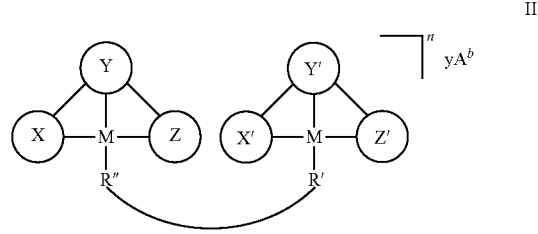

where X^Y^Z and X'^Y'^Z' are each, independently, a tridentate π-conjugated ligand; X, Y, Z, X', Y', and Z' are each, independently, carbon or nitrogen; R, R', and R" are each, independently, a N-heterocyclic carbene ligand or a phosphine ligand; each M is a $d^8$ metal atom; n is the charge of the complex; A is the counter-ion for the complex; b is the charge of the counter-ion; and y is the absolute value of n/b.

In some embodiments of complexes of Formula II, the $d^8$ metal atom can be platinum(II) (Pt(II) or $Pt^{2+}$), palladium(II) (Pd(II) or $Pd^{2+}$), gold(III) (Au(III) or $Au^{3+}$), silver (III) (Ag(III) of $Ag^{3+}$), copper(III) (Cu(III) or $Cu^{3+}$), nickel(II) (Ni(II) or $Ni^{2+}$), cobalt(I) (Co(I) or $Co^+$), rhodium(I) (Rh(I) or Rh), or iridium(I) (Ir(I) or $Ir^+$).

In some embodiments of complexes of Formula II, R'^R" is a bis-N-heterocyclic carbene or diphosphine ligand.

In some embodiments of complexes of Formula II, the two M are each coordinated to an anionic 6-phenyl-2,2'- bipyridine (C^N^N) ligand and are connected with bis-N-heterocyclic carbene or diphosphine ligand.

In one aspect described herein are complexes having the structure of Formula II-A, or the pharmaceutically acceptable salt or ester thereof:

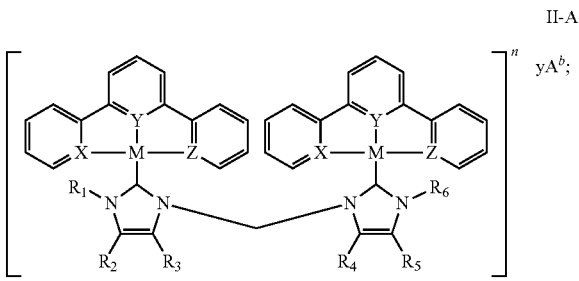

II-A where $R_1$, $R_2$, $R_3$, $R_4$, $R_5$, and $R_6$ are each independently hydrogen, substituted or unsubstituted $C_1$-$C_6$ alkyl, substituted or unsubstituted $C_1$-$C_6$ alkenyl, substituted or unsubstituted $C_1$-$C_6$ alkynyl, substituted or unsubstituted phenyl, substituted or unsubstituted aryl, substituted or unsubstituted heteroaryl, substituted or unsubstituted $C_1$-$C_6$ alkoxy, substituted or unsubstituted phenoxy, substituted or unsubstituted aroxy, substituted or unsubstituted $C_1$-$C_6$ alkylthio, substituted or unsubstituted phenylthio, substituted or unsubstituted arylthio, substituted or unsubstituted $C_1$-$C_6$ carbonyl, substituted or unsubstituted $C_1$-$C_6$ carboxyl, substituted or unsubstituted $C_1$-$C_6$ amino, substituted or unsubstituted $C_1$-$C_6$ amido, substituted or unsubstituted $C_1$-$C_6$ sulfonyl, $C_1$-$C_6$ sulfonic acid, substituted or unsubstituted $C_1$-$C_6$ phosphoryl, substituted or unsubstituted $C_1$-$C_6$ phosphonyl, substituted or unsubstituted diyaryl, substituted or unsubstituted $C_3$-$C_6$ cyclic, or substituted or unsubstituted heterocyclic; and where optionally and independently the pairs $R_1$ and $R_2$, $R_2$ and $R_3$, $R_4$ and $R_5$, and $R_5$ and $R_6$ together are —$(CH_2)_{3-5}$—.

Preferably, $R_1$, $R_2$, $R_3$, $R_4$, $R_5$, and $R_6$ are each independently hydrogen, substituted or unsubstituted $C_1$-$C_6$ alkyl, substituted or unsubstituted $C_1$-$C_6$ alkenyl, substituted or unsubstituted $C_1$-$C_6$ alkynyl, substituted or unsubstituted phenyl, substituted or unsubstituted aryl, substituted or unsubstituted heteroaryl, substituted or unsubstituted $C_1$-$C_6$ alkoxy, substituted or unsubstituted phenoxy, substituted or unsubstituted aroxy, substituted or unsubstituted diyaryl, substituted or unsubstituted $C_3$-$C_6$ cyclic, or substituted or unsubstituted heterocyclic. More preferably, $R_1$, $R_2$, $R_3$, $R_4$, $R_5$, and $R_6$ are each independently hydrogen, unsubstituted $C_1$-$C_6$ alkyl, unsubstituted $C_1$-$C_6$ alkenyl, unsubstituted $C_1$-$C_6$ alkynyl, unsubstituted phenyl, unsubstituted aryl, unsubstituted heteroaryl, unsubstituted $C_1$-$C_6$ alkoxy, unsubstituted phenoxy, unsubstituted aroxy, unsubstituted diyaryl, unsubstituted $C_3$-$C_6$ cyclic, or unsubstituted heterocyclic. Still more preferably, $R_1$, $R_2$, $R_3$, $R_4$, $R_5$, and $R_6$ are each independently hydrogen, unsubstituted $C_1$-$C_6$ alkyl, unsubstituted $C_1$-$C_6$ alkenyl, unsubstituted $C_1$-$C_6$ alkynyl, unsubstituted phenyl, unsubstituted aryl, unsubstituted heteroaryl, unsubstituted $C_1$-$C_6$ alkoxy, unsubstituted phenoxy, unsubstituted aroxy, unsubstituted $C_3$-$C_6$ cyclic, or unsubstituted heterocyclic. Even more preferably, $R_1$, $R_2$, $R_3$, $R_4$, $R_5$, and $R_6$ are each independently hydrogen, unsubstituted phenyl, unsubstituted aryl, unsubstituted heteroaryl, unsubstituted phenoxy, unsubstituted aroxy, unsubstituted $C_3$-$C_6$ cyclic, or unsubstituted heterocyclic.

In some embodiments of complexes of Formula II-A: each M is independently selected from Au, Pt, or Pd; $R_2$, $R_3$, $R_4$, and $R_5$ are each hydrogen; $R_1$ and $R_6$ are each independently selected from —$CH_3$, benzyl, or naphthalen-2-ylmethyl; n is +1 or +2; y is equal to the absolute value of n/b; and each X, Y, and Z are independently carbon or nitrogen.

In some embodiments of complexes of Formula II-A: each M is Platinum; $R_2$, $R_3$, $R_4$, and $R_5$ are each hydrogen; $R_1$ and $R_6$ are each benzyl; n is +2; $yA^b$ is 2 $CF_3SO_3^-$; each X is carbon, and each Y and Z is nitrogen.

In some embodiments of complexes of Formula II-A, each M is Platinum. In some embodiments of complexes of Formula II-A, $R_2$, $R_3$, $R_4$, and $R_5$ are each hydrogen. In some embodiments of complexes of Formula II-A, n is +2. In some embodiments of complexes of Formula II-A, $yA^b$ is 2 $CF_3SO_3^-$. In some embodiments of complexes of Formula II-A, each X is carbon. In some embodiments of complexes of Formula II-A, each Y and Z is nitrogen. In some embodiments of complexes of Formula II-A, $R_1$ and $R_6$ are each benzyl.

In one aspect described herein are complexes having the structure of Formula II-B, or the pharmaceutically acceptable salt or ester thereof:

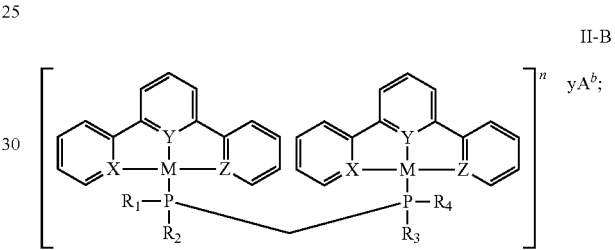

II-B where $R_1$, $R_2$, $R_3$, and $R_4$ are each independently hydrogen, substituted or unsubstituted $C_1$-$C_6$ alkyl, substituted or unsubstituted $C_1$-$C_6$ alkenyl, substituted or unsubstituted $C_1$-$C_6$ alkynyl, substituted or unsubstituted phenyl, substituted or unsubstituted aryl, substituted or unsubstituted heteroaryl, substituted or unsubstituted $C_1$-$C_6$ alkoxy, substituted or unsubstituted phenoxy, substituted or unsubstituted aroxy, substituted or unsubstituted $C_1$-$C_6$ alkylthio, substituted or unsubstituted phenylthio, substituted or unsubstituted arylthio, substituted or unsubstituted $C_1$-$C_6$ carbonyl, substituted or unsubstituted $C_1$-$C_6$ carboxyl, substituted or unsubstituted $C_1$-$C_6$ amino, substituted or unsubstituted $C_1$-$C_6$ amido, substituted or unsubstituted $C_1$-$C_6$ sulfonyl, $C_1$-$C_6$ sulfonic acid, substituted or unsubstituted $C_1$-$C_6$ phosphoryl, substituted or unsubstituted $C_1$-$C_6$ phosphonyl, substituted or unsubstituted diyaryl, substituted or unsubstituted $C_3$-$C_6$ cyclic, or substituted or unsubstituted heterocyclic.

Preferably, $R_1$, $R_2$, $R_3$, and $R_4$ are each independently hydrogen, substituted or unsubstituted $C_1$-$C_6$ alkyl, substituted or unsubstituted $C_1$-$C_6$ alkenyl, substituted or unsubstituted $C_1$-$C_6$ alkynyl, substituted or unsubstituted phenyl, substituted or unsubstituted aryl, substituted or unsubstituted heteroaryl, substituted or unsubstituted $C_1$-$C_6$ alkoxy, substituted or unsubstituted phenoxy, substituted or unsubstituted aroxy, substituted or unsubstituted diyaryl, substituted or unsubstituted $C_3$-$C_6$ cyclic, or substituted or unsubstituted heterocyclic. More preferably, $R_1$, $R_2$, $R_3$, and $R_4$ are each independently hydrogen, unsubstituted $C_1$-$C_6$ alkyl, unsubstituted $C_1$-$C_6$ alkenyl, unsubstituted $C_1$-$C_6$ alkynyl, unsubstituted phenyl, unsubstituted aryl, unsubstituted heteroaryl, unsubstituted $C_1$-$C_6$ alkoxy, unsubstituted phenoxy, unsubstituted aroxy, unsubstituted diyaryl, unsubstituted $C_3$-$C_6$ cyclic, or unsubstituted heterocyclic. Still more preferably, $R_1$, $R_2$, $R_3$, and $R_4$ are each independently unsubstituted $C_1$-$C_6$ alkyl, unsubstituted $C_1$-$C_6$ alkenyl, unsubstituted $C_1$-$C_6$ alkynyl, unsubstituted phenyl, unsubstituted aryl, unsubstituted heteroaryl, unsubstituted $C_1$-$C_6$ alkoxy, unsubstituted phenoxy, unsubstituted aroxy, unsubstituted $C_3$-$C_6$ cyclic, or unsubstituted heterocyclic. Even more preferably, $R_1$, $R_2$, $R_3$, and $R_4$ are each independently unsubstituted phenyl, unsubstituted aryl, unsubstituted heteroaryl, unsubstituted phenoxy, unsubstituted aroxy, unsubstituted $C_3$-$C_6$ cyclic, or unsubstituted heterocyclic.

In some embodiments of complexes of Formula II-B: each M is independently selected from Au, Pt or Pd; $R_1$, $R_2$, $R_3$, and $R_4$ are each independently selected from phenyl or $C_6H_6$; n is +1 or +2; y is equal to the absolute value of n/b; and each X, Y, and Z are independently carbon or nitrogen.

In some embodiments of complexes of Formula II-B: each M is Platinum; $R_1$, $R_2$, $R_3$, and $R_4$ are each phenyl; n is +2; yAb is 2 $CF_3SO_3^-$; each X is carbon, and each Y and Z is nitrogen.

In some embodiments of complexes of Formula II-B, each M is Platinum. In some embodiments of complexes of Formula II-B, $R_1$, $R_2$, $R_3$, and $R_4$ are each phenyl. In some embodiments of complexes of Formula II-B, n is +2. In some embodiments of complexes of Formula II-B, $yA^b$ is 2 $CF_3SO_3^-$. In some embodiments of complexes of Formula II-B, each X is carbon. In some embodiments of complexes of Formula II-B, each Y and Z is nitrogen.

In some embodiments of the complexes, each M is, independently, platinum(II) (Pt(II) or $Pt^{2+}$), palladium(II) (Pd(II) or $Pd^{2+}$), or gold(III) (Au(III) or $Au^{3+}$).

Also disclosed is the synthesis of novel metal (II/III) complexes containing N-heterocyclic carbene ligand (NHC) or phosphine ligand, and their application in targeting mismatched sites in DNA.

1. M(II)/(III)-NHC Complexes

Preferred M(II)/(III)-NHC complexes are molecules of, for example, a Platinum (II), Palladium(II), or Gold(III) ion connected to a tridentate ligand and N-heterocyclic carbene ligand, which can be represented by structural Formula I-A, or an acceptable salt thereof:

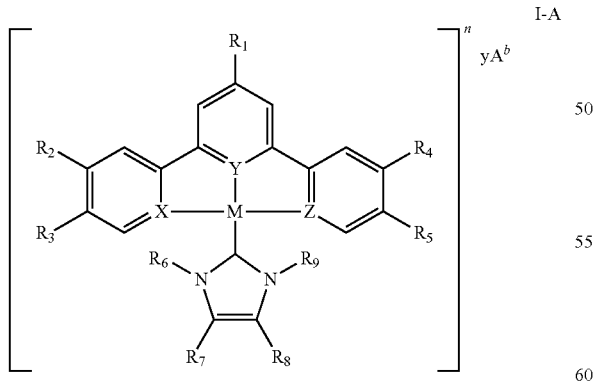

I-A where:
M is Au, Pt, or Pd;
$R_1$ is hydrogen or phenyl;
$R_2$ and $R_3$ are each independently hydrogen or are connected to $C_4H_4$ to form

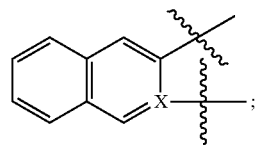

$R_4$, $R_5$, $R_7$, and $R_g$ are each hydrogen;

$R_6$ and $R_9$ are each independently selected from a —$CH_3$, —$C_2H_5$, —$C_3H_7$, —$C_4H_9$, —$C_5H_{11}$, —$C_6H_{13}$, benzyl, (2-hydroxy) ethyl, phenyl, naphthalen-2-ylmethyl, and (2-phenyl) ethyl;

n is an integer from +1 to +2;

y is equal to the absolute value of n/b; and

X, Y, and Z are independently selected from a carbon atom or a nitrogen atom.

Tridentate ligands are, for example, anionic or di-anionic 1,3-di(pyridin-2-yl)benzene (N^CH^N), 2,6-diphenylpyridine (HC^N^CH), 6-phenyl-2,2'-bipyridine (HUNAN) and its analogue 6-(naphthalen-2-yl)-2,2'-bipyridine, 4,6-diphenyl-2,2'-bipyridine ligands. Non-limiting examples of the HC^N^N, N^CH^N and HC^N^CH ligands are:

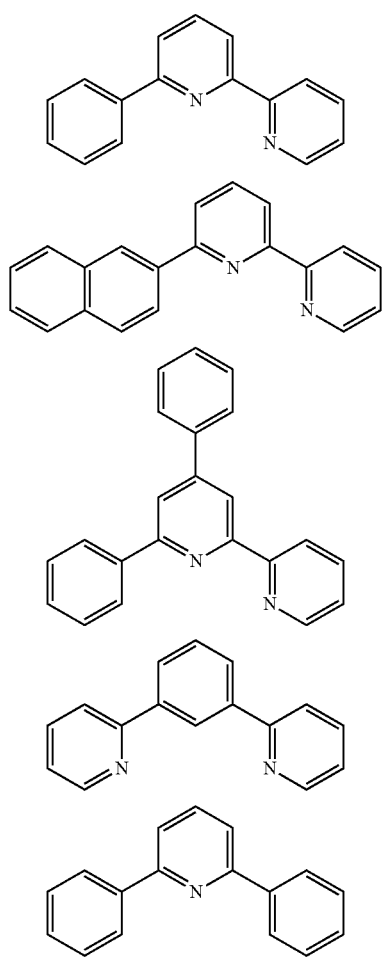

N-heterocyclic carbenes are, for example, ligands having the structure:

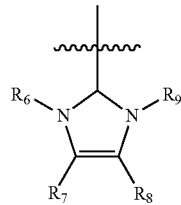

where $R_6$ and $R_9$ are each independently selected from —$CH_3$, —$C_2H_5$, —$C_3H_7$, —$C_4H_9$, —$C_5H_{11}$, —$C_6H_{13}$, benzyl, (1-hydroxy) ethyl, phenyl, naphthalen-2-ylmethyl, (phenyl) ethyl; and $R_7$ and $R_8$, are each hydrogen.

It will be understood that the anionic C^N^N and NACAN ligand can form a non-neutral complex with the Platinum(II) or Palladium (II) ion. In addition, di-anionic C^N^C ligand can form net charge complex with Gold (III) ion. For instance, the net positive charge on the Platinum(II) can be greater than the absolute net negative charge of the C^N^N ligand. In view of this, there can be at least one counter-anion coordinated to the Pt(II)-NHC complex for charge neutralization.

Accordingly, an acceptable salt can include salts formed from the charged Pt(II)-NHC, Pd (II)-NHC and Au(III)-NHC complexes and their counter-anion(s). Counter-ions include ions associated with a positively charged Pt(II)-NHC, Pd (II)-NHC and Au(III)-NHC complexes. Non-limiting examples of counter-ions include halogens such as fluoride, chloride, bromide, iodide; sulfate; phosphate; trifluoromethanesulfonate; acetate; nitrate; perchlorate; acetylacetonate; hexafluorophosphate and hexafluoroacetylacetonate.

Also disclosed are novel Platinum(II) [or Pt(II) or $Pt^{2+}$], Palladium(II) [or Pd(II) or $Pd^{2+}$], and Gold(III) [or Au(III) or $Au^{3+}$] complexes bearing N-heterocyclic carbene ligand.

The Platinum(II), Palladium(II), or Gold(III)-NHC complexes can be represented by one or more of structural Formula I-A, or an acceptable salt thereof:

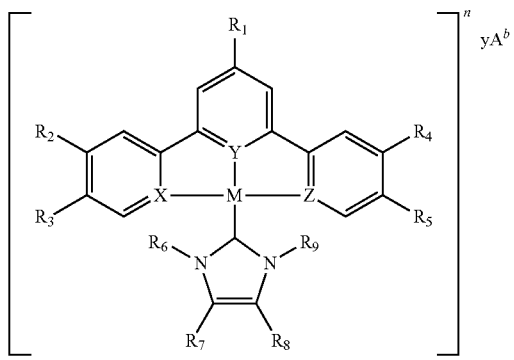

where

M is Au, Pt, or Pd;

$R_1$ is hydrogen or phenyl;

$R_2$ and $R_3$ are each hydrogen or are connected to $C_4H_4$ to form

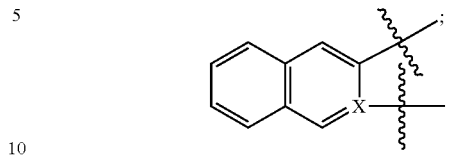

$R_4$, $R_5$, $R_7$, and $R_8$ are each hydrogen;

$R_6$ and $R_9$ are each independently selected from a —$CH_3$, —$C_2H_5$, —$C_3H_7$, —$C_4H_9$, —$C_5H_{11}$, —$C_6H_{13}$, benzyl, (2-hydroxy) ethyl, phenyl, naphthalen-2-ylmethyl, (2-phenyl) ethyl;

n is an integer from +1 to +2;

y is equal to the absolute value of n/b; and

X, Y, and Z are each independently selected from a carbon atom or a nitrogen atom.

For Complex 1, the M(II)/(III)-NHC complex have the structure of Formula I or a counter-anion thereof, where M is a Platinum atom; $R_1$ is hydrogen; $R_2$ and $R_3$ are each hydrogen; $R_4$, $R_5$, $R_7$, and $R_8$ are each hydrogen; $R_6$ and $R_9$ are each —$CH_3$; n is +1; $yA^b$ is $CF_3SO_3^-$; X is a carbon atom, and Y and Z are each a nitrogen atom.

For Complex 2, the M(II)/(III)-NHC complex has a Formula I-A or a counteranion thereof, wherein M is a Platinum atom; $R_1$ is —H; $R_2$, $R_3$ are each —H; $R_4$, $R_5$, $R_7$, $R_8$, are each —H; $R_6$ is benzyl group; $R_9$ is —$CH_3$; n is +1; $yA^b$ is $CF_3SO_3^-$; X is a carbon atom, and Y and Z are each a nitrogen atom.

For Complex 3, the M(II)/(III)-NHC complex has a Formula I-A or a counteranion thereof, wherein M is a Platinum atom; $R_1$ is —H; $R_2$, $R_3$ are each —H; $R_4$, $R_5$, $R_7$, $R_8$, are each —H; $R_6$ is benzyl group; $R_9$ is —$C_2H_4$; n is +1; $yA^b$ is $CF_3SO_3^-$; X is a carbon atom, and Y and Z are each a nitrogen atom.

For Complex 4, the M(II)/(III)-NHC complex has a Formula I-A or a counteranion thereof, wherein M is a Platinum atom; $R_1$ is —H; $R_2$, $R_3$ are each —H; $R_4$, $R_5$, $R_7$, $R_8$, are each —H; $R_6$ is benzyl group; $R_9$ is —$C_3H_7$; n is +1; $yA^b$ is $CF_3SO_3^-$; X is a carbon atom, and Y and Z are each a nitrogen atom.

For Complex 5, the M(II)/(III)-NHC complex has a Formula I-A or a counteranion thereof, wherein, M is a Platinum atom; $R_1$ is —H; $R_2$, $R_3$ are each —H; $R_4$, $R_5$, $R_7$, $R_8$, are each —H; $R_6$ is benzyl group; $R_9$ is —$C_4H_9$; n is +1; $yA^b$ is $CF_3SO_3^-$; X is a carbon atom, and Y and Z are each a nitrogen atom.

For Complex 6, the M(II)/(III)-NHC complex has a Formula I-A or a counteranion thereof, wherein, M is a Platinum atom; $R_1$ is —H; $R_2$, $R_3$ are each —H; $R_4$, $R_5$, $R_7$, $R_8$, are each —H; $R_6$ is benzyl group; $R_9$ is —$C_5H_{11}$; n is +1; $yA^b$ is $CF_3SO_3^-$; X is a carbon atom, and Y and Z are each a nitrogen atom.

For Complex 7, the M(II)/(III)-NHC complex has a Formula I-A or a counteranion thereof, wherein, M is a Platinum atom; $R_1$ is —H; $R_2$, $R_3$ are each —H; $R_4$, $R_5$, $R_7$, $R_8$, are each —H; $R_6$ is benzyl group; $R_9$ is —$C_6H_{13}$; n is +1; $yA^b$ is $CF_3SO_3^-$; X is a carbon atom, and Y, Z are each nitrogen atom.

For Complex 8, the M(II)/(III)-NHC complex has a Formula I-A or a counteranion thereof, wherein M is a Platinum atom; $R_1$ is —H; $R_2$, $R_3$ are each —H; $R_4$, $R_5$, $R_7$, $R_8$, are each —H; $R_6$ and $R_9$ are each benzyl group; n is +1; $yA^b$ is $CF_3SO_3^-$; X is a carbon atom, and Y and Z are each a nitrogen atom.

For Complex 9, the M(II)/(III)-NHC complex has a Formula I-A or a counteranion thereof, wherein, M is a Platinum atom; $R_1$ is —H; $R_2$, $R_3$ are each —H; $R_4$, $R_5$, $R_7$, $R_8$, are each —H; $R_6$ is benzyl group; $R_9$ is (2-hydroxy) ethyl group; n is +1; $yA^b$ is $CF_3SO_3^-$; X is a carbon atom, and Y and Z are each a nitrogen atom.

For Complex 10, the M(II)/(III)-NHC complex has a Formula I-A or a counteranion thereof, wherein, M is a Platinum atom; $R_1$ is —H; $R_2$, $R_3$ are each —H; $R_4$, $R_5$, $R_7$, $R_8$, are each —H; $R_6$ is phenyl group; $R_9$ is $C_4H_9$; n is +1; $yA^b$ is $CF_3SO_3^-$; X is a carbon atom, and Y and Z are each a nitrogen atom.

For Complex 11, the M(II)/(III)-NHC complex has a Formula I-A or a counteranion thereof, wherein, M is a Platinum atom; $R_1$ is —H; $R_2$, $R_3$ are each —H; $R_4$, $R_5$, $R_7$, $R_8$, are each —H; $R_6$ is naphthalen-2-ylmethyl group; $R_9$ is $C_4H_9$; n is +1; $yA^b$ is $CF_3SO_3^-$; X is a carbon atom, and Y and Z are each a nitrogen atom.

For Complex 12, the M(II)/(III)-NHC complex has a Formula I-A or a counteranion thereof, wherein, M is a Platinum atom; $R_1$ is —H; $R_2$, $R_3$ are each —H; $R_4$, $R_5$, $R_7$, $R_8$, are each —H; $R_6$ is (2-phenyl) ethyl group; $R_9$ is $C_4H_9$; n is +1; $yA^b$ is $CF_3SO_3^-$; X is a carbon atom, and Y and Z are each a nitrogen atom.

For Complex 13, the M(II)/(III)-NHC complex has a Formula I-A or a counteranion thereof, wherein, M is a Platinum atom; $R_1$ is —H; $R_2$, $R_3$ are each —H; $R_4$, $R_5$, $R_7$, $R_8$, are each —H; $R_6$, $R_9$ are each phenyl group; n is +1; $yA^b$ is $CF_3SO_3^-$; X is a carbon atom, and Y and Z are each a nitrogen atom.

For Complex 14, the M(II)/(III)-NHC complex has a Formula I-A or a counteranion thereof, wherein, M is a Platinum atom; $R_1$ is —H; $R_2$, $R_3$ are each —H; $R_4$, $R_5$, $R_7$, $R_8$, are each —H; $R_6$, $R_9$ are each $C_4H_9$ group; n is +1; $yA^b$ is $CF_3SO_3^-$; X is a carbon atom, and Y and Z are each a nitrogen atom.

For Complex 15, the M(II)/(III)-NHC complex has a Formula I-A or a counteranion thereof, wherein, M is a Platinum atom; $R_1$ is —H; $R_2$ and $R_3$ are each connected to $C_4H_4$ to form

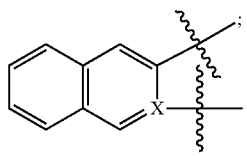

$R_4$, $R_5$, $R_7$, $R_8$, are each —H; $R_6$ is benzyl group; $R_9$ is $C_4H_9$; n is +1; $yA^b$ is $CF_3SO_3^-$; X is a carbon atom, and Y and Z are each a nitrogen atom.

For Complex 16, the M(II)/(III)-NHC complex has a Formula I-A or a counteranion thereof, wherein, M is a Platinum atom; $R_1$ is phenyl group; $R_2$, $R_3$ are each —H; $R_4$, $R_5$, $R_7$, $R_8$, are each —H; $R_6$ is benzyl group; $R_9$ is —$C_4H_9$; n is +1; $yA^b$ is $CF_3SO_3^-$; X is a carbon atom, and Y and Z are each a nitrogen atom.

For Complex 17, the M(II)/(III)-NHC complex has a Formula I-A or a counteranion thereof, wherein, M is a Platinum atom; $R_1$ is —H; $R_2$, $R_3$ are each —H; $R_4$, $R_5$, $R_7$, $R_8$, are each —H; $R_6$ is benzyl group; $R_9$ is —$C_4H_9$; n is +1; $yA^b$ is $CF_3SO_3^-$; X and Z are each a nitrogen atom, and Y is a carbon atom.

For Complex 18, the M(II)/(III)-NHC complex has a Formula I-A or a counteranion thereof, wherein, M is a Palladium atom; $R_1$ is —H; $R_2$, $R_3$ are each —H; $R_4$, $R_5$, $R_7$, $R_8$, are each —H; $R_6$, $R_9$ are each —$C_4H_9$ group; n is +1; $yA^b$ is $CF_3SO_3^-$; X is a carbon atom, and Y and Z are each a nitrogen atom.

For Complex 19, the M(II)/(III)-NHC complex has a Formula I-A or a counteranion thereof, wherein, M is a Gold atom; $R_1$ is —H; $R_2$, $R_3$ are each —H; $R_4$, $R_5$, $R_7$, $R_8$, are each —H; $R_6$ is benzyl group; $R_9$ 1S —$C_4H_9$; n is +1; $yA^b$ is $CF_3SO_3^-$; X and Z are each a carbon atom, and Y is a nitrogen atom.

2. Di-nuclear M(II/III) complexes with —NHC ligand

Preferred di-nuclear M(II/III) complexes with —NHC ligands are, for example, molecules with two metal (II/III) ions connected by a N-heterocyclic carbene ligand. In addition, each M (II/III) ion is also connected to a tridentate ligand. Their structure can be represented by structural Formula II-A, or an acceptable salt thereof:

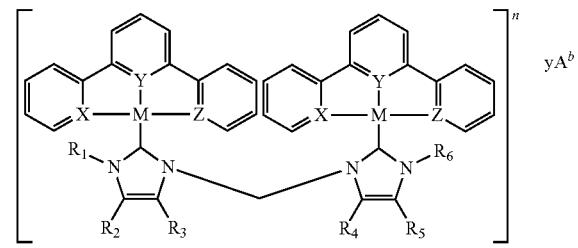

II-A where
each M is independently selected from Au, Pt, or Pd;
$R_2$, $R_3$, $R_4$, and $R_5$ are each hydrogen;
$R_1$ and $R_6$ are each independently selected from —$CH_3$, benzyl, andnaphthalen-2-ylmethyl
n is an integer from +1 to +2;
y is equal to the absolute value of n/b; and
each X, Y, and Z are independently selected from a carbon atom or a nitrogen atom.

In some embodiments, the tridentate ligand can be an anionic 6-phenyl-2,2'-bipyridine (C^N^N). A non-limiting example of the C^N^N ligand is:

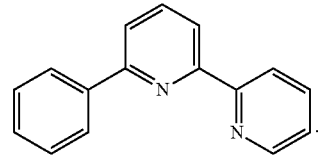 [SMILES: c1ccc(-c2cccc(-c3ccccn3)n2)cc1]

In some embodiments, the N-heterocyclic carbine can be a ligand having the structure:

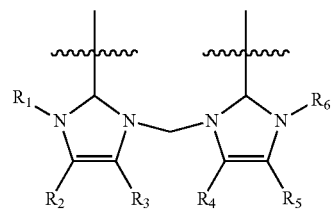

where $R_2, R_3, R_4$, and $R_5$ are each hydrogen; and $R_1$, $R_6$ are each independently selected from —$CH_3$, benzyl, and naphthalen-2-ylmethyl.

It will be understood that the anionic C^N^N ligand can form a non-neutral complex with the Platinum(II) ion. For instance, the net positive charge on the Platinum(II) can be greater than the absolute net negative charge of the C^N^N ligand. In view of this, there can be at least one counter-anion coordinated to the Pt(II)-NHC complex for charge neutralization.

Accordingly, acceptable salts include salts formed from the charged M(II/III)-NHC complex and counter-anion(s).

Counter-anions (a form of counter-ion) include ions associated with a positively charged M(II/III)-NHC complex. Non-limiting examples of counter-ions include halogens such as fluoride, chloride, bromide, iodide; sulfate; phosphate; trifluoromethanesulfonate; acetate; nitrate; perchlorate; acetylacetonate; hexafluorophosphate and hexafluoroacetylacetonate.

The disclosed di-nuclear M(II/III)-NHC complexes can be represented by the structure of Formula II-A, or an acceptable salt thereof:

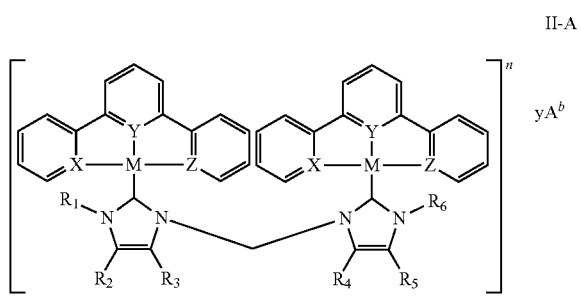

II-A where
each M is independently selected from Au, Pt, or Pd;
$R_2$, $R_3$, $R_4$, $R_5$ are each hydrogen;
$R_1$ and $R_6$ are each independently selected from —$CH_3$, benzyl, and naphthalen-2-ylmethyl;
n is an integer from +1 to +2;
y is equal to the absolute value of n/b; and
each X, Y, and Z are independently selected from a carbon atom or a nitrogen atom.

For Complex 20, the di-nuclear M(II/III) complex with N-heterocyclic carbene ligand has a Formula II or a counteranion thereof, wherein, M is a Platinum atom; $R_2, R_3, R_4$, $R_5$ are each —H; $R_1$, $R_6$ are each —$CH_3$; n is +2; $yA^b$ is 2 $CF_3SO_3^-$; X is a carbon atom, and Y and Z are each a nitrogen atom. (complex 20)

For Complex 21, the di-nuclear M(II/III) complex with N-heterocyclic carbene ligand has a Formula II-A or a counteranion thereof, wherein, M is a Platinum atom; $R_2, R_3$, $R_4, R_5$ are each —H; $R_1$, $R_6$ are each benzyl group; n is +2; $yA^b$ is 2 $CF_3SO_3^-$; X is a carbon atom, and Y and Z are each a nitrogen atom.

For Complex 22, the di-nuclear M(II/III) complex with N-heterocyclic carbene ligand has a Formula II-A or a counteranion thereof, wherein, M is a Platinum atom; $R_2, R_3$, $R_4, R_5$ are each —H; $R_1$, $R_6$ are each naphthalen-2-ylmethyl group; n is +2; $yA^b$ is 2 $CF_3SO_3^-$; X is a carbon atom, and Y and Z are each a nitrogen atom.

3. Di-nuclear M(II/III) Complexes with Phosphine Ligand

Di-nuclear M(II/III) complexes with phosphine ligands include molecules with two metal (II/III) ions connected by di-phosphine ligand. In addition, each M (II) ion is also connected to a tridentate ligand. Their structure can be represented by structural Formula II-B, or an acceptable salt thereof:

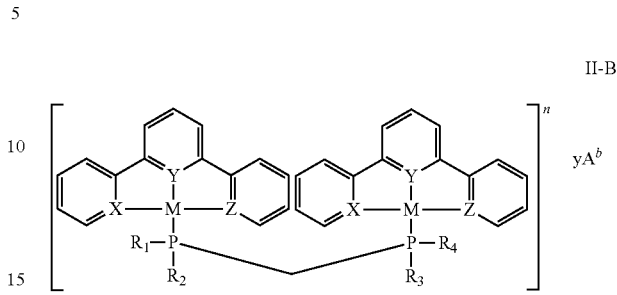

II-B where
each M is independently selected from Au, Pt, or Pd;
$R_1$, $R_2$, $R_3$, and $R_4$ are each independently selected from phenyl or $C_6H_6$;
n is an integer from +1 to +2;
y is equal to the absolute value of n/b; and
each X, Y, and Z are independently selected from a carbon atom or a nitrogen atom.

Tridentate ligands include anionic 6-phenyl-2,2'-bipyridines (C^N^N). A non-limiting example of the C^N^N ligand is:

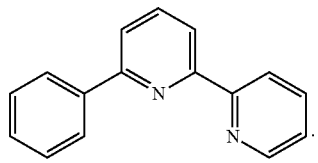 [SMILES: c1ccc(-c2cccc(-c3ccccn3)n2)cc1]

Phosphines include ligands having the structure:

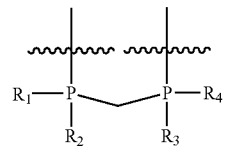

where $R_1, R_2, R_3$, and $R_4$ are each independently selected from phenyl or $C_6H_6$.

It will be understood that the anionic C^N^N ligand can form a non-neutral complex with the Platinum(II) ion. For instance, the net positive charge on the Platinum(II) can be greater than the absolute net negative charge of the C^N^N ligand. In view of this, there can be at least one counter-anion coordinated to the di-nuclear Pt(II)-phosphine complex for charge neutralization.

Accordingly, acceptable salts include salts formed from the charged di-nuclear M(II/III)-phosphine complex and counter-anion(s).

Counter-anions to an ion associated with a positively charged di-nuclear M(II/III)-phosphine complex. Non-limiting examples of counter-ions include halogens such as fluoride, chloride, bromide, iodide; sulfate; phosphate; trifluoromethanesulfonate; acetate; nitrate; perchlorate; acetylacetonate; hexafluorophosphate and hexafluoroacetylacetonate.

The disclosed di-nuclear M(II/III)-phosphine complexes can be represented by the structure of Formula II-B, or an acceptable salt thereof:

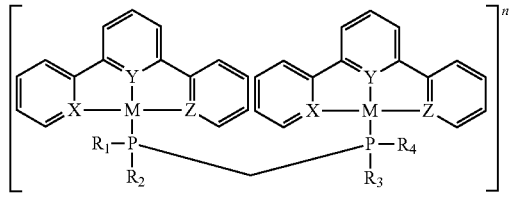

II-B where each M is independently selected from Au, Pt, or Pd;

$R_1$, $R_2$, $R_3$, and $R_4$ are each independently selected from phenyl or $C_6H_6$;

n is an integer from +1 to +2;

y is equal to the absolute value of n/b; and each X, Y, and Z are independently selected from a carbon atom or a nitrogen atom.

For Complex 23, the di-nuclear M(II/III) complex with phosphine ligand has a Formula II-B or an salt thereof, wherein, M is a Platinum atom; $R_1,R_2,R_3,R_4$ are each $C_6H_6$; n is +2; $yA^b$ is 2 $CF_3SO_3^-$; X is a carbon atom, and Y and Z are each a nitrogen atom.

For Complex 24, the di-nuclear M(II/III) complex with phosphine ligand has a Formula II-B or an salt thereof, wherein, M is a Platinum atom; $R_1,R_2,R_3,R_4$ are each phenyl group; n is +2; $yA^b$ is 2 $CF_3SO_3^-$; X is a carbon atom, and Y and Z are each a nitrogen atom.

The structures of complexes 1 to 24 are shown below:

1

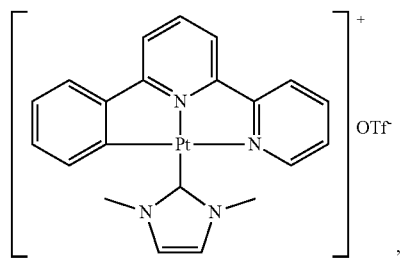

2

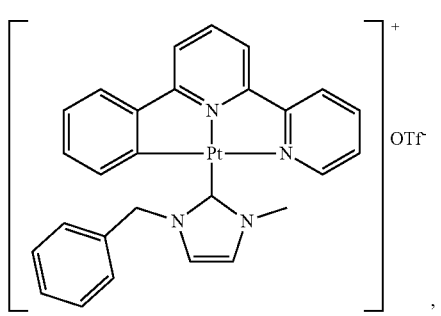

-continued

3

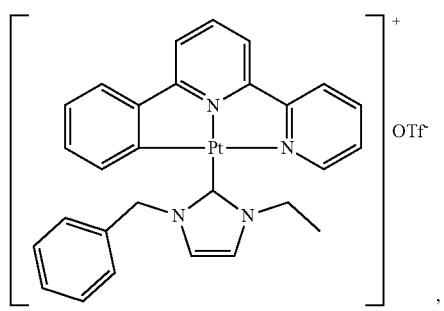

4

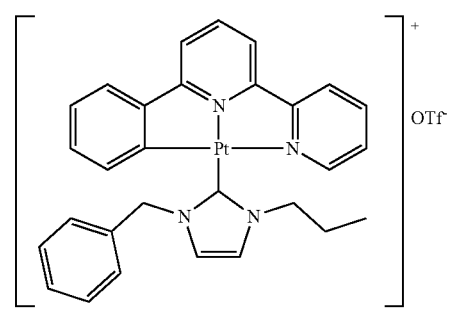

5

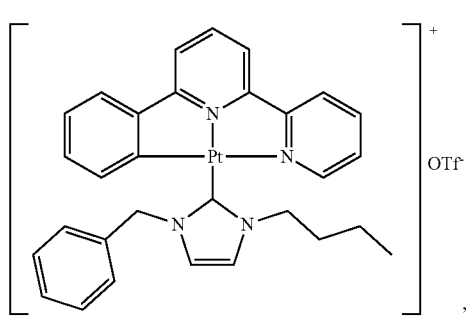

6

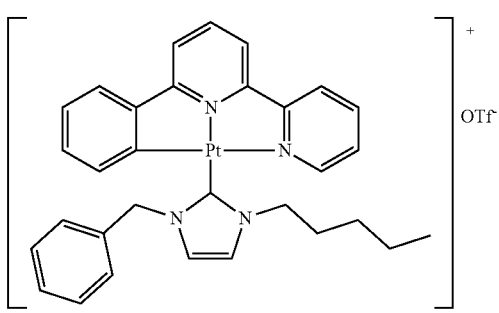

7

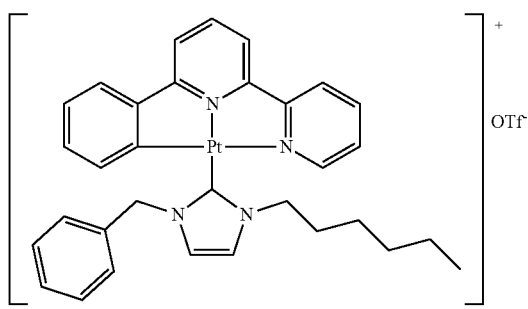

-continued
8
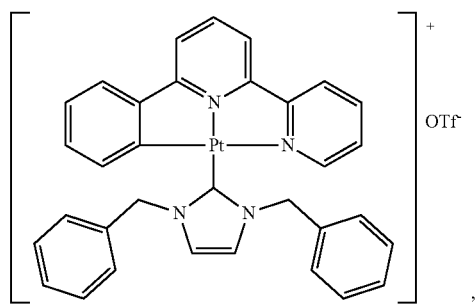
9
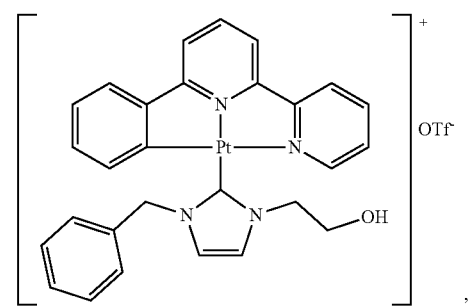
10
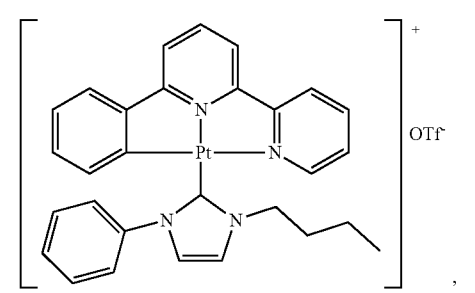
11
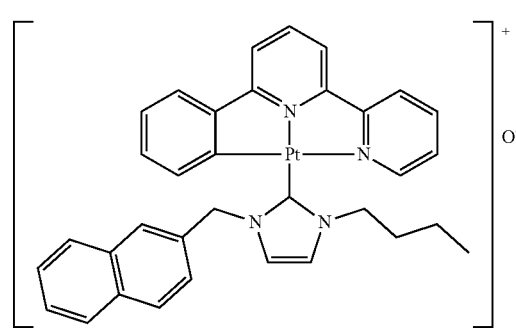
12
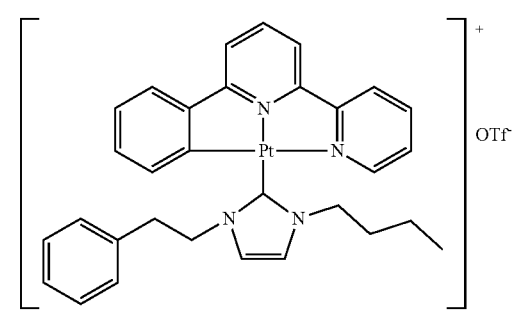
-continued
13
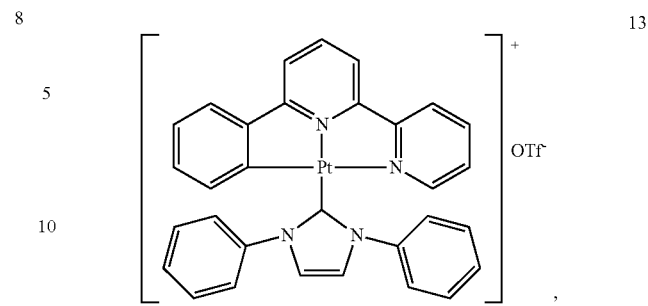
14
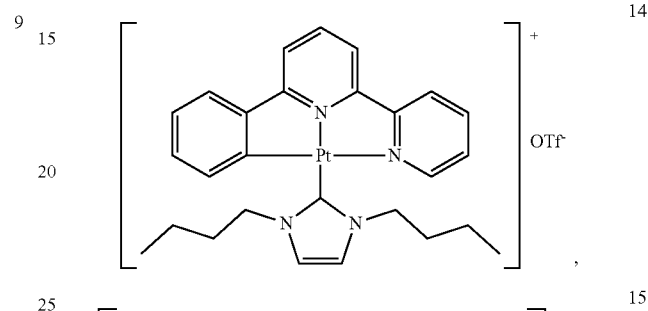
15
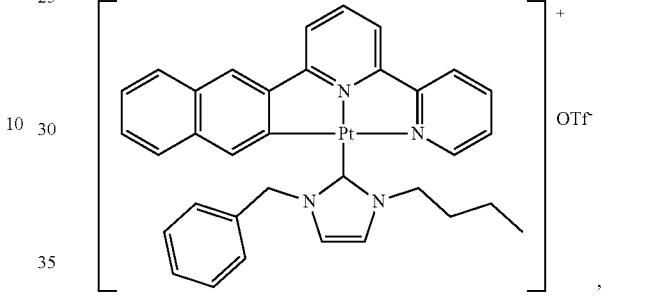
16
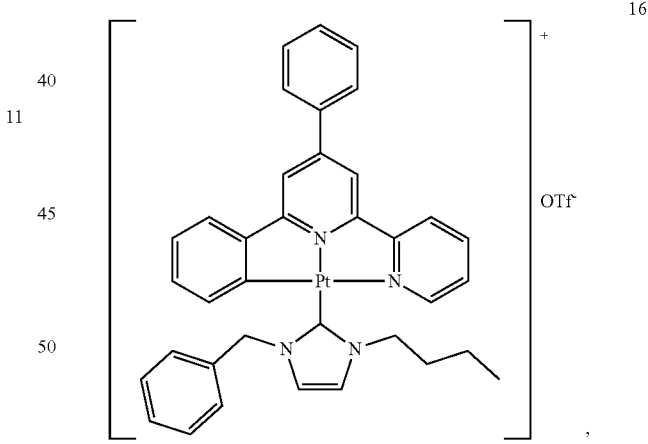
17
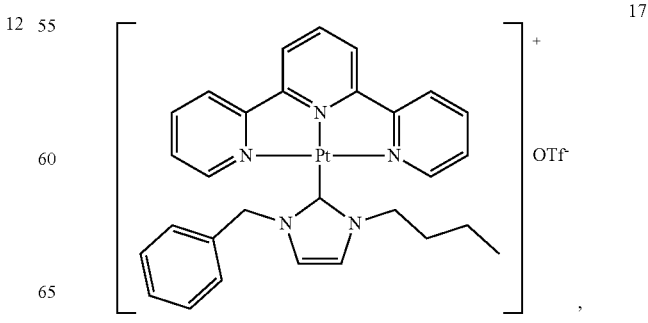

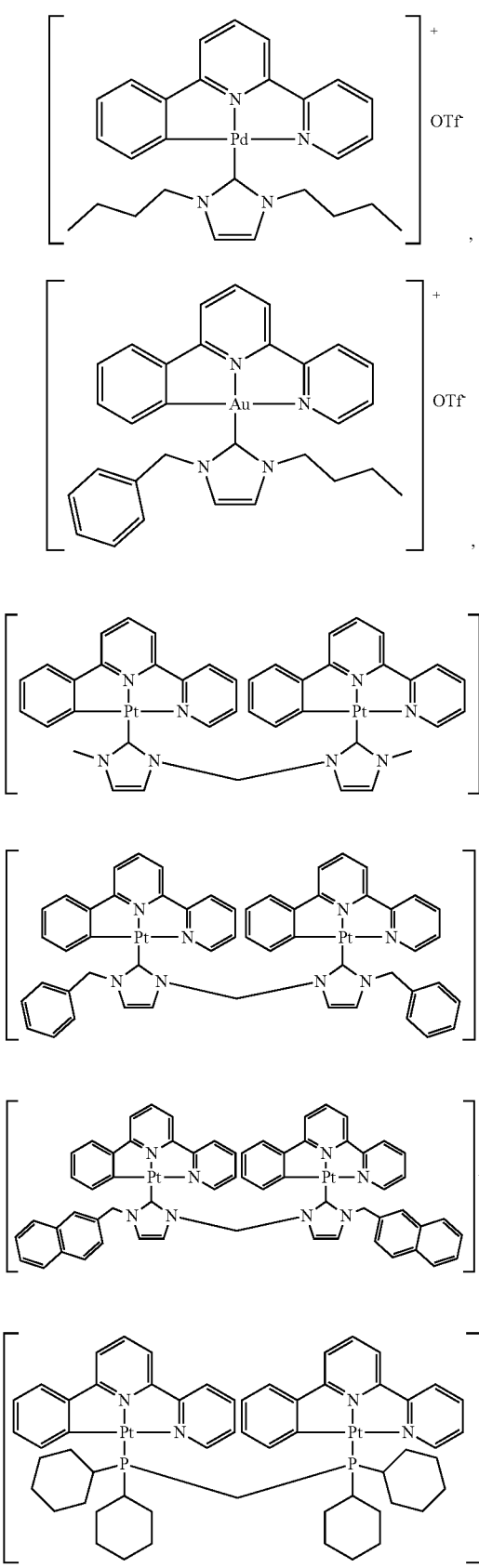

Every complex within the above definition is intended to be and should be considered to be specifically disclosed herein. Further, every subgroup that can be identified within the above definition is intended to be and should be considered to be specifically disclosed herein. As a result, it is specifically contemplated that any complex, or subgroup of complexes can be either specifically included for or excluded from use or included in or excluded from a list of complexes.

B. Kits

The materials described above as well as other materials can be packaged together in any suitable combination as a kit useful for performing, or aiding in the performance of, the disclosed method. It is useful if the kit components in a given kit are designed and adapted for use together in the disclosed method. For example disclosed are kits for targeting and detection of mismatched DNA, the kit comprising one or more complexes as disclosed and one or more reagents for contacting cells with the complex(es), for detecting increased emission of the intercalated complex (es), or a combination thereof.

C. Mixtures

Disclosed are mixtures formed by performing or preparing to perform the disclosed method. For example, disclosed are mixtures comprising one or more of the disclosed complexes and a DNA sample.

Whenever the method involves mixing or bringing into contact complexes or components or reagents, performing the method creates a number of different mixtures. For example, if the method includes 3 mixing steps, after each one of these steps a unique mixture is formed if the steps are performed separately. In addition, a mixture is formed at the completion of all of the steps regardless of how the steps were performed. The present disclosure contemplates these mixtures, obtained by the performance of the disclosed methods as well as mixtures containing any disclosed reagent, composition, complex, or component, for example, disclosed herein.

D. Systems

Disclosed are systems useful for performing, or aiding in the performance of, the disclosed method. Systems generally comprise combinations of articles of manufacture such as structures, machines, devices, and the like, and compositions, complexes, compounds, materials, and the like. Such combinations that are disclosed or that are apparent from the disclosure are contemplated. For example, disclosed and contemplated are systems comprising one or more of the disclosed complexes, a DNA sample, and a device for detecting increased emission of the intercalated complex (es).

E. Data Structures and Computer Control

Disclosed are data structures used in, generated by, or generated from, the disclosed method. Data structures generally are any form of data, information, and/or objects collected, organized, stored, and/or embodied in a medium. Measurements of emission of intercalated complex(es) stored in electronic form, such as in RAM or on a storage disk, is a type of data structure.

The disclosed method, or any part thereof or preparation therefor, can be controlled, managed, or otherwise assisted by computer control. Such computer control can be accomplished by a computer controlled process or method, can use and/or generate data structures, and can use a computer program. Such computer control, computer controlled processes, data structures, and computer programs are contemplated and should be understood to be disclosed herein.

Uses

The disclosed methods and complexes are applicable to numerous areas including, but not limited to, targeting and detection of mismatched DNA. Other uses include detecting cancer cells, diagnosing cancer in a subject, and aiding treatment of a subject having cancer. Other uses are disclosed, apparent from the disclosure, and/or will be understood by those in the art.

A. Actions Based on Identifications

The disclosed methods include the determination, identification, indication, correlation, diagnosis, prognosis, etc. (which can be referred to collectively as "identifications") of subjects, diseases, conditions, states, etc. based on measurements, detections, comparisons, analyses, assays, screenings, etc. For example, subject can be identified as having cancer based on targeting and detection of mismatched DNA in cells of the subject. Such identifications are useful for many reasons. For example, and in particular, such identifications allow specific actions to be taken based on, and relevant to, the particular identification made. For example, diagnosis of a particular disease or condition in particular subjects (and the lack of diagnosis of that disease or condition in other subjects) has the very useful effect of identifying subjects that would benefit from treatment, actions, behaviors, etc. based on the diagnosis. For example, treatment for a particular disease or condition in subjects identified is significantly different from treatment of all subjects without making such an identification (or without regard to the identification). Subjects needing or that could benefit from the treatment will receive it and subjects that do not need or would not benefit from the treatment will not receive it.

Accordingly, also disclosed herein are methods comprising taking particular actions following and based on the disclosed identifications. For example, disclosed are methods comprising creating a record of an identification (in physical—such as paper, electronic, or other—form, for example). Thus, for example, creating a record of an identification based on the disclosed methods differs physically and tangibly from merely performing a measurement, detection, comparison, analysis, assay, screen, etc. Such a record is particularly substantial and significant in that it allows the identification to be fixed in a tangible form that can be, for example, communicated to others (such as those who could treat, monitor, follow-up, advise, etc. the subject based on the identification); retained for later use or review; used as data to assess sets of subjects, treatment efficacy, accuracy of identifications based on different measurements, detections, comparisons, analyses, assays, screenings, etc., and the like. For example, such uses of records of identifications can be made, for example, by the same individual or entity as, by a different individual or entity than, or a combination of the same individual or entity as and a different individual or entity than, the individual or entity that made the record of the identification. The disclosed methods of creating a record can be combined with any one or more other methods disclosed herein, and in particular, with any one or more steps of the disclosed methods of identification.

As another example, disclosed are methods comprising making one or more further identifications based on one or more other identifications. For example, particular treatments, monitorings, follow-ups, advice, etc. can be identified based on the other identification. For example, identification of a subject as having a disease or condition with a high level of a particular component or characteristic can be further identified as a subject that could or should be treated with a therapy based on or directed to the high level component or characteristic. A record of such further identifications can be created (as described above, for example) and can be used in any suitable way. Such further identifications can be based, for example, directly on the other identifications, a record of such other identifications, or a combination. Such further identifications can be made, for example, by the same individual or entity as, by a different individual or entity than, or a combination of the same individual or entity as and a different individual or entity than, the individual or entity that made the other identifications. The disclosed methods of making a further identification can be combined with any one or more other methods disclosed herein, and in particular, with any one or more steps of the disclosed methods of identification.

As another example, disclosed are methods comprising treating, monitoring, following-up with, advising, etc. a subject identified in any of the disclosed methods. Also disclosed are methods comprising treating, monitoring, following-up with, advising, etc. a subject for which a record of an identification from any of the disclosed methods has been made. For example, particular treatments, monitorings, follow-ups, advice, etc. can be used based on an identification and/or based on a record of an identification. For example, a subject identified as having a disease or condition with a high level of a particular component or characteristic (and/or a subject for which a record has been made of such an identification) can be treated with a therapy based on or directed to the high level component or characteristic. Such treatments, monitorings, follow-ups, advice, etc. can be based, for example, directly on identifications, a record of such identifications, or a combination. Such treatments, monitorings, follow-ups, advice, etc. can be performed, for example, by the same individual or entity as, by a different individual or entity than, or a combination of the same individual or entity as and a different individual or entity than, the individual or entity that made the identifications and/or record of the identifications. The disclosed methods of treating, monitoring, following-up with, advising, etc. can be combined with any one or more other methods disclosed herein, and in particular, with any one or more steps of the disclosed methods of identification.

The disclosed measurements, detections, comparisons, analyses, assays, screenings, etc. can be used in other ways and for other purposes than those disclosed. For example, the disclosed targeting and detection of mismatched DNA can identify when DNA has been damaged, mutated, not repaired, or a combination thereof. Thus, the disclosed measurements, detections, comparisons, analyses, assays, screenings, etc. do not encompass all uses of such measurements, detections, comparisons, analyses, assays, screenings, etc.

Methods

A. Synthetic Methods The disclosed complexes can be synthesized by standard organic synthetic techniques.

Examples of such techniques for synthesis of examples of the disclosed complexes are described in the examples.

B. Targeting Mismatched DNA

The disclosed complexes can be used to target and detect mismatched DNA by, for example, bringing into contact a DNA sample and a $d^8$ square planar metal complex, and detecting the emission of the complex intercalated into DNA in the sample. Emission above a threshold level indicates the presence of mismatched DNA in the sample. Examples of detection of the emission of the complex intercalated into DNA are described in the examples. Generally, techniques for detecting the emission of intercalated complexes are known in the art and can be applied to the disclosed methods.

In some embodiments, the targeting and detection of mismatch DNA sites is accomplished by monitoring the significant differences in emission enhancement of Platinum (II), Palladium(II), or Gold(III) complexes toward mismatched DNA and matched DNA.

In some embodiments, the targeting and detection of mismatch DNA sites is accomplished by monitoring the gradual heat release from isothermal titration calorimetry when Platinum(II), Palladium(II), or Gold(III) complexes bind toward mismatched DNA.

In some embodiments, the targeting and detection of mismatch DNA sites is accomplished by monitoring the significant increase in melting temperature of mismatched DNA after adding Platinum(II), Palladium(II), or Gold(III) complexes.

In some embodiments, the targeting and detection of mismatch DNA sites is accomplished by monitoring the significant differences in emission enhancement of Platinum (II), Palladium(II), or Gold(III) complexes toward mismatched DNA and matched DNA; or the gradual heat release from isothermal titration calorimetry (ITC) when Platinum(II), Palladium(II), or Gold(III) complexes bind toward mismatched DNA; or the significant increase in melting temperatures of the mismatched DNA after adding Platinum(II), Palladium(II), or Gold(III) complexes.

EXAMPLES

Example 1

Preparation and Characterization of the M(II/III)Complexes

Example 1 illustrates the synthesis and characterization of the example M(II/III) complexes bearing N-heterocyclic carbene complexes or di-phosphine ligand.

Synthesis of 1

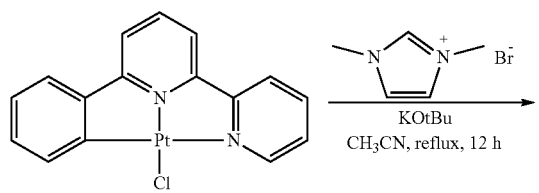

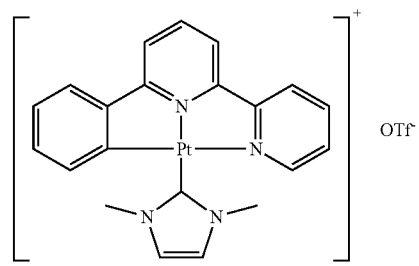

A mixture of [Pt(CNN)Cl] (50 mg, 0.108 mmol), potassium tert-butoxide (12 mg, 0.108 mmol) and 1,3-dimethyl-1H-imidazol-3-ium bromide (21 mg, 0.118 mmol) in acetonitrile (10 mL) was heated to reflux for 12 hours. After cooling to room temperature, excess silver trifluoromethanesulfonate (84 mg, 0.33 mmol) was added into reaction mixture and stirred for 30 min. After extracting the crude product into dichloromethane layer, it was purified by column chromatography on silica gel with $CH_3CN/CH_2Cl_2$ as eluent, and yellow powder was obtained.

Yield 58%; $^1$H NMR (400 MHz, $CD_3CN$): δ=8.29-8.19 (m, 3H), 8.11 (t, 1H, J=8.0 Hz), 7.99 (d, 1H, J=4.0 Hz), 7.88 (d, 1H, J=4.0 Hz), 7.63-7.56 (m, 2H), 7.34-7.26 (m, 2H), 7.12 (t, 1H, J=8.0 Hz), 7.05 (t, 1H, J=8.0 Hz), 6.58-6.36 (m, 1H), 3.82 (s, 6H); MS (FAB, +ve): m/z 522 [M-OTf]$^+$; Elemental analysis calcd (%) for $C_{22}H_{19}F_3N_4O_3PtS\cdot0.5CH_2Cl_2$: C, 37.85; H, 2.82; N, 7.85; found: C, 37.60; H, 2.80; N, 8.12.

Synthesis of 2

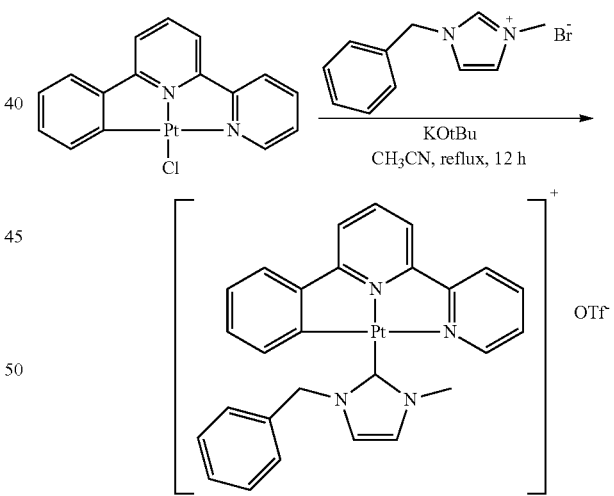

The procedure is similar to that for 1.

Yield 55%; $^1$H NMR (400 MHz, $CD_3CN$): δ=8.20-8.05 (m, 3H), 7.94 (d, 1H, J=8.0 Hz), 7.85 (d, 2H, J=8.0 Hz), 7.61-7.54 (m, 1H), 7.45-7.36 (m, 2H), 7.36-7.29 (m, 1H), 7.27-7.20 (m, 2H), 7.15-6.98 (m, 5H), 6.62-6.39 (m, 1H), 5.40 (s, 2H), 3.81 (s, 3H); MS (FAB, +ve): m/z 598 [M-OTf]$^+$; Elemental analysis calcd (%) for $C_{28}H_{23}F_3N_4O_3PtS\cdot H_2O$: C, 43.92; H, 3.29; N, 7.32; found: C, 43.90; H, 2.96; N, 7.37.

Synthesis of 3

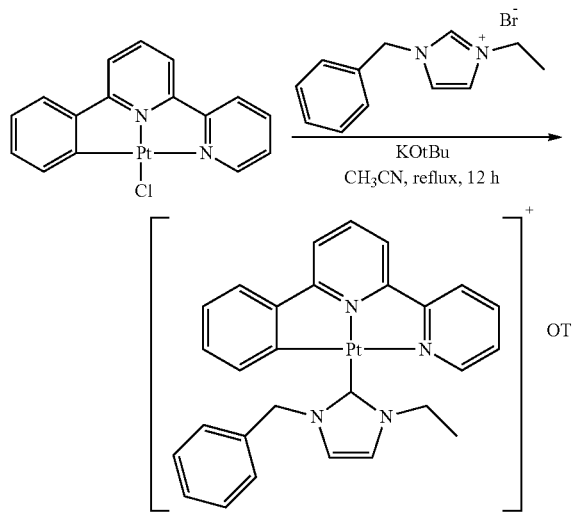

The procedure is similar to that for 1.

Yield 48%; $^1$H NMR (400 MHz, CDCl$_3$): δ=8.21-8.05 (m, 3H), 7.95 (d, 1H, J=8.0 Hz), 7.89-7.75 (m, 2H), 7.62-7.55 (m, 1H), 7.45-7.37 (m, 3H), 7.29-7.222 (m, 2H), 7.15-7.01 (m, 5H), 6.61-6.40 (m, 1H), 5.40 (s, 2H), 4.30 (m, 2H), 1.34 (t, 3H, J=8.0 Hz); MS (FAB, +ve): m/z 612 [M-OTf]$^+$; Elemental analysis calcd (%) for C$_{29}$H$_{25}$F$_3$N$_4$O$_3$PtS.H$_2$O: C, 44.67; H, 3.49; N, 7.19; found: C, 44.97; H, 3.21; N, 7.03.

Synthesis of 4

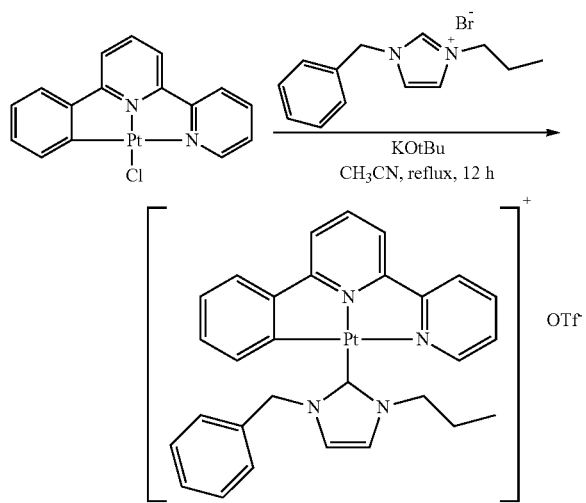

The procedure is similar to that for 1.

Yield 57%; $^1$H NMR (400 MHz, CD$_3$CN): δ=8.22-8.06 (m, 3H), 8.00-7.93 (m, 1H), 7.91-7.79 (m, 2H), 7.63-7.56 (m, 1H), 7.48-7.35 (m, 3H), 7.31-7.22 (m, 2H), 7.15-7.01 (m, 5H), 6.63-6.42 (m, 1H), 5.43 (s, 2H), 4.20 (t, 2H, J=8.0 Hz), 1.85-1.80 (m, 2H), 0.83-0.79 (t, 3H, J=8.0 Hz); MS (FAB, +ve): m/z 626 [M-OTf]$^+$; Elemental analysis calcd (%) for C$_{30}$H$_{27}$F$_3$N$_4$O$_3$PtS: C, 46.45; H, 3.51; N, 7.22; found: C, 46.39; H, 3.60; N, 7.26.

Synthesis of 5

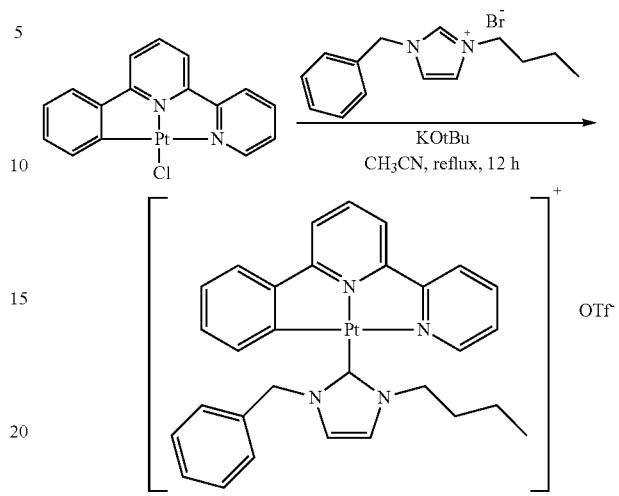

The procedure is similar to that for 1.

Yield 51%; $^1$H NMR (400 MHz, CD$_3$CN): δ=8.21-8.05 (m, 3H), 7.99-7.93 (m, 1H), 7.90-7.78 (m, 2H), 7.63-7.56 (m, 1H), 7.49-7.34 (m, 3H), 7.30-7.21 (m, 2H), 7.16-6.99 (m, 5H), 6.63-6.40 (m, 1H), 5.39 (s, 2H), 4.29-4.16 (m, 2H), 1.83-1.72 (m, 2H), 1.29-1.15 (m, 2H), 0.78-0.70 (t, 3H, J=8.0 Hz); MS (FAB, +ve): m/z 640 [M-OTf]$^+$; Elemental analysis calcd (%) for C$_{31}$H$_{29}$F$_3$N$_4$O$_3$PtS: C, 47.15; H, 3.70; N, 7.09; found: C, 47.35; H, 3.72; N, 7.09.

Synthesis of 6

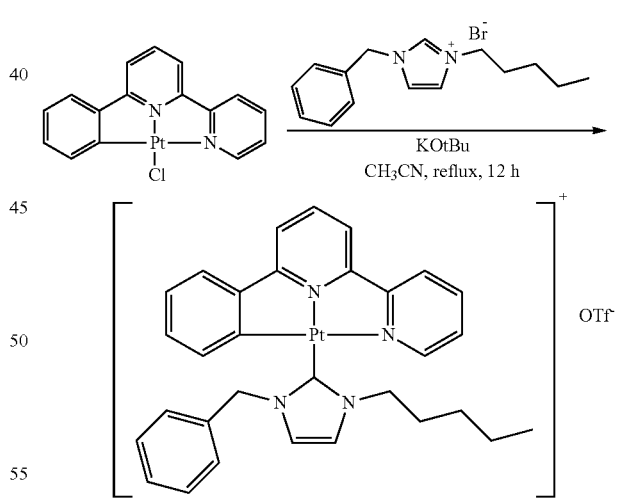

The procedure is similar to that for 1.

Yield 49%; $^1$H NMR (300 MHz, CD$_3$CN): δ=8.20-7.95 (m, 3H), 7.94-7.85 (m, 1H), 7.85-7.70 (m, 2H), 7.62-7.45 (m, 1H), 7.44-7.26 (m, 3H), 7.26-7.13 (m, 2H), 7.13-6.88 (m, 5H), 6.65-6.30 (m, 1H), 5.35(s, 2H), 4.28-4.05 (m, 2H), 1.82-1.62 (m, 2H), 1.20-0.99 (m, 4H), 0.75-0.51 (m, 3H); MS (FAB, +ve): m/z 654 [M-OTf]$^+$; Elemental analysis calcd (%) for C$_{32}$H$_{31}$F$_3$N$_4$O$_3$PtS.0.5CHCl$_3$: C, 45.21; H, 3.68; N, 6.49; found: C, 45.03; H, 3.57; N, 6.53.

Synthesis of 7

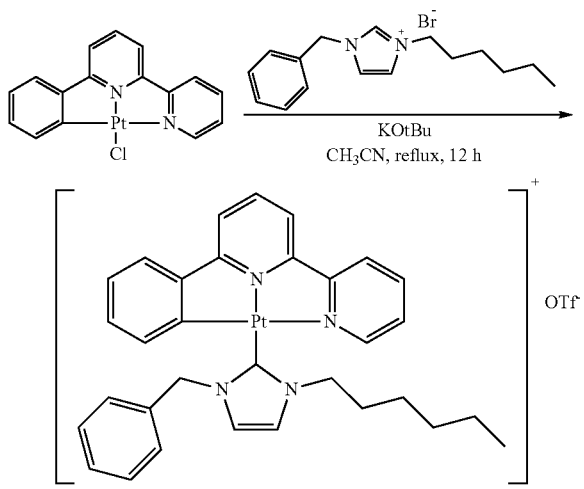

The procedure is similar to that for 1.

Yield 55%; $^1$H NMR (400 MHz, CD$_3$CN): δ=8.22-8.02 (m, 3H), 7.98-7.92 (m, 1H), 7.88-7.76 (m, 2H), 7.62-7.53 (m, 1H), 7.43-7.32 (m, 3H), 7.28-7.21 (m, 2H), 7.15-6.99 (m, 5H), 6.62-6.42 (m, 1H), 5.41-5.40 (m, 2H), 4.22 (t, 2H, J=8.0 Hz), 1.88-1.75 (m, 2H), 1.20-0.98 (m, 6H), 0.65 (t, 3H, J=12.0 Hz); MS (FAB, +ve): m/z 668 [M-OTf]$^+$; Elemental analysis calcd (%) for C$_{33}$H$_{33}$F$_3$N$_4$O$_3$PtS.0.5H$_2$O: C, 47.94; H, 4.14; N, 6.78; found: C, 47.92; H, 4.06; N 6.73.

Synthesis of 8

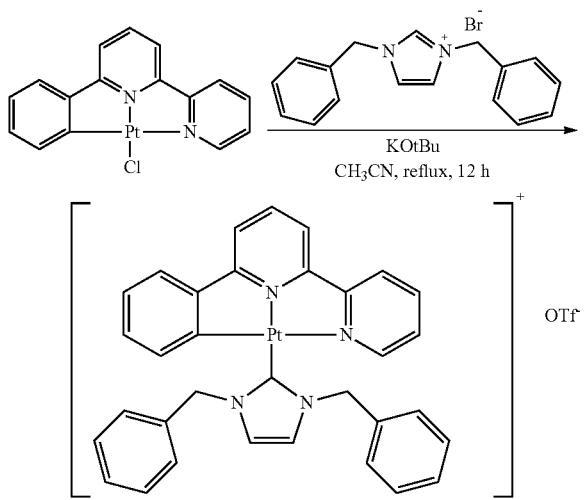

The procedure is similar to that for 1.

Yield 60%; $^1$H NMR (400 MHz, CD$_3$CN): δ=8.14-8.02 (m, 3H), 7.93 (d, 1H, J=8.0 Hz), 7.85 (d, 1H, J=8.0 Hz), 7.60 (d, 1H, J=8.0 Hz), 7.45 (s, 2H), 7.43-7.33 (m, 1H), 7.30-7.19 (m, 5H), 7.18-7.01 (m, 8H), 6.67-6.45 (m, 1H), 5.45-5.30 (m, 4H); MS (FAB, +ve): m/z 674 [M-OTf]$^+$; Elemental analysis calcd (%) for C$_{34}$H$_{27}$F$_3$N$_4$O$_3$PtS.0.5H$_2$O: C, 49.04; H, 3.39; N, 6.73; found: C, 49.03; H, 3.28; N, 6.77.

Synthesis of 9

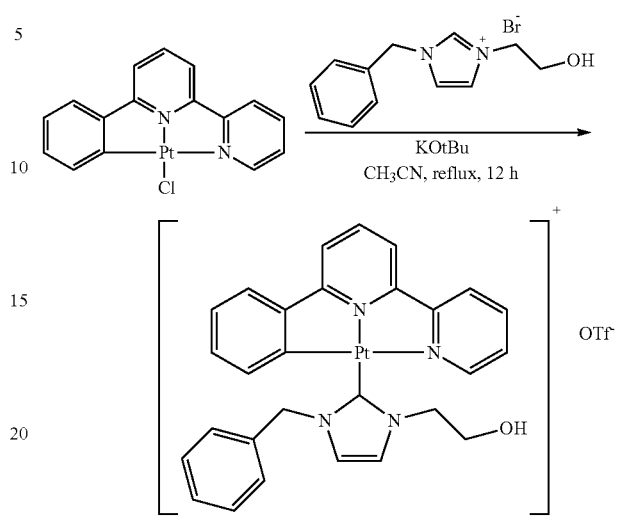

The procedure is similar to that for 1.

Yield 63%; $^1$H NMR (400 MHz, CDCl$_3$): δ=8.18-8.03 (m, 3H), 7.95 (d, 1H, J=8.0 Hz), 7.89-7.78 (m, 2H), 7.64-7.55 (m, 1H), 7.48-7.36 (m, 3H), 7.30-7.22 (m, 2H), 7.16-7.02 (m, 5H), 6.62-6.42 (m,1H), 5.44-5.41(m, 2H), 4.45-4.35 (m, 1H), 4.28-4.15 (m, 1H), 3.82-3.71(m, 2H); MS (FAB, +ve): m/z 628 [M-OTf]$^+$; Elemental analysis calcd (%) for C$_{29}$H$_{25}$F$_3$N$_4$O$_4$PtS.0.5H$_2$O: C, 44.28; H, 3.33; N, 7.12; found: C, 44.10; H, 3.12; N, 7.18.

Synthesis of 10

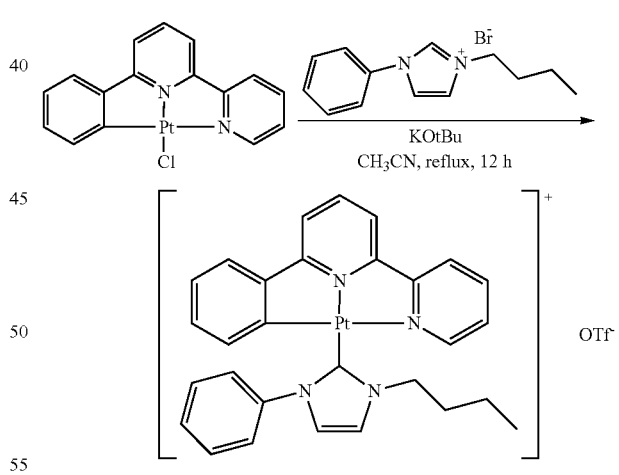

The procedure is similar to that for 1.

Yield 61%; $^1$H NMR (400 MHz, CDCl$_3$): δ=8.35-8.23 (m, 1H), 8.21-8.15 (m, 2H), 8.10-8.02 (m, 1H), 7.95-7.88 (m, 1H), 7.84-7.75 (m, 3H), 7.63-7.57 (m, 1H), 7.57-7.49 (m, 3H), 7.37-7.27 (m, 3H), 7.12-7.05 (m, 1H), 7.05-6.97 (m, 1H), 6.68-6.44 (m, 1H), 4.45-4.25 (m, 2H), 1.89-1.79 (m, 2H), 1.32-1.17 (m, 2H), 0.79-0.71 (m, 3H); MS (FAB, +ve): m/z 626 [M-OTf]$^+$; Elemental analysis calcd (%) for C$_{30}$H$_{27}$F$_3$N$_4$O$_3$PtS.H$_2$O: C, 45.40; H, 3.68; N, 7.06; found: C, 45.59; H, 3.52; N, 7.04.

Synthesis of 11

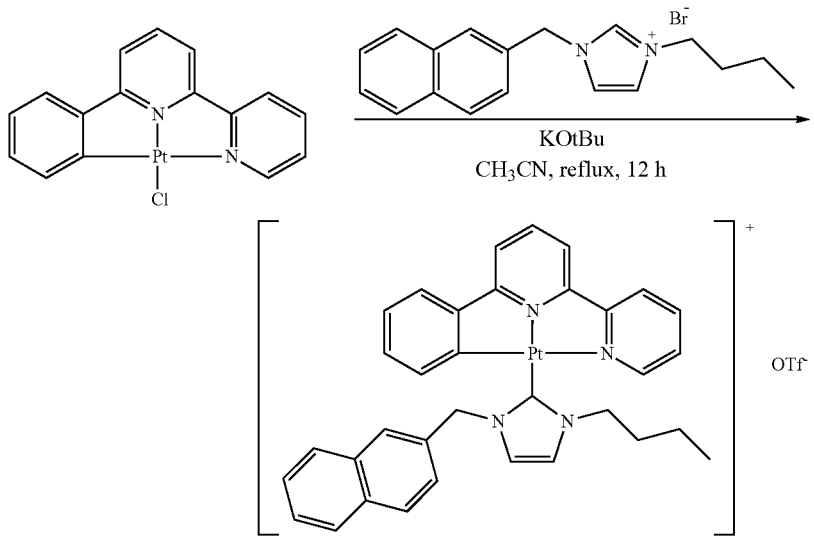

The procedure is similar to that for 1.

Yield 61%; $^1$H NMR (400 MHz, CD$_3$CN): δ=8.11-8.01 (m, 1H), 7.91-7.72 (m, 5H), 7.64-7.52 (m, 4H), 7.48-7.24 (m, 6H), 7.18-6.99 (m, 3H), 6.67-6.42 (m, 1H), 5.53-5.42 (m, 1H), 5.40-5.29 (m, 1H), 4.26-4.12 (m, 2H), 1.82-1.69 (m, 2H), 1.29-1.15 (m, 2H), 0.78-0.66 (m, 3H); MS (FAB, +ve): m/z 690 [M-OTf]$^+$; Elemental analysis calcd (%) for C$_{35}$H$_{31}$F$_3$N$_4$O$_3$PtS.H$_2$O: C, 49.01; H, 3.88; N, 6.53; found: C, 48.92; H, 3.71; N, 6.49.

Synthesis of 12

The procedure is similar to that for 1.

Yield 57%; $^1$H NMR (400 MHz, CD$_3$CN): δ=8.25-8.14 (m, 2H), 8.14-8.06 (m, 1H), 8.01-7.94 (m, 1H), 7.90-7.79 (m, 2H), 7.63-7.55 (m, 1H), 7.55-7.47 (m, 1H), 7.32-7.24 (m, 2H), 7.16-6.92 (m, 7H), 6.59-6.37 (m, 1H), 4.69-4.55 (m, 1H), 4.48-4.36 (m, 1H), 4.26-4.07 (m, 2H), 3.18-2.99 (m, 2H), 1.81-1.66 (m, 2H), 1.24-1.10 (m, 2H), 0.77-0.65 (m, 3H); MS (FAB, +ve): m/z 654 [M-OTf]$^+$; Elemental analysis calcd (%) for C$_{32}$H$_{31}$F$_3$N$_4$O$_3$PtS.H$_2$O: C, 46.77; H, 4.05; N, 6.82; found: C, 46.75; H, 3.88; N, 6.82.

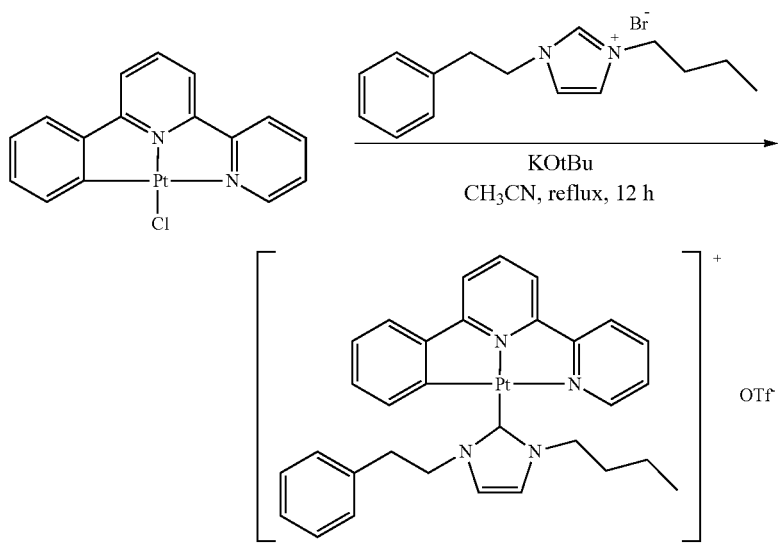

Synthesis of 13
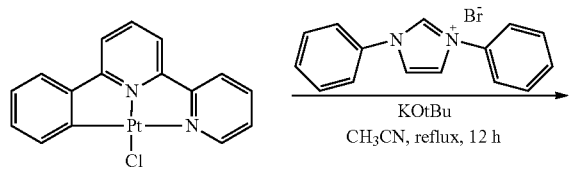
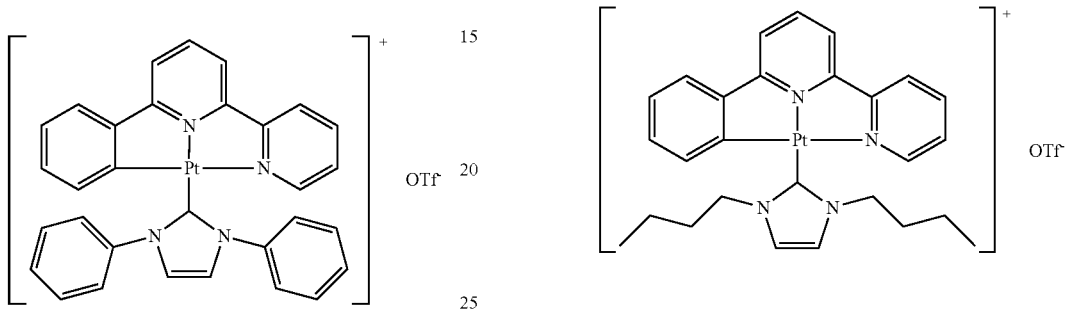
The procedure is similar to that for 1.
Yield 48%; $^1$H NMR (400 MHz, CDCl$_3$): δ=8.67-8.61 (m, 1H), 8.51-8.45 (m, 1H), 8.34-8.27 (m, 1H), 8.25-8.12 (m, 4H), 8.05-7.98 (m, 1H), 7.86-7.80 (m, 4H), 7.74-7.64 (m, 1H), 7.62-7.56 (m, 1H), 7.44-7.36 (m, 4H), 7.36-7.30 (m, 2H), 7.06-6.94 (m, 2H), 6.59-6.53 (m, 1H); MS (FAB, +ve): m/z 646 [M-OTf]$^+$; Elemental analysis calcd (%) for C$_{32}$H$_{23}$F$_3$N$_4$O$_3$PtS·0.5H$_2$O: C, 47.76; H, 3.01; N, 6.96; found: C, 47.51; H, 2.90; N, 6.93.
Synthesis of 14
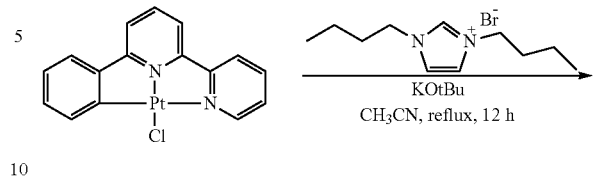
The procedure is similar to that for 1.
Yield 44%; $^1$H NMR (400 MHz, CD$_3$CN): δ=8.28-8.15 (m, 3H), 8.13-8.03 (m, 1H), 7.95 (d, 1H, J=8.0 Hz), 7.84 (d, 1H, J=8.0 Hz), 7.61-7.52 (m, 2H), 7.38-7.28 (m, 2H), 7.15-6.97 (m, 2H), 6.59-6.36 (m, 1H), 4.35-4.10 (m, 4H), 1.86-1.67 (m, 4H), 1.30-1.10 (m, 4H), 0.71 (t, 6H, J =8.0 Hz).
Synthesis of 15
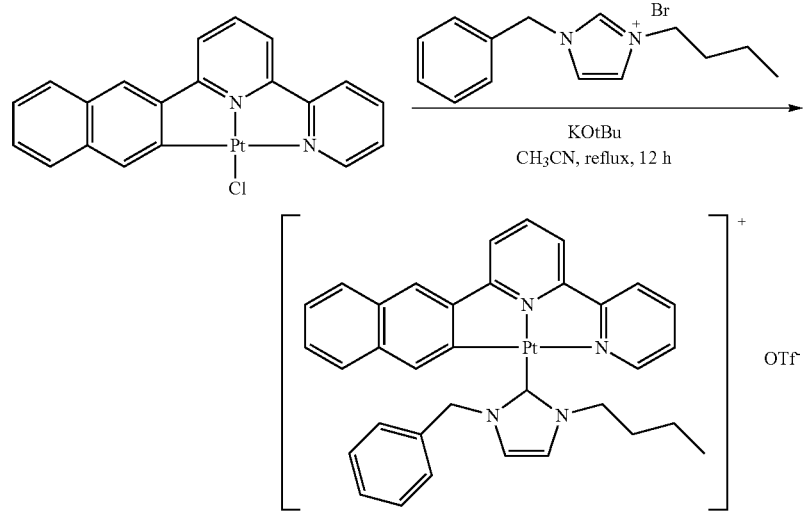

The procedure is similar to that for 1.

Yield 53%; [1]11NMR (400 MHz, CDCl₃): δ=8.27-8.10 (m, 5H), 8.08-8.02 (m, 1H), 7.91-7.81 (m, 2H), 7.59-7.53 (m, 1H), 7.51-7.37 (m, 5H), 7.31-7.24 (m, 2H), 7.11-7.00 (m, 3H), 6.96-6.90 (m, 1H), 5.47 (s, 2H), 4.28 (t, 2H, J=8.0 Hz), 1.90-1.72 (m, 2H), 1.30-1.14 (m, 2H), 0.71 (t, 3H, J=8.0 Hz); MS (FAB, +ve): m/z 606 [M-OTf]$^+$; Elemental analysis calcd (%) for $C_{28}H_3F_3N_4O_3PtS$: C, 44.50; H, 4.13; N, 7.41; found: C, 44.54; H, 4.37; N, 7.45.

Synthesis of 16

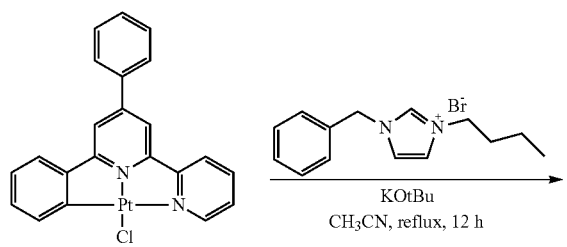

-continued

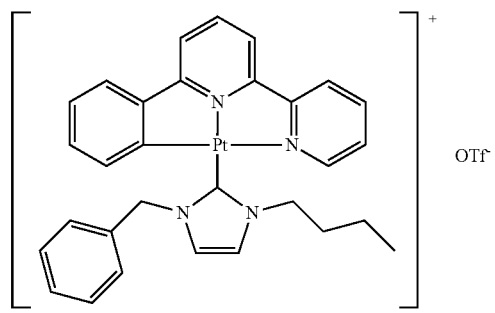

The procedure is similar to that for 1.

Yield 53%; $^1$H NMR (400 MHz, CD₃CN): δ=8.08-7.99 (m, 2H), 7.94-7.86 (m, 2H), 7.86-7.70 (m, 2H), 7.70-7.63 (m, 2H), 7.55-7.47 (m, 1H), 7.43-7.38 (m, 1H), 7.37-7.29 (m, 1H), 7.28-7.21 (m, 2H), 7.13-7.01 (m, 5H), 5.45-5.40 (m, 2H), 4.31-4.22 (m, 2H), 1.85-1.72 (m, 2H), 1.28-1.15 (m, 2H), 0.77-0.67 (m, 3H); MS (FAB, +ve): m/z 640 [M-OTf]$^+$; Elemental analysis calcd (%) for $C_{31}H_{29}F_3N_4O_3PtS \cdot 0.5H_2O$: C, 46.61; H, 3.79; N, 7.01; found: C, 46.74; H, 3.63; N, 7.09.

Synthesis of 18

The procedure is similar to that for 1.

Yield 53%; $^1$H NMR (400 MHz, CD₃CN): δ=8.36-8.30 (m, 1H), 8.24-8.09 (m, 3H), 7.98-7.91 (m, 2H), 7.91-7.82 (m, 1H), 7.77-7.71 (m, 1H), 7.66-7.56 (m, 3H), 7.48-7.35 (m, 3H), 7.30-7.23 (m, 2H), 7.19-7.02 (m, 5H), 6.66-6.44 (m, 1H), 5.43 (s, 2H), 4.30-4.22 (m, 2H), 1.88-1.76 (m, 2H), 1.32-1.17 (m, 2H), 0.81-0.71 (m, 3H); MS (FAB, +ve): m/z 716 [M-OTf]$^+$; Elemental analysis calcd (%) for $C_{37}H_{33}F_3N_4O_3PtS$: C, 51.33; H, 3.84; N, 6.47; found: C, 51.20; H, 3.88; N, 6.52.

Synthesis of 17

The procedure is similar to that for 1.

Yield: 52%. $^1$H NMR (400 MHz, CDCl3, 25° C.): 8.46 (d, J=8.0 Hz, 1 H), 8.02 -8.23 (m, 4 H), 7.71 (d, J=7.9 Hz, 1 H), 7.63-7.64 (m, 1 H), 7.53 (d, J=7.6 Hz, 1 H), 7.27 (s, 2 H), 7.14 (t, J=7.4 Hz, 1 H), 6.99 (t, J=7.5 Hz, 1 H), 6.30 (d, J=7.0 Hz, 1 H), 4.25 -4.42 (m, 4 H, —N—CH2—on -nBu), 1.84 (sextet, —CH2— on -nBu, J=7.1 Hz, 4 H), 1.28 (sextet, 4H, J=7.6 Hz, —CH2— on -nBu), 0.80 (t, J=7.3 Hz, 6 H, —CH3 on -nBu); $^{31}$P NMR (400 MHz, CD3CN): −144.14. 19F NMR (400 MHz, CD3CN): −73.66; MS (FAB, +ve): m/z 517 [M-OTf]$^+$; Elemental Analysis, calcd: C, 50.34; H, 4.83; N, 8.39; found: 50.46; H, 4.96; N, 8.18.

Synthesis of 19

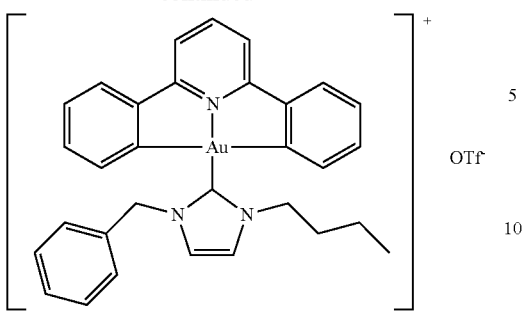

The procedure is similar to that for 1.

Yield 53%; $^1$H NMR (400 MHz, CD$_3$CN): δ=8.15-8.05 (m, 1H), 7.82-7.72 (m, 4H), 7.62-7.55 (m, 2H), 7.38-7.28 (m, 2H), 7.28-7.22 (m, 2H), 7.21-7.15 (m, 2H), 7.13-7.05 (m, 3H), 6.97-6.89 (m, 2H), 5.34 (s, 2H), 4.18-4.14 (m, 2H), 1.79-1.76 (m, 2H), 1.25-1.19 (m, 2H), 0.76-0.73 (m, 3H).

Synthesis of 20

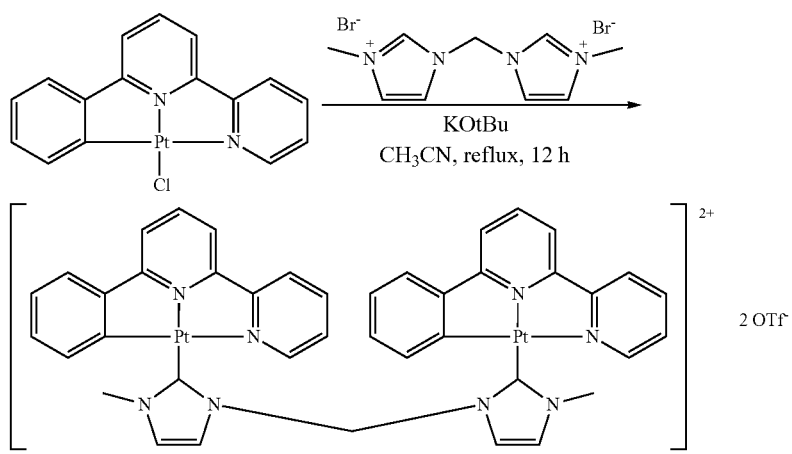

A mixture of [Pt(CNN)Cl] (50 mg, 0.108 mmol), potassium tert-butoxide (12 mg, 0.108 mmol), and 1,1'-methylenebis(3-methyl-1H-imidazol-3-ium) bromide (18.3 mg, 0.054 mmol) in acetonitrile (15 mL) was heated to reflux for 12 hours. After cooling to room temperature, excess silver trifluoromethanesulfonate (84 mg, 0.33 mmol) was added into reaction mixture and stirred for 30 mins. After extracting the crude product into dichloromethane layer, it was purified by column chromatography on silica gel with CH$_3$CN/CH$_2$Cl$_2$ as eluent, and yellow powder was obtained.

Yield 58%; $^1$H NMR (400 MHz, CD$_3$CN): δ=8.02-7.90 (m, 4H), 7.87-7.78 (m, 6H), 7.58 (d, 2H, J=8.0 Hz), 7.45 (d, 2H, J=8.0 Hz), 7.42-7.36 (m, 2H), 7.16-7.08 (m, 4H), 6.92-6.81 (m, 4H), 6.71-6.62 (m, 2H), 6.41-6.18 (m, 2H), 3.55 (s, 6H); MS (FAB, +ve): m/z 1028 [M-2OTf+1]$^+$; Elemental analysis calcd (%) for C$_{43}$H$_{34}$F$_6$N$_8$O$_6$Pt$_2$S$_2$: C, 38.92; H, 2.58; N, 8.44; found: C, 38.75; H, 2.61; N, 8.44.

Synthesis of 21
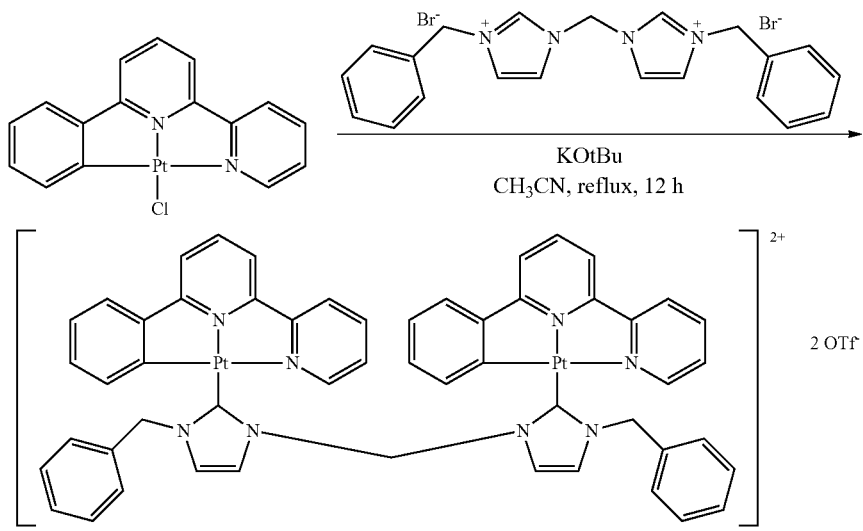
The procedure is similar to that for 20.
Yield 47%; 1H NMR (400 MHz, CD$_3$CN): δ=8.02-7.88 (m, 6H), 7.87-7.78 (m, 4H), 7.62-7.55 (m, 2H), 7.48-7.39 (m, 4H), 7.15-7.08 (m, 4H), 7.08-7.02 (m, 10H), 6.95-6.89 (m, 2H), 6.89-6.82 (m, 2H), 6.73-6.64 (m, 2H), 6.42-6.36 (m, 2H), 5.32-5.12 (m, 4H); MS (FAB, +ve): m/z 1278 [M-2OTf+1]$^+$; Elemental analysis calcd (%) for C$_{63}$H$_{46}$F$_6$N$_8$O$_6$Pt$_2$S$_2$: C, 47.91; H, 2.94; N, 7.09; found: C, 47.66; H, 3.01; N, 7.22.
Synthesis of 22
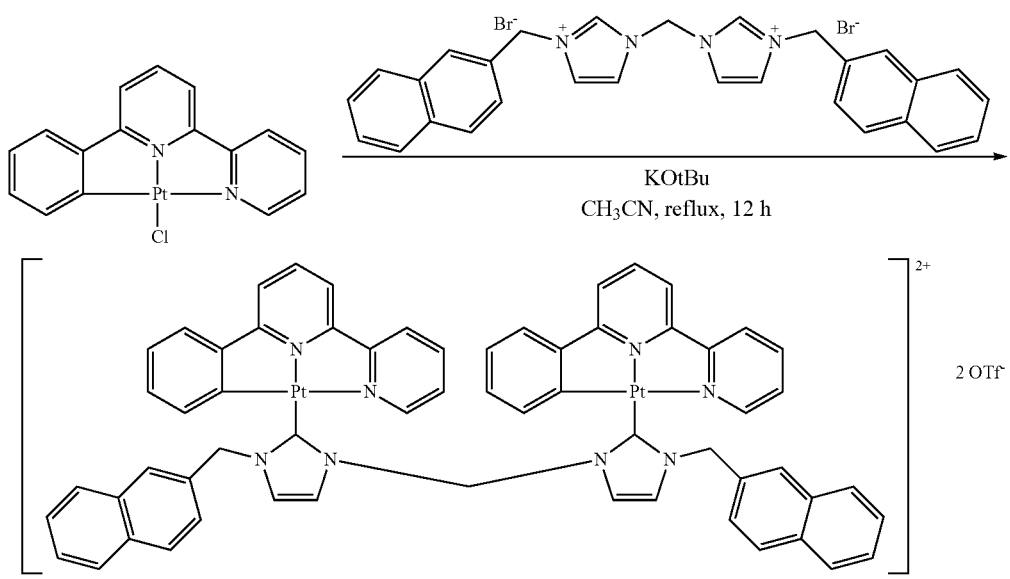
The procedure is similar to that for 20.
Yield 37%; 1H NMR (400 MHz, CD$_3$CN): δ=7.95-7.80 (m, 6H), 7.75-7.55 (m, 6H), 7.55-7.36 (m, 10H), 7.36-7.22 (m, 6H), 7.18-7.12 (m, 2H), 7.11-7.03 (m, 2H), 7.02-6.95 (m, 2H), 6.91-6.82 (m, 4H), 6.76-6.68 (m, 2H), 6.58-6.29 (m, 2H), 5.48-5.38 (m, 2H), 5.28-5.19 (m, 2H); MS (FAB, +ve): m/z 1278 [M-OTf]+.

Synthesis of 23

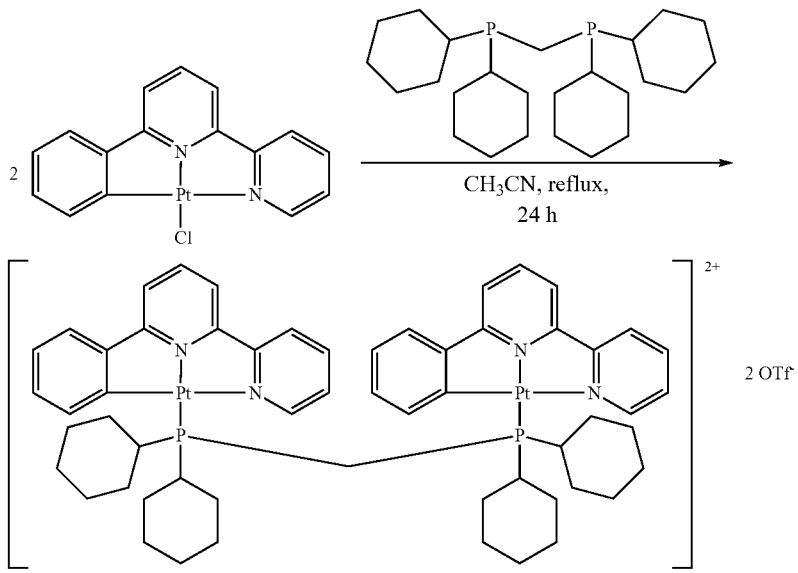

A mixture of [Pt(CNN)Cl] (50 mg, 0.108 mmol) and bis(dicyclohexylphosphino)methane (22 mg, 0.054 mmol) in acetonitrile (15 mL) was heated to reflux for 24 hours. After cooling to room temperature, excess silver trifluoromethanesulfonate (84 mg, 0.33 mmol) was added into reaction mixture and stirred for 30mins. After extracting the crude product into dichloromethane layer, it was purified by column chromatography on silica gel with $CH_3CN/CH_2Cl_2$ as eluent, and reddish orange powder was obtained.

Yield 41%; $^1$H NMR (400 MHz, $CD_3CN$): δ=8.06-7.82 (m, 4H), 7.82-7.71 (m, 4H), 7.71-7.55 (m, 4H), 7.48-7.11 (m, 8H), 7.03-6.88 (m, 2H), 5.44 (s, 2H), 3.36-0.65 (m, 44H); MS (FAB, +ve): m/z 1261 [M-2OTf+1]$^+$; Elemental analysis calcd (%) for $C_{59}H_{68}F_6N_4O_6P_2Pt_2S_2$: C, 45.44; H, 4.40; N, 3.59; found: C, 45.39; H, 4.53; N, 3.40.

Synthesis of 24

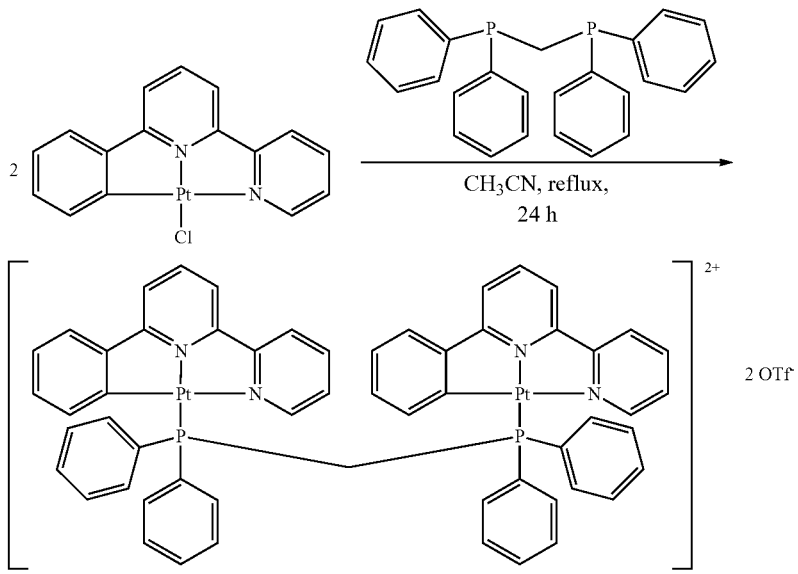

The procedure is similar to that for 23.

Yield 41%; 1H NMR (400 MHz, CD$_3$CN): δ=8.40-8.02 (m, 4H), 7.90-7.88 (m, 4H), 7.88-7.75 (m, 6H), 7.68-7.60 (m, 2H), 7.52-7.31 (m, 14H), 7.00-6.88 (m, 2H), 6.78-6.60 (m, 4H), 6.52-6.35 (m, 4H), 6.25-6.10 (m, 2H), 4.95-4.71 (m, 2H); MS (FAB, +ve): m/z 1237 [M-2OTf+1]$^+$; Elemental analysis calcd (%) for C$_{59}$H$_{44}$F$_6$N$_4$O$_6$P$_2$Pt$_2$S$_2$·CH$_2$Cl$_2$: C, 44.48; H, 2.86; N, 3.46; found: C, 44.68; H, 2.94; N, 3.63.

Example 2

Emission Enhancement of Pt(II)-NHC Complexes and Pt(II)-Phosphine Complexes towards Mismatched, Abasic and Well-matched DNA Example 2 describes the result of studies showing that examples of the disclosed complexes, complex 5 and complex 23, revealed a greater emission enhancement towards CC mismatched and abasic DNA when compared to the enhancement toward well-matched DNA.

A. Pt(II)-NHC Complexes

Figure 1B:
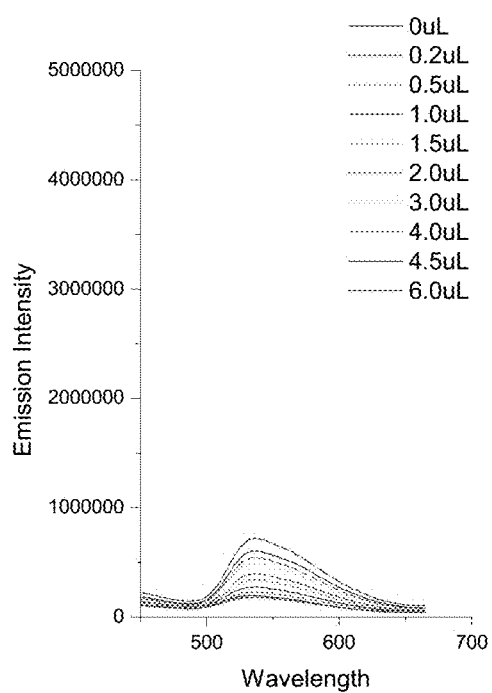
Figure 2:
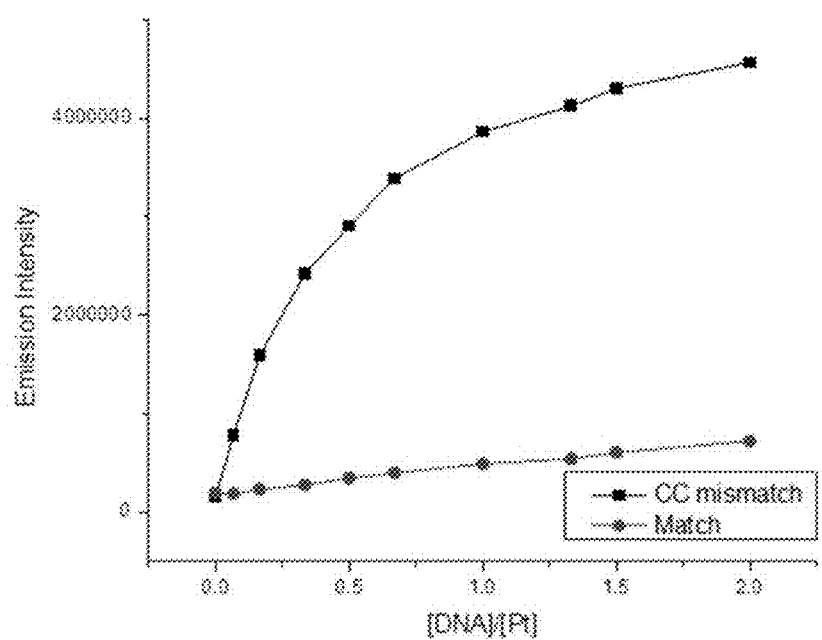
FIG. 2 is a graph showing changes in emission intensity at 536 nm of complex 5 (5 μM) in the aqueous buffer solution upon titrations with the DNAs.

The emission spectrum of complex 5 in an aqueous buffer solution (50 mM NaCl, 2 mM Tris, pH 7.5) revealed an emission band centered at 536 nm. Upon addition of CC mismatch DNA, a growth of the emission band was observed, and a 27-fold increase in emission intensity was found when the concentration of CC mismatched DNA was twice as much as that of the concentration of complex 5 (FIGS. 1A and 1B). It is noteworthy that the emission enhancement of complex 5 towards CC mismatched DNA was around 7-fold more than that toward matched DNA (FIG. 2). This indicates that complex 5 can be used as a specific probe for targeting DNA containing CC mismatch site.

In order to gain more insights on the binding events of platinum(II) complexes with mismatched DNAs, platinum (II) C^N^N complexes with different alkyl chain lengths or functional groups on the N-heterocyclic carbene ligands have been synthesized and studied for their interactions with mismatched DNAs.

1. Effects of Different Lengths of Alkyl Chain of on the Binding toward Mismatched DNA The ratio in emission enhancement of the complexes by CC mismatched DNA, $\Delta I_{cc}$, to the enhancement by matched DNA, $\Delta I_{mat}$, was found to be larger upon increasing the alkyl chain length from one to four carbons, but a decrease in the ratio was observed by increasing the chain length from four to six carbons (FIG. 3), i.e. complex 5 with four carbons on the alkyl chain showed the greatest difference in the emission enhancement which accounted for 7-folds between CC mismatched DNA and well-matched DNA. On the other hand, complexes with short alkyl chains were found to show significant emission enhancements with both CC mismatched and the well-matched DNA, while complexes with longer carbon chains showed smaller emission enhancements in the presence of either mismatched or matched DNA (FIG. 4).The lack in specificity toward CC mismatched DNA by complexes with short carbon chains can be attributed to their low steric hindrance, thus facilitating the binding of the complexes toward matched DNA. For the complexes with long alkyl chains, they may not fit well into the binding pocket of the mismatch site, so small emission enhancement was recorded with mismatched or matched DNA. In summary, complex 5, which has a suitable size to bind onto mismatched DNA but not the matched DNA, shows good discrimination of CC mismatched DNA from well-matched DNA.

2. Effects of Different Functional Groups on the Binding toward Mismatched DNA

Figure 3:
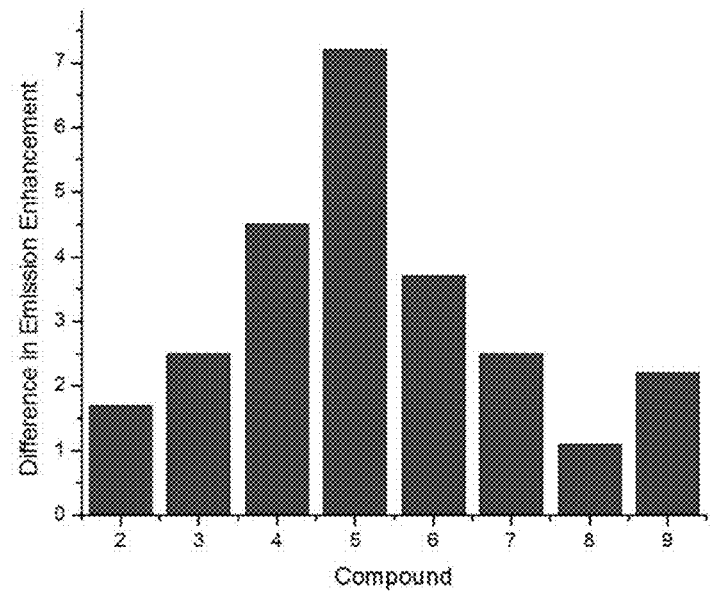
FIG. 3 is a graph showing the difference in emission enhancement between CC mismatched DNA and matched DNA by different complexes.
Figure 4:
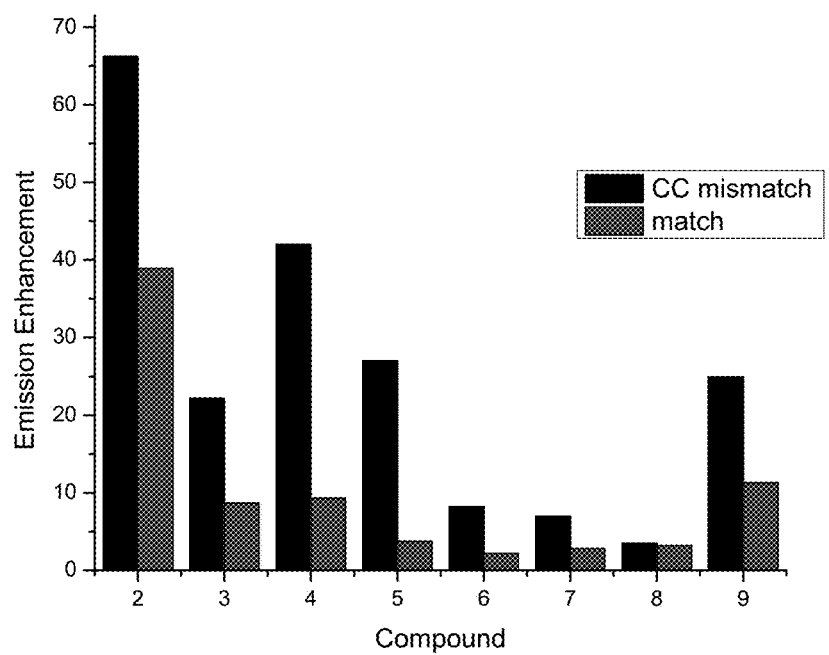
FIG. 4 is a graph showing the emission enhancement of different complexes (5 μM) towards CC mismatched DNA and matched DNA (10 μM).

Different functionalities on the NHC ligands were found to show profound effects on the binding of the platinum(II) C^N^N complexes toward mismatched DNA and hence the emission enhancement (FIG. 3). Complexes 8 and 9, which has a benzyl and (2-hydroxy)ethyl group respectively, in place of the butyl group on complex 5, showed smaller ratios of emission enhancement by CC mismatched DNA to the enhancement by matched DNA than complex 5 (FIG. 3). The high steric bulkiness of the former complex probably disfavours its binding toward both mismatched and matched DNA, leading to small emission enhancements in the presence of the DNAs (FIG. 4). For complex 9, the small ratio can be attributed to its strong binding toward matched DNA, resulting in strong emission enhancement. This suggests that the introduction of a hydroxyl group onto NHC ligand may not help in improving the specificity toward mismatched DNA.

Figure 5:
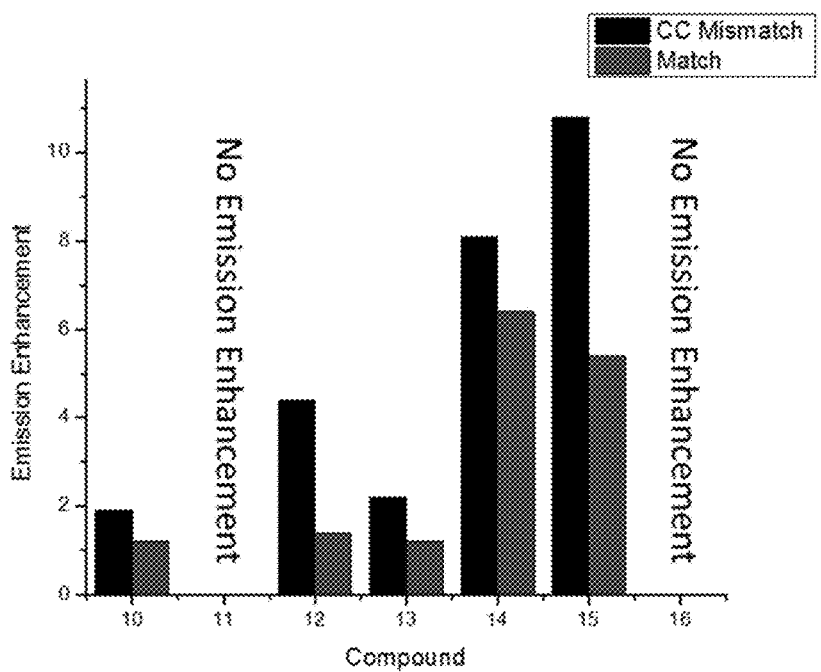
FIG. 5 is a graph showing the difference in emission enhancement between CC mismatched DNA and matched DNA by different complexes.
Figure 6:
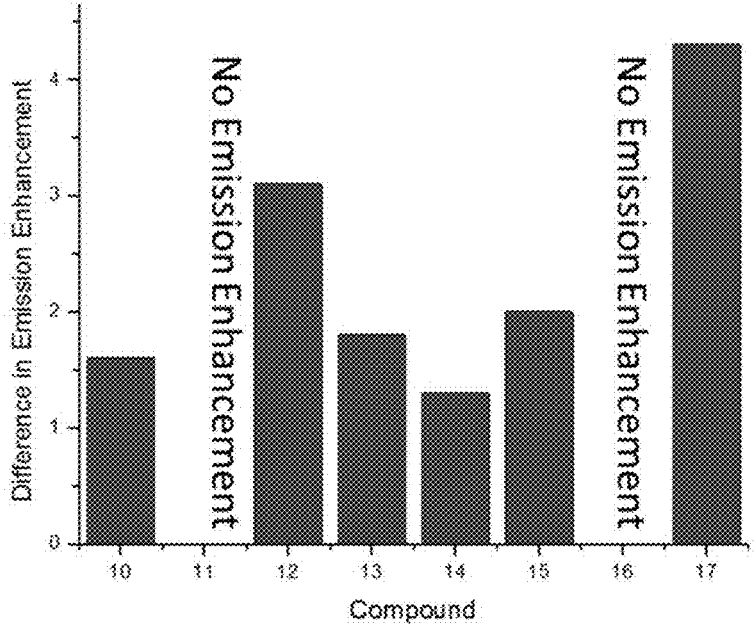
FIG. 6 is a graph showing the emission enhancement of different complexes (5 μM) towards CC mismatched DNA and matched DNA (10 μM).

3. Effects of Different Aromatic Substituent on the Binding toward Mismatched DNA The emission spectroscopic study on complexes 10-16 with CC mismatched and matched DNA demonstrated smaller $\Delta I_{cc}/\Delta I_{mat}$ than that of complex 5, with no emission enhancement observed for complexes 11 and 16 (FIG. 5). Complexes 10-12 differ from complex 5 by the aromatic substituent on the NHC ligand. It was found that increasing the size of the aromatic substituent led to small emission enhancements for both match and mismatch DNA, suggesting that the increase in steric bulkiness would prohibit the binding of the complexes toward the DNAs. On the other hand, complex 16 contains an additional phenyl ring on the C^N^N ligand. Since the phenyl ring is not coplanar with the C^N^N ligand, no significant strengthening of the π-stacking interaction between the extend C^N^N ligand and DNA bases would be anticipated, and indeed the extra phenyl ring can contribute to a higher steric bulkiness of the complex. Therefore, no good DNA binding and no emission enhancement of complex 16 can be observed in the presence of the DNAs (FIGS. 5 and 6). For complex 14, it showed significant emission enhancements that reflect good binding affinity toward both mismatch and match DNA. This can be explained by the low steric hindrance of its NHC ligand which contains two methyl groups.

These results indicate that an NHC ligand with a certain degree of steric bulkiness is better for good specificity toward a mismatch site because such a steric bulkiness could impose an energetic cost for forcing apart the stacked, well-matched DNA prior to the DNA binding. As a result, the binding of platinum(II) complexes onto mismatched DNA would be thermodynamically more favourable and hence a higher binding constant, as compared to the binding of matched DNA, can be achieved.

4. Effects of Dinuclear Metal Complexes on the Binding toward Mismatched DNA

Figure 7:
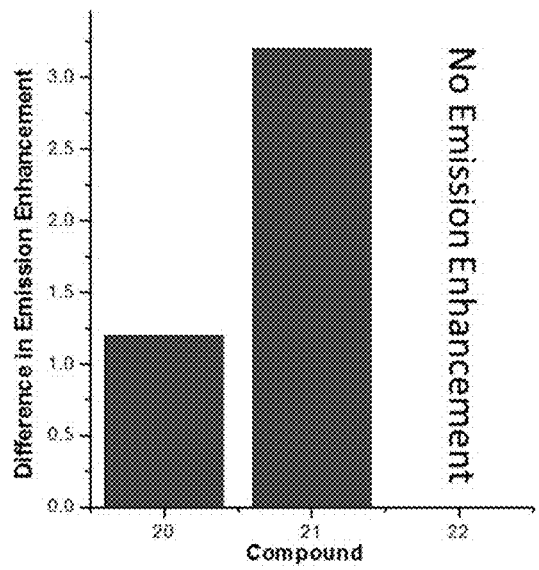
FIG. 7 is a graph showing the difference in emission enhancement between CC mismatched DNA and matched DNA by different complexes.
Figure 8A:
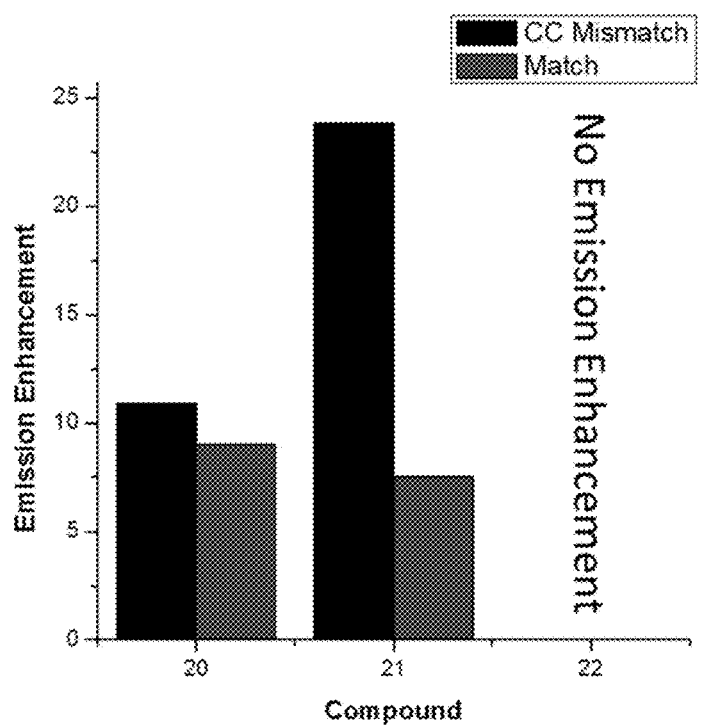
FIGS. 8A and 8B are graphs showing the emission enhancement of different complexes (5 μM) towards CC mismatched DNA and matched DNA (10 μM).
Figure 8B:
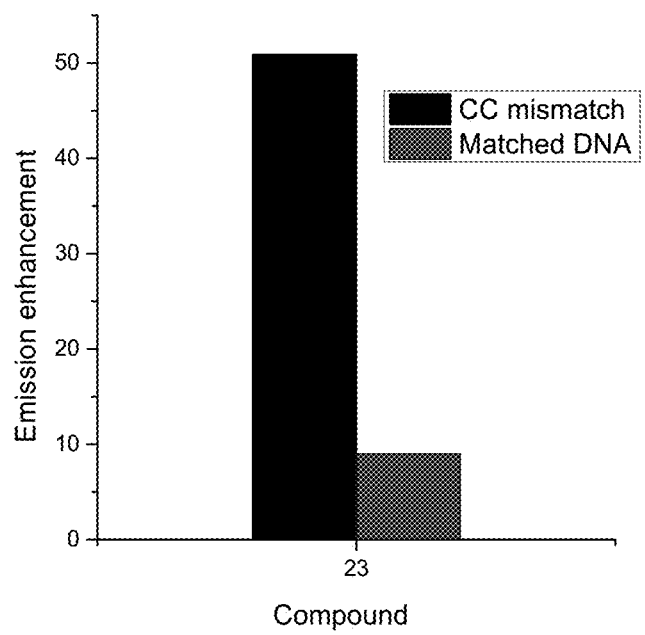
Figure 9A:
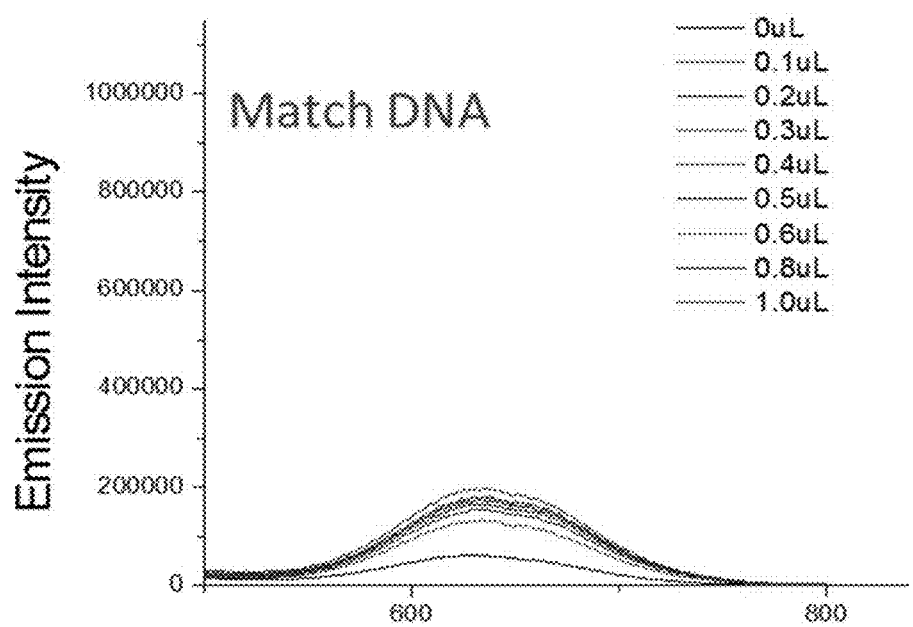
FIGS. 9A, 9B, 9C, and 9D are graphs showing the emission spectra of complex 23 (5 μM) in an aqueous buffer solution (50 mM NaCl, 2 mM Tris, pH 7.5) after binding to different concentrations of well-matched DNA (upper left), CC mismatched DNA (upper right), DNA with abasic site (bottom left) and DNA with single base bulges (bottom right).
Figure 9B:
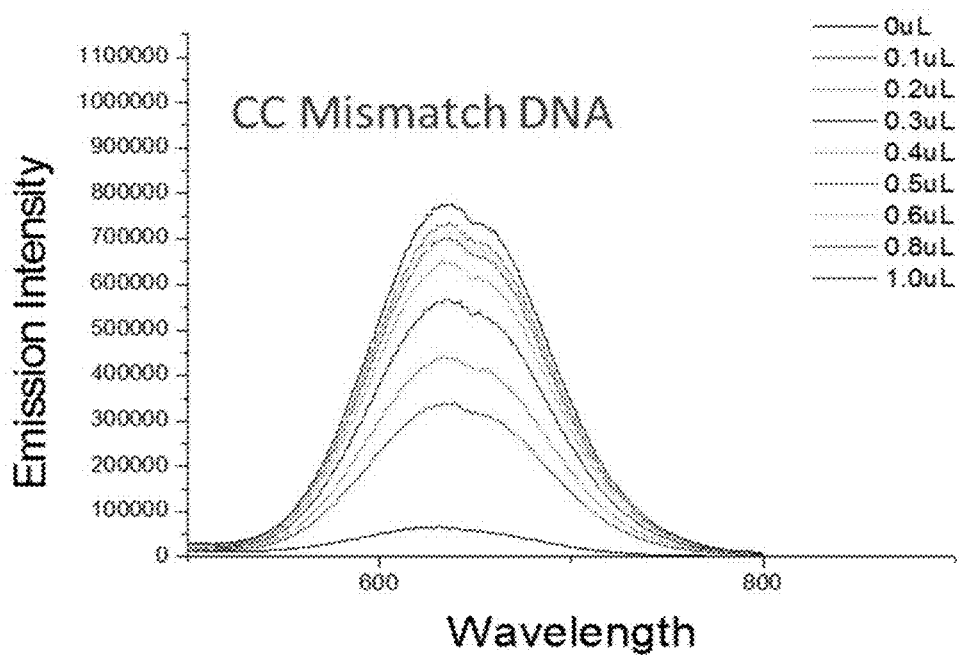
Figure 9C:
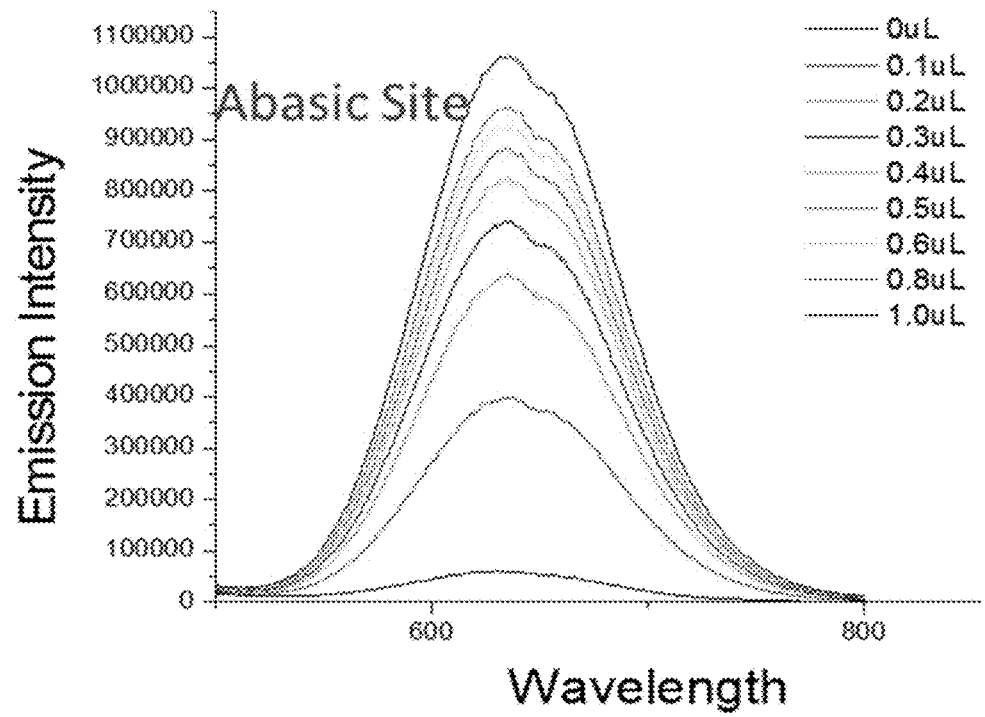
Figure 9D:
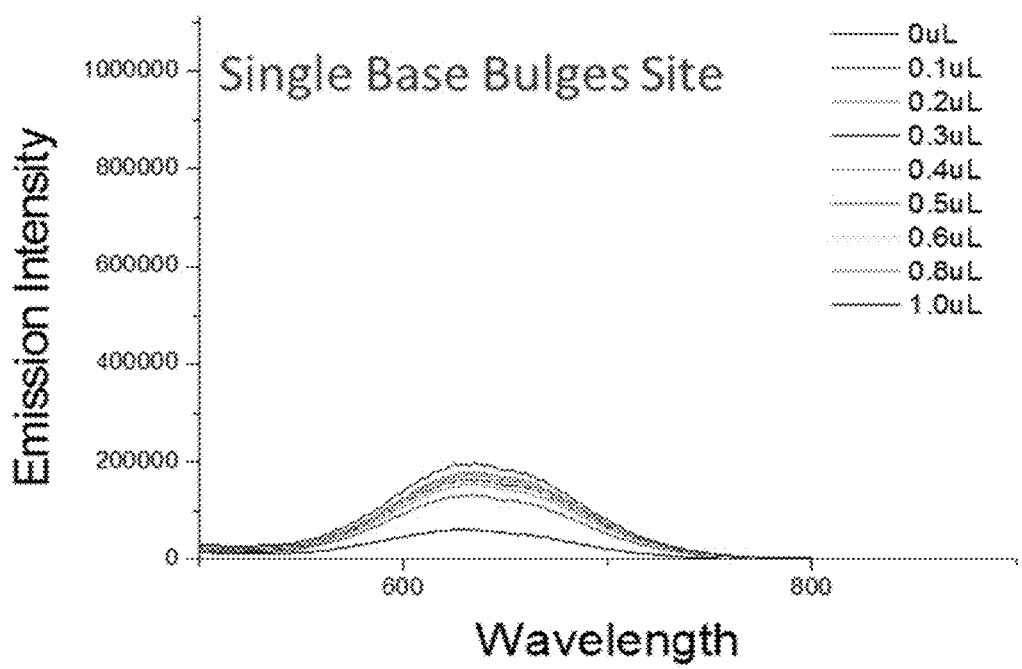

Dinuclear metal complexes also showed good selectively toward CC mismatched DNA. Among complexes 20-22, complex 21 exhibited the highest difference in emission enhancement between CC mismatch DNA and match DNA, i.e. largest $\Delta I_{cc}/\Delta I_{mat}$ value (FIG. 7). It may be due to its steric bulkiness imposing energetic cost on well-matched DNA binding. On the other hand, complex 20 revealed similar emission enhancement after binding toward both CC mismatched and matched DNA. The low selectivity could be attributed to the small size of methyl group, so that complex 20 showed similar binding affinity toward mismatched and well-matched DNA.

B. Pt(II)-Phosphine Complexes

Apart from Pt(II)-NHC complexes, Pt(II) complexes with di-phosphine ligands were also found to exhibit higher emission enhancement towards CC mismatched DNA than matched DNA. In addition, the emission intensity of Pt(II)-phosphine complexes towards DNA containing abasic site and single base bulge was also examined.

Figure 10:
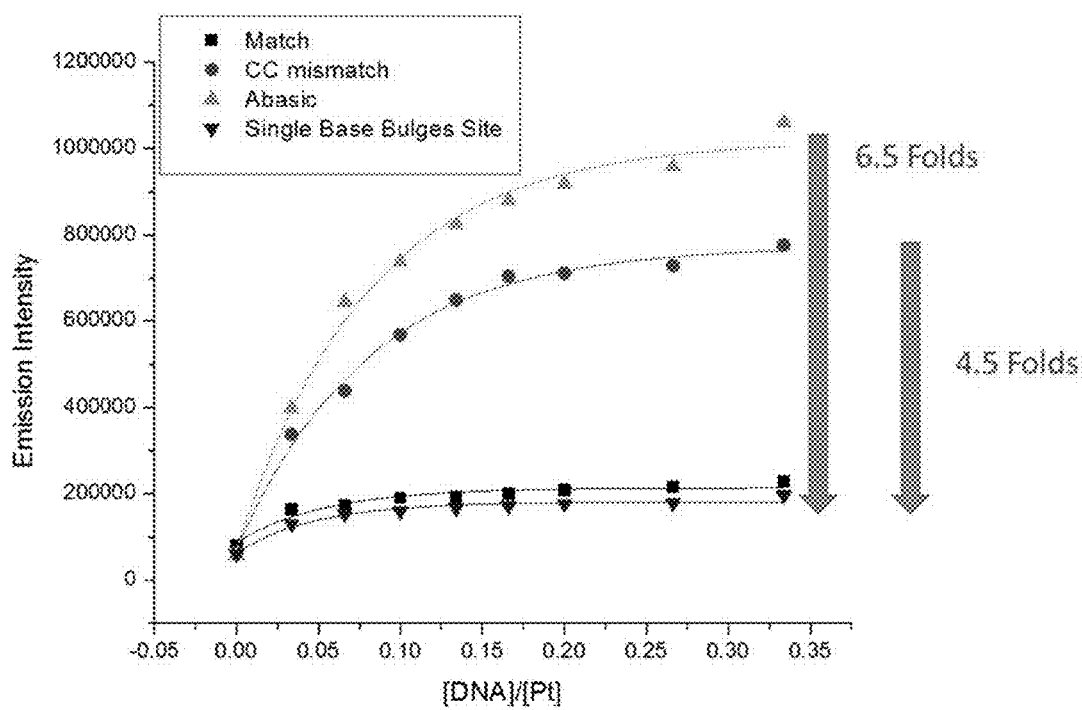
FIG. 10 is a graph showing changes in emission intensity at 618 nm of complex 23 (5 μM) in the aqueous buffer solution upon titrations with different types of double strand DNAs.

The emission spectrum of complex 23 in an aqueous buffer solution (50 mM NaCl, 2 mM Tris, pH 7.5) revealed an emission band centered at 615 nm. A 2.8, 3.2, and 12.1-fold increase in emission intensity of complex 23 was found in the presence of matched DNA, and DNA with single base bulges and CC mismatched DNA respectively (FIGS. 9A, 9B, 9C, and 9D). Interestingly, a more significant increase in emission intensity of 18.3-fold was observed upon addition of DNA containing abasic site (FIGS. 9A, 9B, 9C, and 9D). The remarkable difference (~6.5-fold) in emission enhancement of complex 23 found in the presence of DNA with abasic site from that of matched DNA (FIG. 10) indicates that complex 23 can be used as a specific probe for targeting DNA containing abasic site.

Example 3

Specific Binding of Pt(II) Complexes towards CC Mismatched DNA

Example 3 demonstrates the specific binding of Pt(II) complexes towards CC mismatched DNA as revealed by isothermal titration calorimetry(ITC).

ITC measures the heat absorbed or generated during a bi-molecular binding event. During ITC experiment of titrating known concentration of titrant (DNA molecules) to known quantity of titrate (Pt(II) complexes), Pt(II) complexes would bind onto the DNA molecules, generating incremental heat changes (in the unit of microcalories (μcal)). Through accurate measurement of the heat changes in each step of the titration and fitting the data by using a non-liner least square method, the best-fitted graph would yield the binding constant (K) of the bi-molecular interaction.

Figure 11:
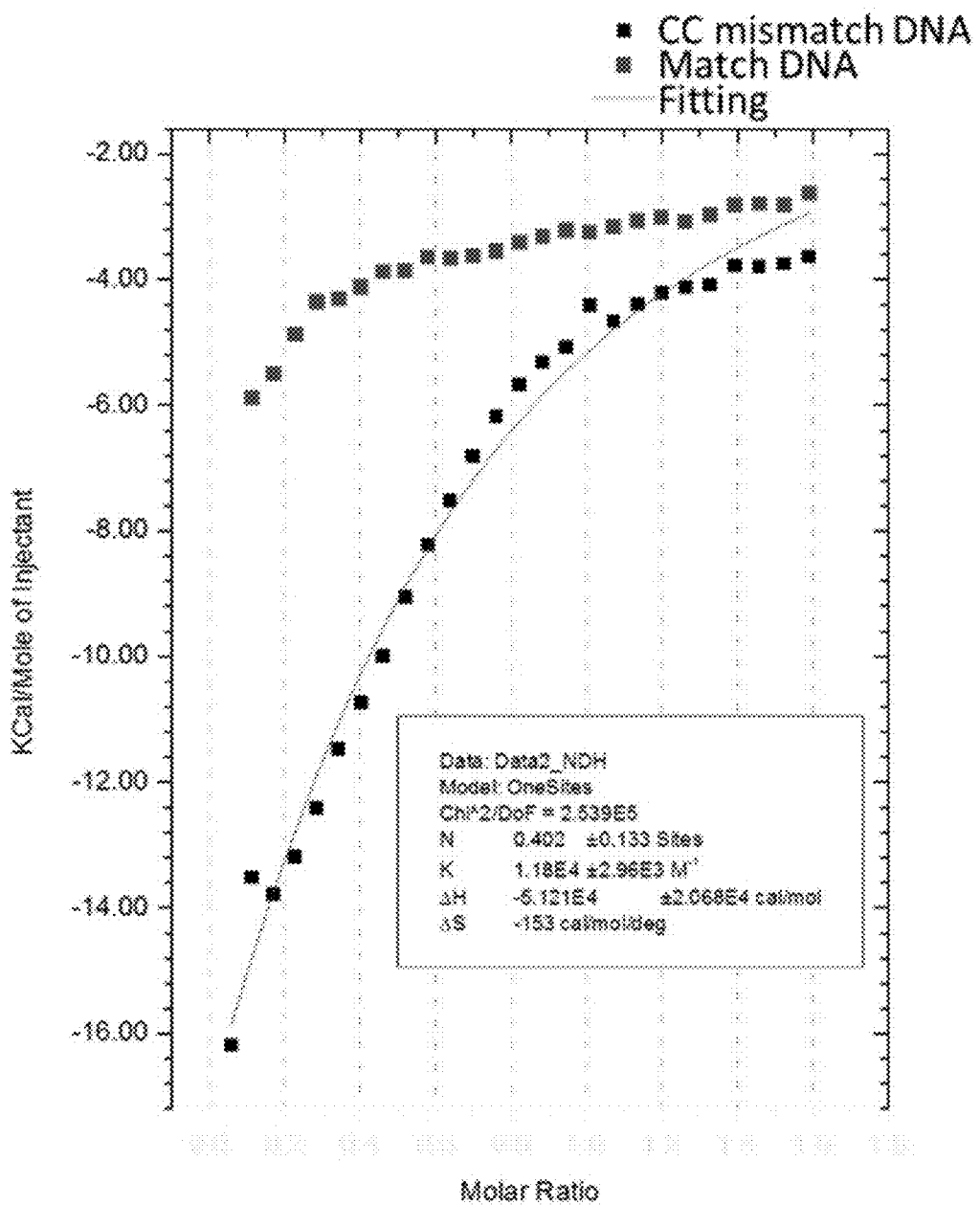
FIG. 11 is a graph showing heat release from titrating 0.75 mM of CC mismatched DNA and well-matched DNA into 0.1 mM of complex 5 in an aqueous buffer solution (50 mM NaCl, 2 mM Tris, pH 7.5).
Figure 12:
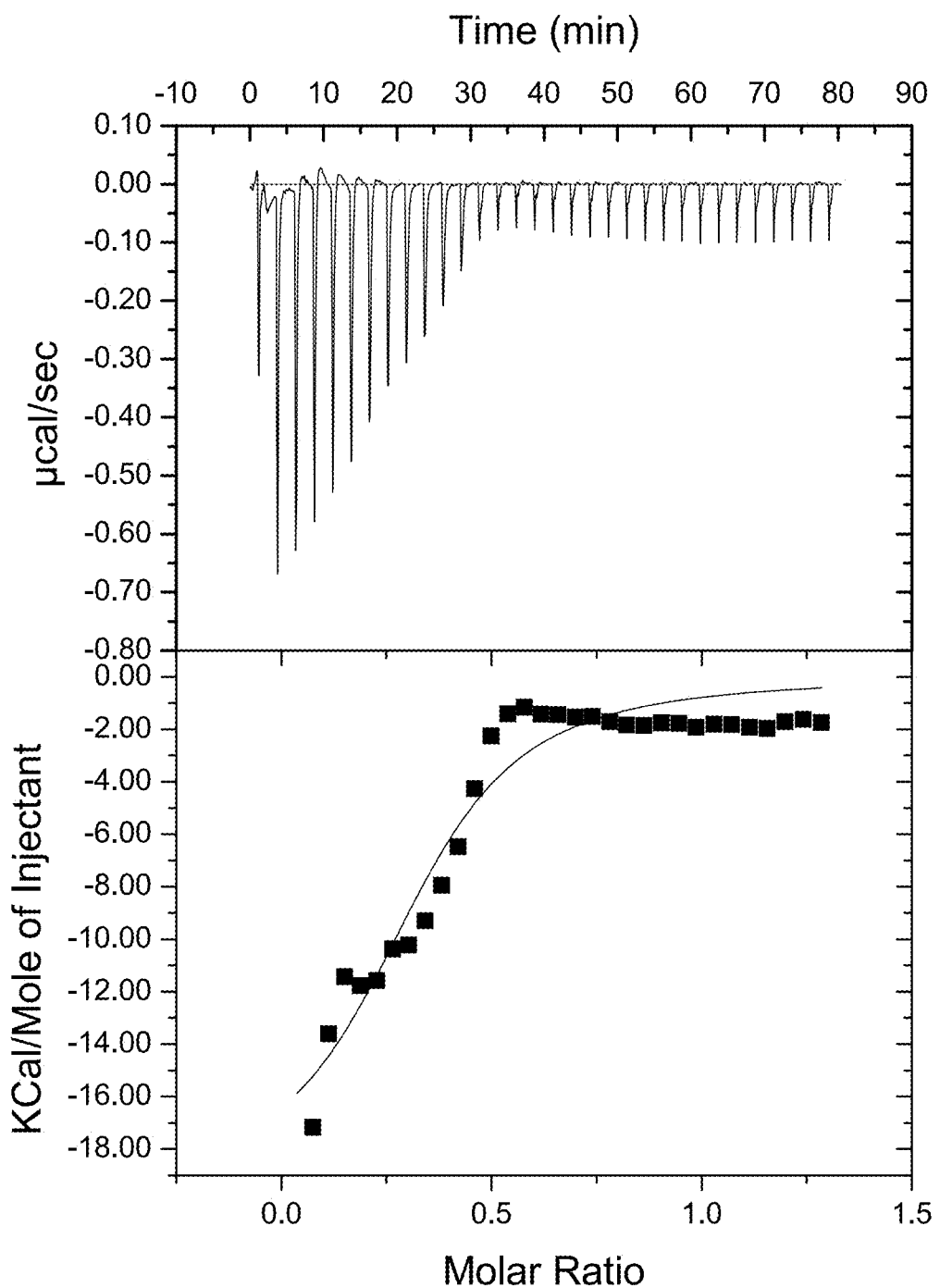
FIG. 12 is a graph showing heat release from titrating 0.75 mM of CC mismatched DNA into 0.1 mM of complex 23 in an aqueous buffer solution (50 mM NaCl, 2 mM Tris, pH 7.5).

To determine the binding constant of Pt(II) complexes with CC mismatched DNA, 0.1 mM of Pt(II) complex in an aqueous buffer solution (50 mM NaCl, 2 mM Tris, pH 7.5) was titrated by 0.75 mM of DNA. Heat released from each step of titration had been recorded. It was found that the binding constants of complex 5 and complex 23 with CC mismatched DNA were $1.18 \times 10^4$ and $1.42 \times 10^5$ respectively (FIGS. 11 and 12). However, no significant heat change in the binding of matched DNA with complex 5 or 23 was observed. This indicates that complex 5 and 23 have a stronger specific binding towards CC mismatch site than that towards well-matched site.

Figure 13A:
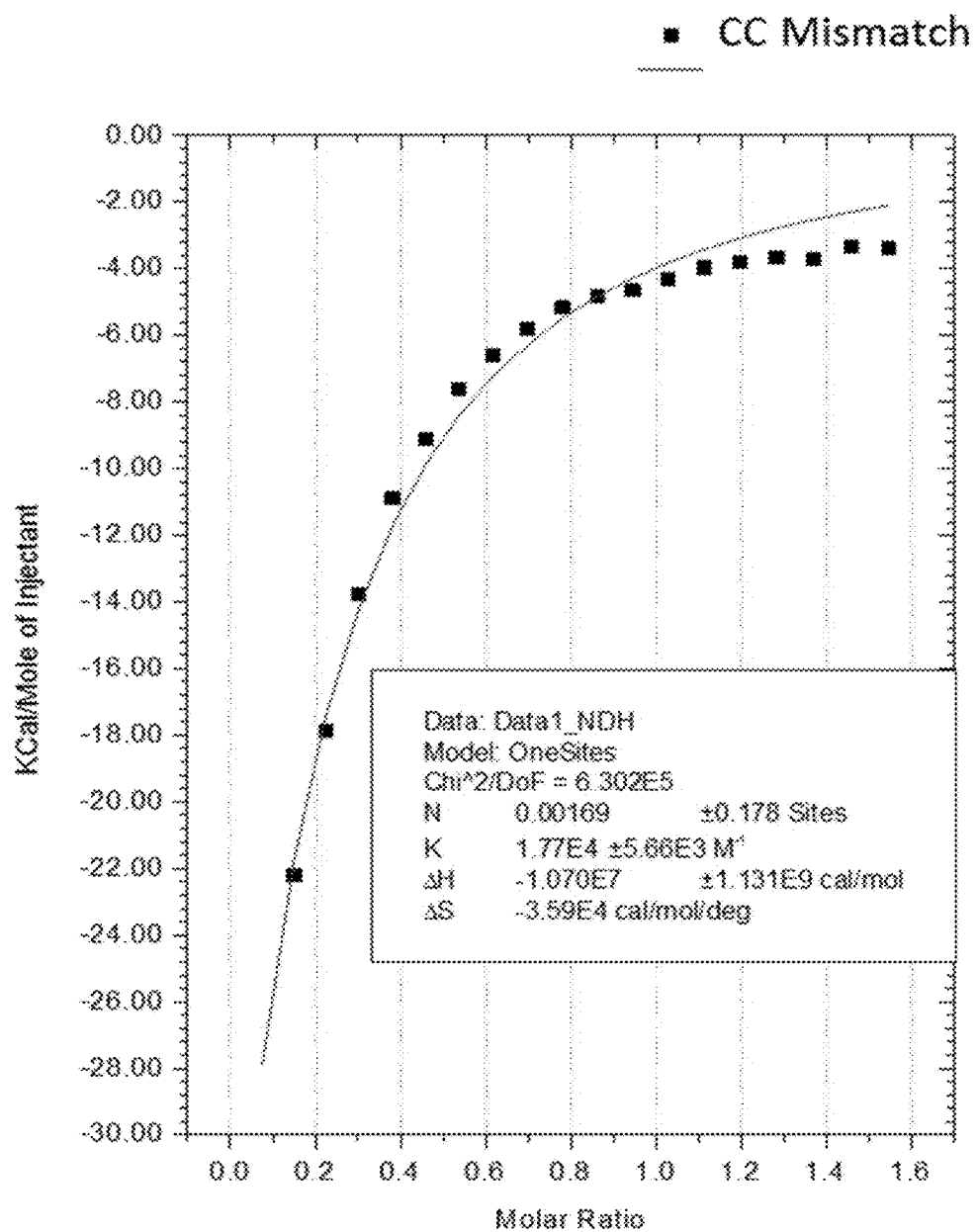
FIGS. 13A and 13B are graphs showing heat release from titrating 0.75 mM of CC mismatched DNA (left) and well-matched DNA (right) into 0.1 mM of complex 1 in an aqueous buffer solution (50 mM NaCl, 2 mM Tris, pH7.5).
Figure 13B:
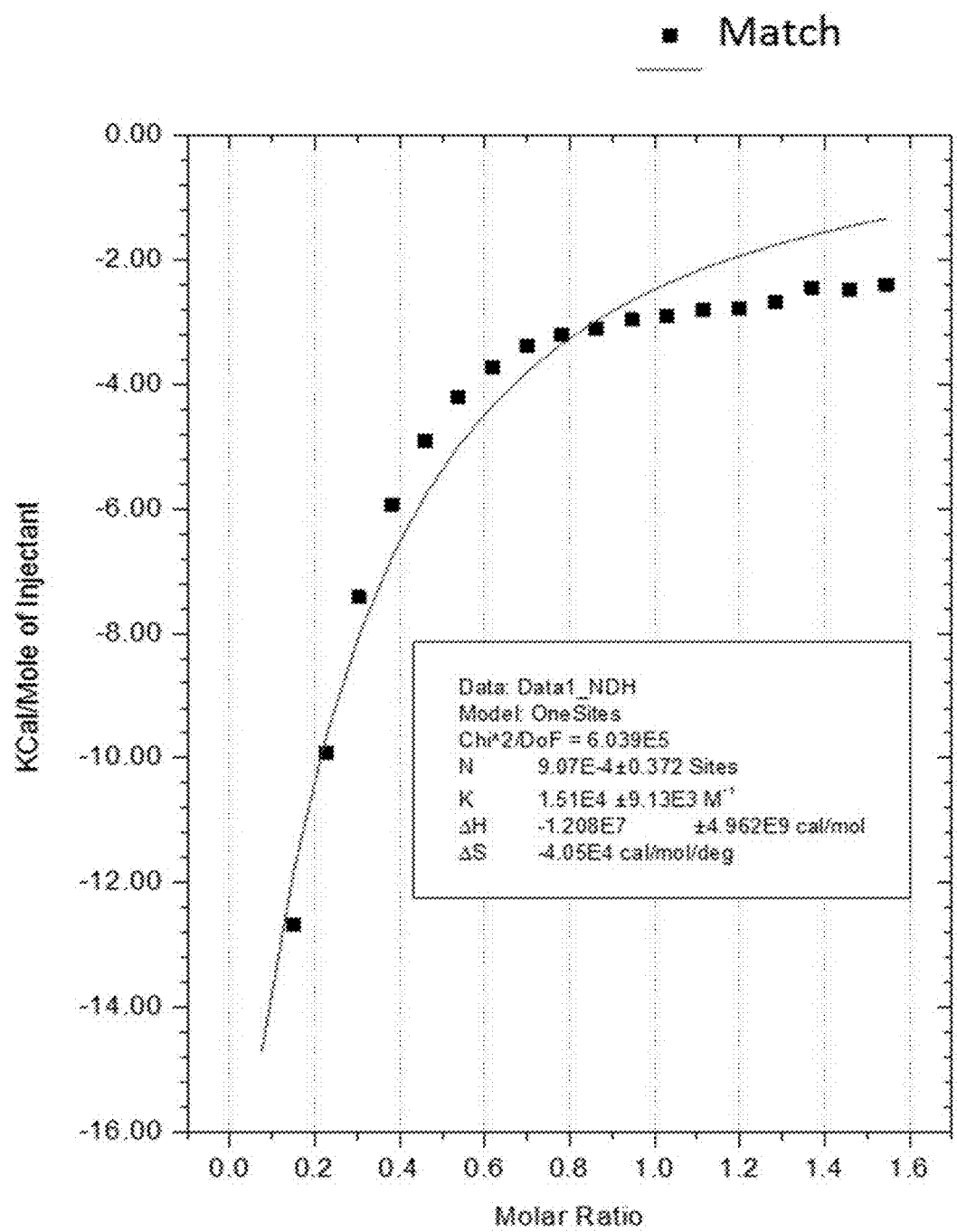

In order to confirm the importance of substituents on NHC ligands for specific binding toward CC mismatch site, complex 1, which contains methyl substituents on the NHC ligand, was used as a reference and studied by ITC experiment. When titrating CC mismatched DNA and matched DNA into complex 1, no distinguishable difference in heat change was observed (FIGS. 13A and 13B), indicating a similar binding constant of complex 1 towards both CC mismatched and matched DNA. As a result, "decorations" of square-planar platinum(II) complexes with ligands of suitable steric bulkiness would be useful in achieving good specificity towards mismatched DNA.

Example 4

Increasing Melting Temperature of CC Mismatched DNA by Binding with Pt(II) Complexes Example 4 explores the binding of complex 23 toward CC mismatched DNA by monitoring the increment of melting temperature.

Figure 14:
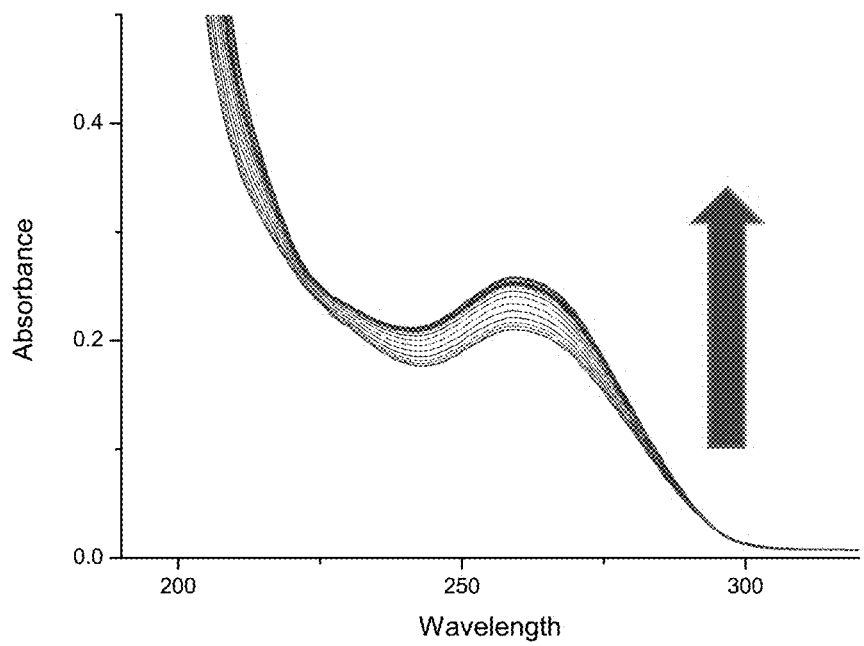
FIG. 14 is a graph showing The increment of UV-vis absorption at 260 nm of CC mismatched DNA (2 μM) with complex 23 (2 μM) upon increasing temperature.

The melting temperature is the temperature at which half of the DNA strands are denatured. The DNA strand separation is monitored by the absorbance of DNA at 260 nm, as the separated DNA would show an increase in the UV-vis absorption at 260 nm compared to that of the duplex DNA (FIG. 14). Therefore, melting temperature of a particular DNA can be deduced by a plot of UV-vis absorption spectral changes at 260 nm against temperature.

Figure 15:
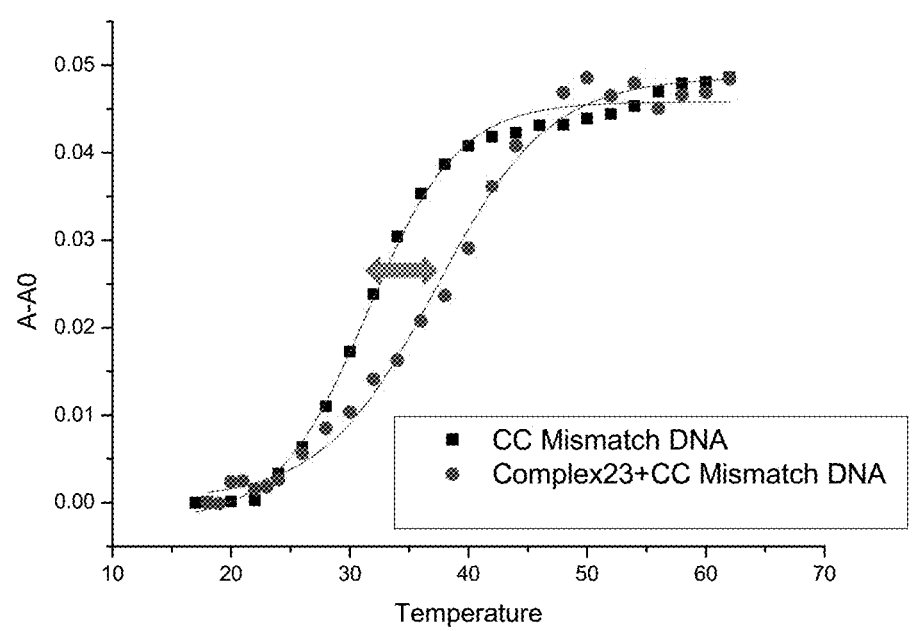
FIG. 15 is a graph showing The change in UV-vis absorption at 260 nm of CC mismatched DNA (2 μM) with or without complex 23 (2 μM) upon increasing temperature.

After mixing complex 23 (2 μM) and CC mismatched DNA or matched DNA (2 μM) for 15 minutes, the UV-vis absorption spectral changes of the ensemble with temperature were measured, and the melting temperatures of the DNA in the presence of complex 23 were determined. These melting temperatures have been compared to those of the DNAs alone without complex 23. It was found that the CC mismatched DNA showed a higher melting temperature in the presence of complex 23 than that without the platinum (II) complex (6° C.; FIG. 15). On the other hand, almost no difference in melting temperature of matched DNA with or without complex 23 was observed. These indicate a strong binding of complex 23 towards CC mismatched DNA, thus higher temperature is required to denature the DNA strands compared to the study of CC mismatched DNA alone. As negligible change in melting temperature of matched DNA by complex 23 was found, a relatively weak binding of complex 23 with matched DNA is indicated, and this is further supported by the emission studies of complex 23 and matched DNA (FIGS. 9A, 9B, 9C, and 9D).

Example 5

In Vitro Cytotoxicity of the Pt(II)-NHC Complexes

Example 5 describes the in vitro cytotoxicity, which is indicative of the induction of cell death and/or inhibition of cellular proliferation of cancer cells, of the Pt(II)-NHC complexes on human colon cancer, cervical epithelioid carcinoma and breast cancer cell.

By means of MTT assays, the cytotoxic properties of different complexes were determined toward some established human cancer cell lines including colon cancer (HCT116), cervical epithelioid carcinoma (Hela) and breast cancer (MDA116). The $IC_{50}$ values (does required to inhibit 50% cellular growth for 72 hr) of the platinum(II) complexes are listed in Table 1. All the Pt(II)-NHC complexes exhibit promising cytotoxicity toward these cell lines with $IC_{50}$ values range of 0.18 to 21 μM. In terms of the $IC_{50}$ values, they display lower cytotoxic properties compared to the reference complexes cisplatin.

TABLE 1

Cytotoxicity $IC_{50}$ of the Pt(II)-NHC complexes to selected human cancer cell lines

| | HCT116 | Hela | MDA |
|---|---|---|---|
| 4 | 0.2 ± 0.1 | 2.9 ± 0.3 | 1.0 ± 0.2 |
| 5 | 0.1 ± 0.1 | 2.6 ± 0.2 | 0.8 ± 0.2 |

TABLE 1-continued

Cytotoxicity IC$_{50}$ of the Pt(II)-NHC complexes to selected human cancer cell lines

|  | HCT116 | Hela | MDA |
|---|---|---|---|
| 6 | 0.4 ± 0.2 | 2.8 ± 0.2 | 4.2 ± 0.6 |
| 7 | 0.1 ± 0.1 | 2.4 ± 0.4 | 0.7 ± 0.1 |
| 8 | 0.4 ± 0.1 | 3.5 ± 0.8 | 3.2 ± 0.7 |
| 15 | 0.2 ± 0.1 | 1.9 ± 0.2 | 0.7 ± 0.1 |
| 16 | 18.9 ± 0.7 | 0.3 ± 0.1 | 0.3 ± 0.1 |
| Cisplatin | 14.5 ± 2.3 | 6.4 ± 1.6 | 21.6 ± 2.3 |

Example 6

Selective detection of DNA in MMR proficient cancer cells

Figure 16:
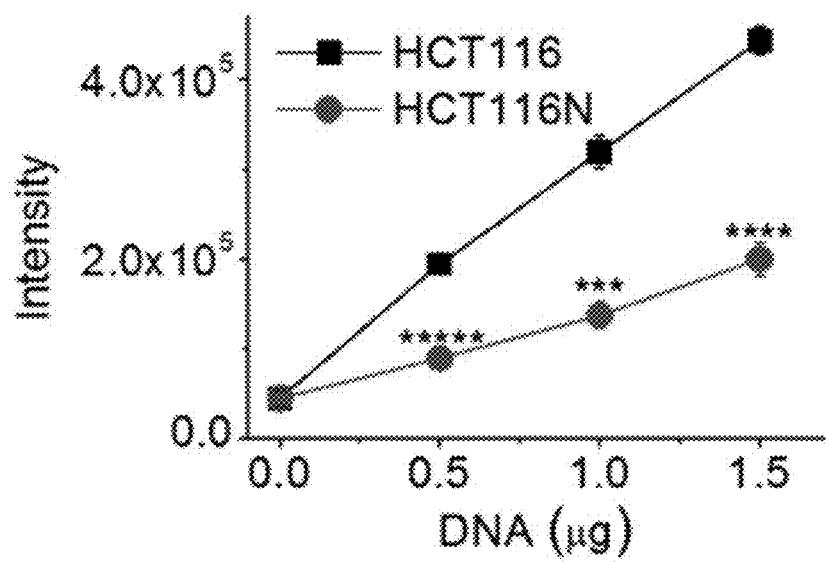
FIG. 16 is a graph showing changes in emission intensity of 23(5 μM) at 634 nm in an aqueous buffer solution (50 mM NaCl, 2 mM Tris, pH 7.5) after binding to different concentrations of colorectal carcinoma DNAs.
Figure 17:
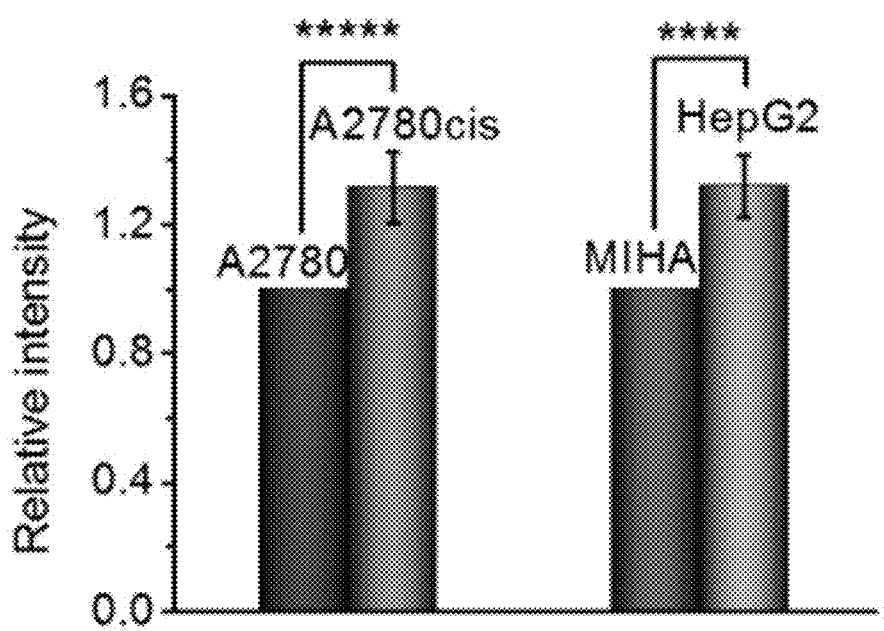
FIG. 17 is a graph showing relative emission intensity of 23 (5 μM in solution containing 50 mM NaCl, 2 mM Tris, pH 7.5) in the presence of 0.5-3.0 μg of DNA extracts from different cells (* p<0.001,  p<0.0001, *** p<0.00001).
Figure 18:
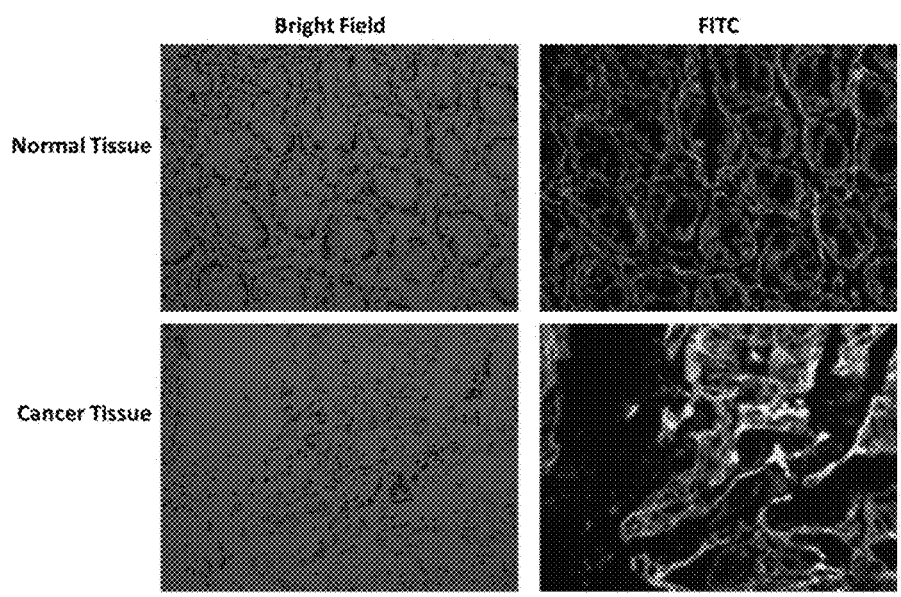
FIG. 18 is a picture of tumor and normal tissues using hematoxylin and eosin stain (H&E stain).
Figure 19:
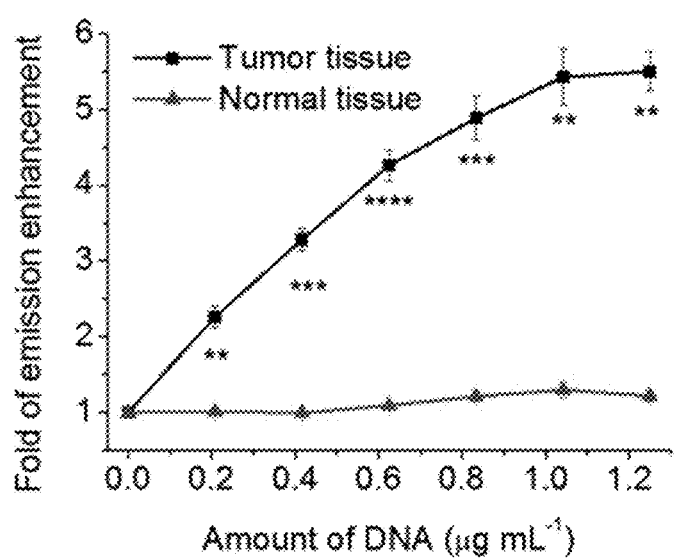
FIG. 19 is a graph of emission responses of 23 towards different concentrations of DNA ex-tracted from colon tissues (p<0.01, * p<0.001, **** p<0.0001).
Figure 20:
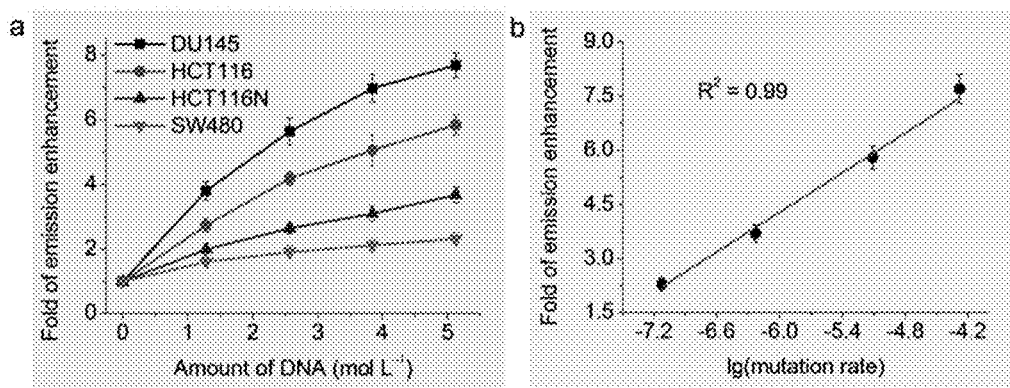
FIG. 20 (a) is a graph of changes in emission intensity (±s.e.m.) of 23 (5 μM) at 634 nm in an aqueous buffer solution (50 mM NaCl, 2 mM Tris, pH 7.5) after binding to DNA extracts from different cancer cells.

The human colorectal carcinoma HCT116 is known to have mutations in the hMLH1 gene which encodes the mismatch repair (MMR) machinery proteins and is thus MMR deficient, while the HCT116 cells transfected with normal hMLH1 on chromosome 3 restored MMR proficiency (the transfected cell line is denoted as HCT116N). It was found that 23 has a much stronger emission intensity at $\lambda_{max}$=634 nm in the presence of DNA extracts from HCT116 cells than the same amount of HCT116N DNA extracts (FIG. 16). For example, upon addition of 1.5 μg of DNA, the emission intensity of 23 towards HCT116 DNA is 2.5-fold higher than HCT116N DNA (p<0.0001). Besides, it is known that the resistance of human ovarian carcinoma A2780cis towards cisplatin is partially correlated with loss of proficiency in MMR compared to the cisplatin sensitive A2780 cells. It was identified that the emission intensity of 23 towards A2780cis DNA is 1.31-fold higher than A2780 DNA with statistically significant difference (p<0.00001, FIG. 17). Moreover, hepatocellular carcinoma is another MMR deficient cell which shows reduced expression of several MMR genes (e.g. hMSH2, hMLH1) compared to the nearby normal tissues. The emission intensity of 23 in the presence of hepatocellular liver carcinoma HepG2 DNA is 1.32-fold higher than the DNA extracted from non-tumorigenic immortalized liver cell MIHA (p<0.0001, FIG. 17). All of these results indicate that the Pt(II) complexes are able to differentiate cancer cells with different levels of MMR expression and could potentially differentiate cancer cells from normal cells.

Example 7

Fluorescence Microscopic Detection of MMR Proficient Cancer Cells by Complex 23

HCT116 cancer cells and NCM460 normal were firstly permeabilized by digitonin and the cytoplasmic proteins were washed out to minimize fluorescence background attributed to protein binding of 23. The emission signal of 23 (10 μM) from HCT116 cells was significantly stronger than that from NCM460 cells. When HCT116 and NCM460 cells were co-cultured in the same dish and stained by 23 (10 μM), the emission from the HCT116 was also significantly stronger than that from NCM460 cells. For comparison, no differential emission was identified in these co-cultured cells stained by ethidium bromide (EB). Thus, 23 could selectively stain cancerous HCT116 cells having elevated levels of mismatched DNA in the presence of normal NCM460 cells. This result indicates that luminescent Pt(II) complexes can be used for distinguishing certain types of cancer cells from normal cells.

Example 8

Emission Responses by Complex 23

Human colon tumor tissues and the surrounding normal colon tissues were obtained from a cancer patient. First, the tumor and normal tissues were confirmed by H&E staining (FIG. 1), which showed that the homology of the tumor tissue is obviously disrupted compared to the normal counterpart. Then, the genomic DNA were extracted from the normal tissues and the tumor tissues, and the emission responses of 23 towards using both types of DNA were studied, which is shown in FIG. 2. In the presence of 0.2-1.25 μg mL$^{-1}$ of DNA extracted from the normal colon tissues, weak emission responses of up to 1.3-fold of initial emission intensity were detected; by contrast, the emission intensity increased in a concentration-dependent manner in the presence of 0-1.0 μg mL$^{-1}$ of DNA extracted from colon tumor tissues, showing up to 5.5-fold emission enhancements at 1.25 μg mL$^{-1}$. Thus, there is a differentiation in emission responses between the DNA of human colon tumor tissue and that of the normal nearby tissue when 23 is used. Since the Pt(II) complex could differentiate the mismatched DNA, the possibility of using the Pt(II) complex to discriminate human cells with different mutation rate was tested. The emission responses of 23 to genomic DNA isolated from several types of cancer cells with different mutation rates were tested. The human cancer cell lines DU145, HCT116, HCT116N and SW480 have mutation rates in the hprt gene locus of 529×10$^{-7}$, 77.5×10$^{-7}$, 5.9×10$^{-7}$ and 0.75×10$^{-7}$, respectively, and the relative emission intensities of 23 (5 μM) at 5.1 mol L$^{-1}$ of DNA are 7.7, 5.8, 3.7 and 2.3, respectively (FIG. 3a shows an increase of emission intensity at 0-5.1 mol L$^{-1}$ of genomic DNA from different cancer cells) [Glaab, W. E., et al. *Carcinogenesis*. 1997, 18, 1]. Notably, the plot of the fold of emission increase versus the lg(mutation rate) yields a linear fit with R$^2$=0.99, as shown in FIG. 3b, indicating a strong correlation between emission response and mutation rate.

The differential emission responses of the Pt(II) complexes to DNA from human colon cancer tissues and normal colon tissues, together with the fact that the ability of Pt(II) complexes differentiating cells with different levels of mutation rates suggest that the Pt(II) complex that it is a good candidate for tumor diagnosis via simple emission spectroscopy measurements of DNA extracts.

It is understood that the disclosed method and complexes are not limited to the particular methodology, protocols, and reagents described as these may vary. It is also to be understood that the terminology used herein is for the purpose of describing particular embodiments only, and is not intended to limit the scope of the present invention which will be limited only by the appended claims.

Those skilled in the art will recognize, or be able to ascertain using no more than routine experimentation, many equivalents to the specific embodiments of the method and complexes described herein. Such equivalents are intended to be encompassed by the following claims.

We claim:

1. A method to target mismatched DNA, the method comprising
bringing into contact a DNA sample comprising pairing nucleobases and/or non-pairing nucleobases and a $d^8$ square planar metal complex, and
detecting the emission of the complex intercalated into DNA in the sample,
wherein emission above a threshold level indicates the presence of mismatched DNA in the sample, wherein the threshold level is the emission from a metal complex intercalated into a well-matched DNA, and
wherein the complex has a structure according to Formula I or Formula II:

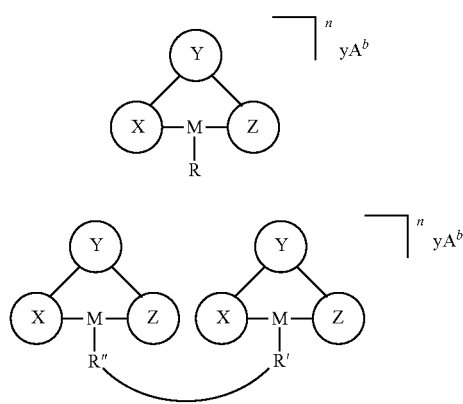

wherein:
X^Y^Z and X'^Y'^Z' are each, independently, a tridentate π-conjugated ligand;
X, Y, Z, X', Y', and Z' are each, independently, carbon or nitrogen;
R, R', and R" are each, independently, a N-heterocyclic carbene ligand or a phosphine ligand;
each M is a $d^8$ metal atom;
n is the charge of the complex;
A is the counter-ion for the complex;
b is the charge of the counter-ion; and
y is the absolute value of n/b.

2. The method of claim 1, in which the complex has a structure according to Formula I-A:

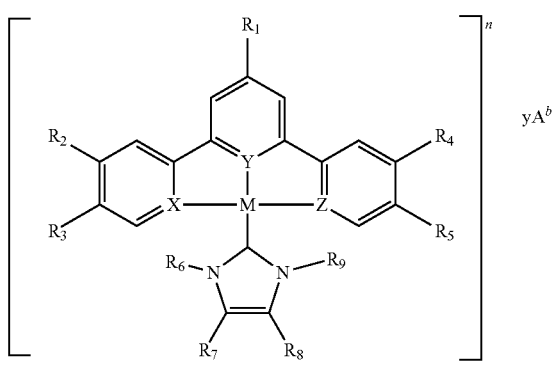

wherein:
M is Au, Pt, or Pd;
$R_1$ is hydrogen or phenyl;
$R_2$ and $R_3$ are each hydrogen or together are —CH—CH—CH—CH—;
$R_4$, $R_5$, $R_7$, and $R_8$ are each hydrogen;
$R_6$ and $R_9$ are each independently selected from —CH$_3$, —C$_2$H$_5$, —C$_3$H$_7$, —C$_4$H$_9$, —C$_5$H$_{11}$, C$_6$H$_{13}$, benzyl, (2-hydroxy) ethyl, phenyl, naphthalen-2-ylmethyl, or (2-phenyl) ethyl;
n is +1 or +2; and
X, Y, Z are each independently carbon or nitrogen.

3. The method of claim 2, in which:
M is Platinum;
$R_1$, $R_2$, $R_3$, $R_4$, $R_5$, $R_7$, and $R_8$ are each hydrogen;
$R_6$ is benzyl;
$R_9$ is —C$_4$H$_9$;
n is +1;
$yA^b$ is CF$_3$SO$_4^-$;
X is carbon; and
Y and Z are each nitrogen.

4. The method of claim 2, in which the complex has a structure according to Formula I, wherein M is coordinated to an anionic or di-anionic 1,3-di(pyridin-2-yl)benzene (N^C^N) ligand, 2,6-diphenylpyridine (C^N^C) ligand, 6-phenyl-2,2'-bipyridine (C^N^N) ligand, 6-(naphthalen-2-yl)-2,2'-bipyridine ligand, 4,6-diphenyl-2,2'-bipyridine ligand, or a N-heterocyclic carbene ligand.

5. The method as in claim 1, in which each M is, independently, platinum(II) (Pt(II) or Pt$^{2+}$), palladium(II) (Pd(II) or Pd$^{2+}$), or gold(III) (Au(III) or Au$^{3+}$).

6. The method as in either claim 1 or 2, in which the non-pairing nucleobases are selected from the group consisting of: adenine/adenine (A/A), adenine/guanine (A/G), adenine/cytosine (A/C), guanine/guanine (G/G), guanine/thymine (G/T), thymine/cytosine (T/C), thymine/thymine (T/T), and cytosine/cytosine (C/C) nucleobases.

7. The method as in either claim 1 or 2, in which detecting the emission of the complex intercalated into DNA in the sample is selected from the group consisting of: emission spectroscopy, UV-Vis absorption spectroscopy, isothermal titration calorimetry (ITC), and nuclear magnetic resonance (NMR) spectroscopy.

8. The method of claim 1, in which the complex has a structure according to Formula II, wherein the two M are each coordinated to an anionic 6-phenyl-2,2'-bipyridine (C^N^N) ligand and are connected with bis-N-heterocyclic carbene or diphosphine ligand.

9. The method of claim 1, in which the mismatched DNA comprises DNA containing one or more non-pairing nucleobases.

10. The method of claim 1, in which R'^R" is a bis-N-heterocyclic carbene or diphosphine ligand.

11. The method as in either claim 1 or 10, in which the complex has a structure according to Formula II-A:

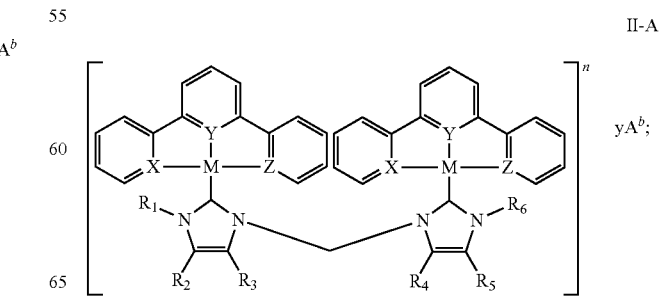

wherein:
    each M is independently selected from Au, Pt, or Pd;
    $R_2$, $R_3$, $R_4$, and $R_5$ are each hydrogen;
    $R_1$ and $R_6$ are each independently selected from —$CH_3$, benzyl, or naphthalen-2-ylmethyl;
    n is +1 or +2;
    y is equal to the absolute value of n/b; and
    each X, Y, and Z are independently carbon or nitrogen.

12. The method of claim 1, in which:
    each M is Platinum;
    $R_2$, $R_3$, $R_4$, and $R_5$ are each hydrogen;
    $R_1$ and $R_6$ are each benzyl;
    n is +2;
    yAb is 2 $CF_3SO_3^-$;
    each X is carbon, and
    each Y and Z is nitrogen.

13. The method of claim 1, in which the DNA sample comprises a cell of a subject, wherein emission above a threshold level indicates that the cell is a cancer cell.

14. The method of claim 13, further comprising treating the subject with an anti-cancer therapy.

15. The method of claim 1, in which the complex has a structure according to Formula II-B:

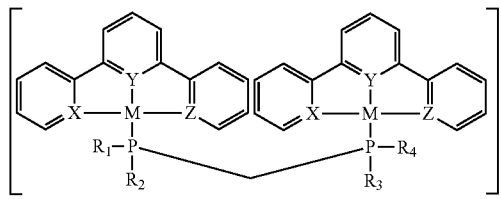

II-B wherein:
    each M is independently selected from Au, Pt or Pd;
    $R_1$, $R_2$, $R_3$, and $R_4$ are each independently selected from phenyl or $C_6H_6$;
    n is +1 or +2;
    y is equal to the absolute value of n/b; and
    each X, Y, and Z are independently carbon or nitrogen.

16. The method of claim 15, in which:
    each M is Platinum;
    $R_1$, $R_2$, $R_3$, and $R_4$ are each phenyl;
    n is +2;
    yAb is 2 $CF_3SO_3^-$;
    each X is carbon, and
    each Y and Z is nitrogen.

17. The method as in claim 2, in which each M is, independently, platinum(II) (Pt(II) or $Pt^{2+}$), palladium(II) (Pd(II) or $Pd^{2+}$), or gold(III) (Au(III) or $Au^{3+}$).

18. The method as in claim 2, in which the non-pairing nucleobases are selected from the group consisting of: adenine/adenine (A/A), adenine/guanine (A/G), adenine/cytosine (A/C), guanine/guanine (G/G), guanine/thymine (G/T), thymine/cytosine (T/C), thymine/thymine (T/T), and cytosine/cytosine (C/C) nucleobases.

19. The method as in claim 2, in which detecting the emission of the complex intercalated into DNA in the sample is selected from the group consisting of: emission spectroscopy, UV-Vis absorption spectroscopy, isothermal titration calorimetry (ITC), and nuclear magnetic resonance (NMR) spectroscopy.

20. The method as in claim 10, in which the complex has a structure according to Formula II-A:

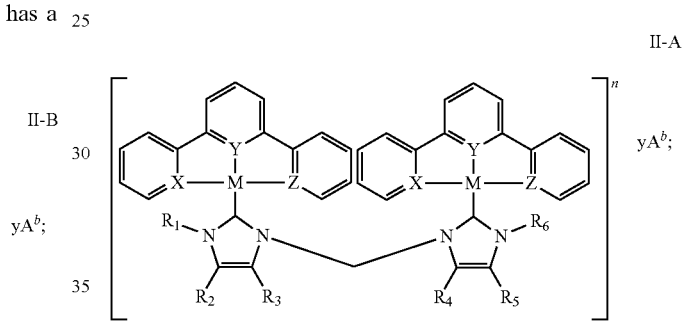

II-A wherein:
    each M is independently selected from Au, Pt, or Pd;
    $R_2$, $R_3$, $R_4$, and $R_5$ are each hydrogen;
    $R_1$ and $R_6$ are each independently selected from —$CH_3$, benzyl, or naphthalen-2-ylmethyl;
    n is +1 or +2;
    y is equal to the absolute value of n/b; and
    each X, Y, and Z are independently carbon or nitrogen.

* * * * *

UNITED STATES PATENT AND TRADEMARK OFFICE
CERTIFICATE OF CORRECTION

PATENT NO. : 10,378,046 B2
APPLICATION NO. : 15/167151
DATED : August 13, 2019
INVENTOR(S) : Chi Ming Che, Sin Ki Fung and Taotao Zou Page 1 of 1

It is certified that error appears in the above-identified patent and that said Letters Patent is hereby corrected as shown below:

In the Specification

Column 7,
Line 35, "(NACAN) ligand, 2,6-diphenylpyridine (CANAC)" should read --(N^C^N) ligand, 2,6-diphenylpyridine (C^N^C)--.

Column 8,
Line 56, "showing The increment" should read --showing the increment--.
Line 59, "showing The change" should read --showing the change--.

Column 9,
Line 42, "conceive" should read --conceived--.

Column 16,
Line 66, "(NACAN) ligand, 2,6-diphenylpyridine (CANAC)" should read --(N^C^N) ligand, 2,6-diphenylpyridine (C^N^C)--.

Column 22,
Line 24, "(HUNAN)" should read --(HC^N^N)--.

Column 26,
Line 10, "R$_9$ 1S" should read --R$_9$ is--.

Column 45,
Line 28, "11NMR" should read --H NMR--.

Signed and Sealed this
Third Day of November, 2020

Andrei Iancu
*Director of the United States Patent and Trademark Office*